(12) United States Patent
Cai et al.

(10) Patent No.: US 9,630,978 B2
(45) Date of Patent: Apr. 25, 2017

(54) POLYCYCLIC-CARBAMOYLPYRIDONE COMPOUNDS AND THEIR PHARMACEUTICAL USE

(71) Applicant: Gilead Sciences, Inc., Foster City, CA (US)

(72) Inventors: Zhenhong R. Cai, Palo Alto, CA (US); Haolun Jin, Foster City, CA (US); Scott E. Lazerwith, San Francisco, CA (US); Hyung-Jung Pyun, Fremont, CA (US)

(73) Assignee: GILEAD SCIENCES, INC., Foster City, CA (US)

( * ) Notice: Subject to any disclaimer, the term of this patent is extended or adjusted under 35 U.S.C. 154(b) by 0 days.

(21) Appl. No.: 15/089,342

(22) Filed: Apr. 1, 2016

(65) Prior Publication Data
US 2016/0289246 A1 Oct. 6, 2016

Related U.S. Application Data

(60) Provisional application No. 62/142,338, filed on Apr. 2, 2015.

(51) Int. Cl.
| | |
|---|---|
| *C07D 513/22* | (2006.01) |
| *A61K 31/4985* | (2006.01) |
| *A61K 31/5365* | (2006.01) |
| *A61K 45/06* | (2006.01) |
| *C07D 491/22* | (2006.01) |
| *C07D 498/16* | (2006.01) |
| *C07D 498/22* | (2006.01) |
| *A61K 31/4375* | (2006.01) |
| *C07D 491/14* | (2006.01) |
| *C07D 498/14* | (2006.01) |

(52) U.S. Cl.
CPC ........ *C07D 513/22* (2013.01); *A61K 31/4375* (2013.01); *A61K 31/4985* (2013.01); *A61K 31/5365* (2013.01); *A61K 45/06* (2013.01); *C07D 491/14* (2013.01); *C07D 491/22* (2013.01); *C07D 498/14* (2013.01); *C07D 498/16* (2013.01); *C07D 498/22* (2013.01)

(58) Field of Classification Search
None
See application file for complete search history.

(56) References Cited

U.S. PATENT DOCUMENTS

| | | | |
|---|---|---|---|
| 5,814,639 A | 9/1998 | Liotta et al. | |
| 5,914,331 A | 6/1999 | Liotta et al. | |
| 5,922,695 A | 7/1999 | Arimilli et al. | |
| 5,935,946 A | 8/1999 | Munger, Jr. et al. | |
| 5,977,089 A | 11/1999 | Arimilli et al. | |
| 6,043,230 A | 3/2000 | Arimilli et al. | |
| 6,620,841 B1 | 9/2003 | Fujishita et al. | |
| 6,642,245 B1 | 11/2003 | Liotta et al. | |
| 6,703,396 B1 | 3/2004 | Liotta et al. | |
| 7,176,220 B2 | 2/2007 | Satoh et al. | |
| 7,419,969 B2 | 9/2008 | Naidu et al. | |
| 7,550,463 B2 | 6/2009 | Yoshida | |
| 7,635,704 B2 | 12/2009 | Satoh et al. | |
| 7,858,788 B2 | 12/2010 | Yoshida et al. | |
| 8,129,385 B2 | 3/2012 | Johns et al. | |
| 8,148,374 B2 | 4/2012 | Desai et al. | |
| 8,188,271 B2 | 5/2012 | Yoshida et al. | |
| 8,410,103 B2 | 4/2013 | Johns et al. | |
| 8,592,397 B2 | 11/2013 | Dahl et al. | |
| 8,633,219 B2 | 1/2014 | Matsuzaki et al. | |
| 8,716,264 B2 | 5/2014 | Dahl et al. | |
| 8,778,943 B2 | 7/2014 | Johns et al. | |
| 8,981,103 B2 | 3/2015 | Ando et al. | |
| 8,987,441 B2 | 3/2015 | Takahashi et al. | |
| 9,051,337 B2 | 6/2015 | Johns et al. | |
| 9,216,996 B2 | 12/2015 | Jin et al. | |

(Continued)

FOREIGN PATENT DOCUMENTS

| | | | |
|---|---|---|---|
| EP | 1422218 A1 | 5/2004 | |
| EP | 1544199 A1 | 6/2005 | |

(Continued)

OTHER PUBLICATIONS

Agrawal, A., et al. (2012) "Probing Chelation Motifs in HIV Integrase Inhibitors" Proc. Natl. Acad. Sci. U.S.A.; 109(7):2251-2256.
AIDS treatment Guidelines—"AIDSinfo Guidelines for the Use of Antiretroviral Agents in HIV-1-Infected Adults and Adolescents," [downloaded from http://aidsinfo.nih.gov/guidelines on Mar. 15, 2013], 267 pages; retrieved M. J. Edwards.
Akiyama, T. et al. (2013) "Discovery of Novel HIV Integrase Inhibitors Part 2. Selection and Evaluation of an Azabicyclic Carbamoyl Pyridone as apre-Clinical Candidate" Poster, American Chemical Society National Meeting and Exposition; Apr. 7-11; New Orleans, LA.

(Continued)

*Primary Examiner* — Karl J Puttlitz

(57) ABSTRACT

Compounds for use in the treatment of human immunodeficiency virus (HIV) infection are disclosed. The compounds have the following Formula (Ia):

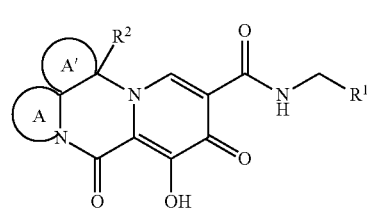

including stereoisomers and pharmaceutically acceptable salts thereof, wherein A, A', $R^1$ and $R^2$ are as defined herein. Methods associated with preparation and use of such compounds, as well as pharmaceutical compositions comprising such compounds, are also disclosed.

24 Claims, No Drawings

(56) References Cited

U.S. PATENT DOCUMENTS

| | | |
|---|---|---|
| 2005/0054645 A1 | 3/2005 | Miyazaki et al. |
| 2005/0137224 A1 | 6/2005 | Shima et al. |
| 2007/0072831 A1 | 3/2007 | Cai et al. |
| 2008/0020010 A1 | 1/2008 | Nair et al. |
| 2008/0139579 A1 | 6/2008 | Morrissette et al. |
| 2008/0161271 A1 | 7/2008 | Yoshida et al. |
| 2008/0280945 A1 | 11/2008 | Lohani et al. |
| 2009/0036684 A1 | 2/2009 | Matsuda et al. |
| 2009/0143356 A1 | 6/2009 | Yoshida et al. |
| 2009/0253677 A1 | 10/2009 | Beaulieu et al. |
| 2009/0318702 A1 | 12/2009 | Matsuda et al. |
| 2010/0068695 A1 | 3/2010 | Kiyama et al. |
| 2012/0022251 A1 | 1/2012 | Sumino et al. |
| 2012/0108564 A1 | 5/2012 | Miyazaki et al. |
| 2014/0011995 A1 | 1/2014 | Sumino et al. |
| 2014/0094605 A1 | 4/2014 | Yoshida et al. |
| 2014/0221355 A1 | 8/2014 | Lazerwith et al. |
| 2014/0221356 A1 | 8/2014 | Jin et al. |
| 2014/0221378 A1 | 8/2014 | Miyazaki et al. |
| 2014/0243521 A1 | 8/2014 | Yoshida et al. |
| 2014/0256937 A1 | 9/2014 | Akiyama |
| 2015/0018359 A1* | 1/2015 | Desai ............... C07D 471/18 514/250 |
| 2015/0232479 A1 | 8/2015 | Johns et al. |
| 2015/0329539 A1* | 11/2015 | Embrey ............ C07D 471/04 514/80 |

FOREIGN PATENT DOCUMENTS

| | | |
|---|---|---|
| EP | 1874117 A1 | 1/2008 |
| EP | 2412709 A1 | 2/2012 |
| EP | 2465580 A1 | 6/2012 |
| EP | 2527007 A1 | 11/2012 |
| EP | 2602260 A1 | 6/2013 |
| GB | 2345058 A | 6/2000 |
| WO | WO-03/030897 A1 | 4/2003 |
| WO | WO-03/035077 A1 | 5/2003 |
| WO | WO-2004/004657 A2 | 1/2004 |
| WO | WO-2004/024078 A2 | 3/2004 |
| WO | WO-2005/042533 A2 | 5/2005 |
| WO | WO-2005/074513 A2 | 8/2005 |
| WO | WO-2005/110414 A2 | 11/2005 |
| WO | WO-2005/112930 A1 | 12/2005 |
| WO | WO-2005/113508 A1 | 12/2005 |
| WO | WO-2005/113509 A1 | 12/2005 |
| WO | WO-2006/066414 A1 | 6/2006 |
| WO | WO-2006/116764 A1 | 11/2006 |
| WO | WO-2007/014352 A2 | 2/2007 |
| WO | WO-2007/049675 A1 | 5/2007 |
| WO | WO-2007/079260 A1 | 7/2007 |
| WO | WO-2007/089030 A1 | 8/2007 |
| WO | WO-2007/102499 A1 | 9/2007 |
| WO | WO-2007/102512 A1 | 9/2007 |
| WO | WO-2008/002959 A2 | 1/2008 |
| WO | WO-2008/033836 A2 | 3/2008 |
| WO | WO-2008/048538 A1 | 4/2008 |
| WO | WO-2009/006199 A1 | 1/2009 |
| WO | WO-2009/006203 A1 | 1/2009 |
| WO | WO-2009/036161 A1 | 3/2009 |
| WO | WO-2010/011812 A1 | 1/2010 |
| WO | WO-2010/011813 A1 | 1/2010 |
| WO | WO-2010/011814 A1 | 1/2010 |
| WO | WO-2010/011815 A1 | 1/2010 |
| WO | WO-2010/011816 A1 | 1/2010 |
| WO | WO-2010/011818 A1 | 1/2010 |
| WO | WO-2010/011819 A1 | 1/2010 |
| WO | WO-2011/094150 A1 | 8/2011 |
| WO | WO-2011/105590 A1 | 9/2011 |
| WO | WO-2011/119566 A1 | 9/2011 |
| WO | WO-2012/018065 A1 | 2/2012 |
| WO | WO-2012/151361 A1 | 11/2012 |
| WO | WO-2012/151567 A1 | 11/2012 |
| WO | WO-2013/038407 A1 | 3/2013 |
| WO | WO-2013/054862 A1 | 4/2013 |
| WO | WO-2014/008636 A1 | 1/2014 |
| WO | WO-2014/011769 A1 | 1/2014 |
| WO | WO-2014/014933 A1 | 1/2014 |
| WO | WO-2014/018449 A1 | 1/2014 |
| WO | WO-2014/022707 A1 | 2/2014 |
| WO | WO-2014/093941 A1 | 6/2014 |
| WO | WO-2014/099586 A1 | 6/2014 |
| WO | WO-2014/100077 A1 | 6/2014 |
| WO | 2014104279 * | 7/2014 |
| WO | WO-2014/104279 A1 | 7/2014 |
| WO | WO-2015/039348 A1 | 3/2015 |
| WO | WO-2015/048363 A1 | 4/2015 |
| WO | WO-2015/089847 A1 | 6/2015 |
| WO | WO-2015/095258 A1 | 6/2015 |

OTHER PUBLICATIONS

Andrews, C. et al. (2014) "Long-Acting Integrase Inhibitor Protects Macaques from Intrarectal Simian/Human Immunodeficiency Virus," Science 343:1151-1154.

Bisel, P. et al. (1998) "Diastereoselective .alpha.-iminoamine rearrangement: asymmetric synthesis of (R)-(-)- and (S)-(-)-2-benzyl-2-hydroxycyclohexanone" Tetrahedron: Asymmetry 9:4027-4034.

Brinson, C. et al. (2013) "Dolutegravir Treatment Response and Safety by Key Subgroups in Treatment Naive HIV Infected Individuals" Poster, 20th Conference on Retroviruses and Opportunistic Infections; Mar. 3-6, 2013; Atlanta, GA.

Cahn, P. et al. (2013) "Dolutegravir (DTG) is Superior to Raltegravir (RAL) in ART-Experienced, Integrase-Naive Subjects: Week 48 Results From Sailing (ING111762)" Presentation, 7.sup.th IAS Conference on HIV Pathogenesis, Treatment and Prevention;Jun. 30-Jul. 3; Kuala Lumpur, Malaysia.

Canducci, F. et al. (2013) "In vitro phenotypes to elvitegravir and dolutegravir in primary macrophages and lymphocytes of clonal recombinant viral variants selected in patients failing raltegravir", J Antimicrob Chemother., 68:2525-32.

Castagna, A. et al. (2014) "Dolutegravir in Antiretroviral-Experienced Patients With Raltegravir- and/or Elvitegravir-Resistant HIV-1: 24-Week Results of the Phase III VIKING-3 Study" Infectious Diseases Society of America Journal of InfectiousDiseases 210:354-62.

Castellino, S., et al., (2013), "Metabolism, Excretion, and Mass Balance of the HIV-1 Integrase Inhibitor Dolutegravir in Humans", Antimicrobial Agents and Chemother., 57:3536-46.

Chen, D. et al. (2003) "New C19-diterpenoid alkaloids from the roots of *Aconitum transsecutum*" Abstract, Huaxue Xuebao 61(6):901-906.

Chen, S. et al. (2014) "Evaluation of the effect of UGT1A1 polymorphisms on dolutegravir pharmacokinetics" Pharmacogenomics, 15(1):9-16.

Clotet, G. et al. (2014) "Once-daily dolutegravir versus darunavir plus ritonavir in antiretroviral-naive adults with HIV-1 infection (FLAMINGO) 48 week results from the randomised open-label phase 3b study", Lancet, 383:2222-31.

Cohen, J. et al. (2014) "A Bid to Thwart HIV With Shot of Long-Lasting Drug" Science 343:1067.

Cottrell, M. et al. (2013) "Clinical Pharmacokinetic, Pharmacodynamic and Drug-Interaction Profile of the Integrase Inhibitor Dolutegravir" Clin Pharmacokinet 52:981-994.

Culp, A. et al. (2014) "Metabolism, Excretion, and Mass Balance of the HIV Integrase Inhibitor, Cabotegravir (GSK1265744) in Humans" Presentation, 54th Intersience Conference on Antimicrobial Agents and Chemotherapy; Sep. 5-9; Washington, DC., 1-7.

Curtis, L. et al. (2013) "Once-Daily Dolutegravir (DTG; GSK1349572) Has a Renal Safety Profile Comparable to Raltegravir (RAL) and Efavirenz in Antiretroviral (ART)-Naive Adults: 48 Week Results From SPRING-2 (ING113086) and SINGLE (ING114467)" Poster No. CUPE 282, 7.sup.th IAS Conference on HIV Pathogenesis, Treatment and Prevention; Jun. 30-Jul. 3; Kuala Lumpur, Malaysia.

Deanda, F. et al. (2013) "Dolutegravir Interactions with HIV-1 Integrase-DNA: Structural Rationale for Drug Resistance and Dissociation Kinetics" PLOS ONE 8(10): e77448 1-12.

(56) References Cited

OTHER PUBLICATIONS

Enright, B. et al. (2010) "Assessment of Hydroxypropyl Methylcellulose, Propylene Glycol, Polysorbate 80, and Hydroxypropyl-.beta.-Cyclodextrin for Use in Developmental and Reproductive Toxicology Studies" Birth Defects Research (Part B) 89:504-516.
FDA DTG Pharmacology Review—Center for Drug Evaluation and Research; DTG PharmTox Review 2013, 103 pages.
FDA_DDI Guidance for Industry—Drug Interaction Studies—Study Design, Data Analysis, Implications for Dosing, and Labeling Recommendations, 79 pages.
Feinberg, J. et al. (2013) "Once-Daily Dolutegravir (DTG) is Superior to Darunavir/Ritonavir (DRV)/f) in Antiretroviral-Naive Adults: 48 Week Results from FLAMINGO (ING114915)" Presentation, 53.sup.rd ICAAC Interscience Conference on AntimicrobialAgents and Chemotherapy; Sep. 10-13; Denver CO.
Gad, S. et al. (2006) "Nonclinical Vehicle Use in Studies by Multiple Routes in Multiple Species" International Journal of Toxicology 25:499-521.
Gao, Y. et al. (2007) "Attenuating Pregnane X Receptor (PXR Activiatin: A Molecular Modeling Approach" Xenobiotica 37(2):124-138.
Gein, V. L., et al. (1992) "Synthesis of 4-Substituted 1-Methyl-5-Aryl- and 1,5-Diaryltetrahydropyrrole-2,3-Diones and their Antiviral Action" translated from Khimik-farmatsevticheskii Zhumal; 25(12):37-40.
Gould, S. et al. (2005) "2-Hydroxypropyl-.beta.-cyclodextrin (HP-.beta.-CD): A toxicology review" Food and Chemical Toxicology 43:1451-1459.
Gouverneur, V. et al. (1998) "New Acylnitroso Compounds for the Asymmetric Oxyamination of Dienes" Tetrahedron 54:10537-10554.
Grobler, J., et al. (2002) "Diketo Acid Inhibitor Mechanism and HIV-1 Integrase: Implications for Metal Binding in the Active Site of Phosphotransferase Enzymes" Proc. Natl. Acad. Sci. U.S.A.; 99(10):6661-6666.
Gutierrez, M., "Drug safety profile of integrase strand transfer inhibitors," Expert Opin. Drug Saf. (2014) 13(4):431-445.
Hare, S. et al. (2011) "Structural and Functional Analyses of the Second-Generation Integrase Strand Transfer Inhibitor Dolutegravir (S/GSK1349572)" Molecular Pharmacology 80(4):565-572.
Hightower, K., "Dolutegravir (S/GKS1349572) Exhibits Siginifcantly Slower Dissociation than Raltegrvir and Elvitegravir from Wild-Type and Integrase Inhibitor-Resistant HIV-1 Integrase-DNA Complexes," Antimicrobial Agents and Chemotherapy 55(10):4552-4559 (2011).
Huang, W. et al. (2014) "Impact of Raltegravir/Elvitegravir Selected Mutationson Dolutegravir Cross-Resistance" Poster 595; 21.sup.st Conference on Retroviruses and Opportunistic Infection; Mar. 3-6; Boston, MA.
Hurt, C. et al. (2013) "Characterization of Resistance to Integrase Strand Transfer Inhibitors among Clinical Specimens in the United States, 2009-2012" Poster 591; 20th Conference on Retroviruses and Opportunistic Infections; Mar. 3-6; Atlanta, GA.
Hurt, et al., (2014), "Resistance to HIV Integrase Strand Transfer Inhibitors Among Clinical Specimens in the United States, 2009-2012", Clin Infect Dis., 58:423-31.
International Preliminary Report on Patentability dated Jun. 23, 2015 for PCT/US2013/076367.
International Search Report dated Jun. 16, 2016 for PCT/US2016/025740.
Intl. Search Report dated Mar. 12, 2014 for PCT/US2013/076367.
Johns, B. et al., (2013), "HIV Integrase Inhibitors", Successful Strategies for Discovery of Antiviral Drugs, 32(6):149-88.
Johns, B., et al., (2013), "Carbamoyl pyridone HIV-1 integrase inhibitors 3. A diastereomeric approach to chiral nonracemic tricyclic ring systems and the discovery of dolutegravir (S/GSK1349572) and (S/GSK1265744)", J. Med. Chem., 56:5901-16.
Johns, B., et al., (2010) "Discovery of S/GSK1349572: A Once Daily Next Generation Integrase Inhibitor with a Superior Resistance Profile", 17th Conference on Retroviruses and Opportunistic Infections Feb. 16-19, 2010, San Francisco, CA, USA (18 pages).
Kawasuji, T., et al. (2007) "3-Hydroxy-1,5-dihydro-pyrrol-2-one Derivatives as Advanced Inhibitors of HIV Integrase" Bioorganic & Medicinal Chemistry; 15:5487-5492.
Kawasuji, T., et al. (2012) "Carbamoyl Pyridone HIV-1 Integrase Inhibitors. 1. Molecular Design and Establishment of an Advanced Two-Metal Binding Pharmacophore" J. Med. Chem.; 55(20):8735-8744.
Kliewer, S. et al. (2002) "The Nuclear Pregnane X Receptor: A Key Regulator of Xenobiotic Metabolism" Endocrine Reviews 23(5):687-702.
Kobayashi, M. et al. (2011) "In Vitro Antiretroviral Properties of S/GSK1349572, a Next-Generation HIV Integrase Inhibitor" Antimicrob Agents and Chemother 55(2):813-21.
Krow, G. et al. (2008) "Selectfluor as a Nucleofuge in the Reactions of Azabicyclo[n. 2.1]alkane.beta.-Halocarbamic Acid Esters (n=2,3)" J. Org. Chem. 73:2122-2129.
Lepist, E. et al. (2011) "Effect of Cobicistat and Ritonavir on Proximal Renal Tubular Cell Uptake and Efflux Tansporters" Poster A1-1724; 51.sup.st Interscience Conference on Antimicrobial Agents and Chemotherapy; Sep. 17-20; Chicago, IL.
Letendre, S. et al. (2013) "Distribution and Antiviral Activity in Cerebrospinal Fluid (CSF) of the Integrase Inhibitor, Dolutegravir (DTG): ING116070 Week 16 Results" Poster 178LB; 20th Conference on Retroviruses and Opportunistic Infections; Mar. 3-6; Atlanta, GA.
Lou, Y. et al. (2013) "Meta-Analysis of Safety Data From 8 Clinical Studies With GSK1265744, an HIV Integrase Inhibitor, Dosed Orally or as Injection of Long-Acting Parenteral Nanosuspension (LAP)" Poster H-672; 53rd Interscience Conference onAntimicrobial Agents and Chemotherapy; Sep. 10-13; Denver, CO.
Maggi, P., (2014) "The Problem of Renal Function Monitoring in Patients Treated With the Novel Antiretroviral Drugs", HIV Clinical Trials, HIV Clin Trials;15(3):87-91.
Malet, I., et al., (2014) "New raltegravir resistance pathways induce broad cross-resistance to all currently used integrase inhibitors", J Antimicrob Chemother, 69: 2118-2122.
Margolis et al. (2014) "744 and Rilpivirine As Two Drug Oral Maintenance Therapy: LAI116482 (LATTE) Week 48 Results" Presentation; 21st Conference on Retroviruses and Opportunistic Infections; Mar. 3-6; Boston, MA.
Menendez-Arias, L., et al., (2013) "Antiretroviral therapy and drug resistance in human immunodeficiency virus type 2 infection", Antiviral Res., 102:70-86.
Metifiot, M. et al. (2013) "HIV Integrase Inhibitors: 20-Year Landmark and Challenges" Advances in Pharmacology 67:75-105.
Min, S. et al. (2010) "Pharmacokinetics and Safety of S/GSK1349572, a Next-Generation HIV Integrase Inhibitor, in Healthy Volunteers" Antimicrob Agents and Chemother 54(1):254-258.
Min, S. et al. (2011) "Antiviral activity, safety, and pharmacokinetics/pharmacodynamics of dolutegravir as 10-day monotherapy in HIV-1-infected adults" AIDS 25(14):1737-1745.
Nair, V. et al. (2014) "Pharmacokinetics and Dose-range Finding Toxicity of a Novel anti-HIV Active Integrase Inhibitor" Supplementary Materials.
Nichols, G. et al (2013) "Phase 3 Assessment of Dolutegravir (DTG) 50 mg Twice Daily (BID) in HIV-1—Infected Subjects With Raltegravir (RAL) and/or Elvitegravir (EVG) Resistance in VIKING-3: Week 24 Results of All 183 Subjects Enrolled" PosterTULBPE19; 7.sup.th IAS Conference on HIV Pathogenesis, Treatment and Prevention Jun. 30-Jul. 3; Kuala Lumpur, Malaysia.
Nichols, G. et al. (2012) "Antiviral Activity of Dolutegravir in Subjects With Failure on an Integrase Inhibitor-Based Regimen: Week 24 Phase 3 Results From VIKING-3" Presentation O232; 11th International Congress on Drug Therapy in HIV Infection:Nov. 11-15; Glasgow, UK.
Nishioka, K. et al. (1992) "C-Labeling of a Tetrahydroacridine, a Novel CNS-Selective Cholinesterase Inhibitor" Journal of Labelled Compounds and Radiopharmaceuticals XXXI(7):553-560.

(56) References Cited

OTHER PUBLICATIONS

Pace, P., et al. (2007) "Dihydroxypyrimidine-4-carboxamides as Novel Potent and Selective HIV Integrase Inhibitors" J. Med. Chem; 50:2225-2239.

Park, B. et al. (2001) "Metabolism of Fluorine-Containing Drugs" Annu. Rev. Pharmacol. Toxicol. 41:443-70.

Patel, P. et al. (2014) "Relative Bioavailability of a Paediatric Granule Formulation of the HIV Integrase Inhibitor, Dolutegravir, in Healthy Adult Subjects" Antiviral Therapy, 19:299-33.

Patel, P., et al., "Pharmacokinetics of the HIV integrase inhibitor S/GSK1349572 co-administered with acid-reducing agents and multivitamins in healthy volunteers," J Antimicrob Chemother (2011); 66: 1567-1572.

Peng, C. et al. (2002) "Norditerpenoid alkaloids from the roots of *Aconitum hemsleyanum Pritz.* var. *pengzhouense*" Abstract, Chinese Chemical Letters 13(3):233-236.

Petrocchi, A., et al. (2007) "From Dihydroxypyrimidine Carboxylic Acids to Carboxamide HIV-1 Integrase Inhibitors: SAR Around the Amide Moiety" Bioorganic & Medicinal Chemistry Letters; 17:350-353.

Pozniak, A. et al. (2013) "Dolutegravir (DTG) Versus Raltegravir (RAL) in ART-Experienced, Integrase-Naive Subjects: 24-Week Interim Results from Sailing (ING111762)" Poster 179LB; 20th Conference on Retroviruses and Opportunistic Infections; Mar. 3-6; Atlanta, GA.

Quashie, P. et al. (2013) "Evolution of HIV integrase resistance mutations" Curr Opin Infect Dis 26:43-49.

Raffi, F. et al. (2012) "Once-daily Dolutegravir (DTG; S/GSK1349572) is Non-inferior to Raltegravir (RAL) in Antiretroviral-naive Adults. 48 Week Results from SPRING-2 (ING113086)" Presentation THLBB04; XIX International AIDS Conference; Jul. 22-27;Washington, DC.

Raffi, F. et al. (2013) "Dolutegravir is Non-Inferior to Raltegravir and Shows Durable Response Through 96 Weeks: Results From the SPRING-2 Trial" Poster TULBPE17; 7.sup.th IAS Conference on HIV Pathogenesis, Treatment and Prevention; Jun. 30-Jul. 3; Kuala Lumpur, Malaysia.

Raffi, F. et al. (2013) "Once-daily dolutegravir versus twice-daily raltegravir in antiretroviral-naive adults with HIV-1 infection (SPRING-2 study): 96 week results from a randomised, double-blind, non-inferiority trial" www.thelancet.com/infection13:927-935.

Raffi, F. et al., (2013) "Once-daily dolutegravir versus raltegravir in antiretroviral-naive adults with HIV-1 infection: 48 week results from the randomised, double-blind, non-inferiority SPRING-2 study", www.thelancet.com.

Ragan, J. et al. (1995) "Studies of the Alkylation of Chiral, Non-Racemic, Tricyclic Pyrrolidinones," Heterocycles 41:57-70.

Reese, M. et al. (2013) "In Vitro Investigations into the Roles of Drug Transporters and Metabolizing Enzymes in the Disposition and Drug Interactions of Dolutegravir, a HIV Integrase Inhibitor" Drug Metab Dispos 41:353-361.

Reviews in Antiviral Therapy Infectious Diseases, Abstract Book 12th International Workshop on Clinical Pharmacology of HIV Therapy, Apr. 13-15, 2011, Miami, Florida USA; available on [http://regist2.virology-education.com/abstractbook/2011_3.pdf] retrieved by M. J. Edwards.

Rhodes, M., et al., "Assessing a Theoretical Risk of Dolutegravir-Induced Developmental Immunotoxicity in Juvenile Rats," Toxicological Sciences 130(1), 70-81 (2012).

Song, I. et al. (2010) "Lack of Interaction Between the HIV Integrase Inhibitor S/GSK1349572 and Tenofovir in Healthy Subjects" JAIDS 55(3):365-367.

Song, I. et al. (2012) "Effect of Food on the Pharmacokinetics of the Integrase Inhibitor Dolutegravir" Antimicrob Agents and Chemother 56(3):1627-1629.

Song, I. et al. (2013) "Dolutegrvir Has No Effect on the Pharmacokinetics of Methadone or Oral Contraceptives With Norgestimate and Ethinyl Estradiol" Poster 535; 20th Conference on Retroviruses and Opportunistic Infections; Mar. 3-6; Atlanta, GA.

Song, I. et al. (2013) "Pharmacokinetics (PK) and PK.sub.—Pharmacodynamic (PD) Relationship of Dolutegravir (DTG) in Integrase Inhibitor (INI)-Naive Subjects" Poster A-1573; 53rd Interscience Conference on Antimicrobial Agents and Chemotherapy;Sep. 10-13; Denver, CO.

Soriano, V., et al. (2011) "Dolutegravir (GSK/ViiV Integrase) Treatment (with 50mg Once & Twice Daily) of HIV Subjects with Raltegravir Resistance & 3-Class ART Resistance: viral suppression at Week 24 in the VIKING Study" Presentation; EACS; Oct. 12-15; Belgrade, Serbia.

Spreen, W. et al (2013) "First study of repeat dose co-administration of GSK1265744 and TMC278 long-acting parenteral nanosuspensions: pharmacokinetics, safety, and tolerability in healthy adults" Presentation; 7.sup.th IAS Conference on HIVPathogenesis, Treatment and Prevention Jun. 30-Jul. 3; Kuala Lumpur, Malaysia.

Spreen, W. et al. (2012) "Pharmacokinetics, Safety and Tolerability of the HIV Integrase Inhibitor S/GSK1265744 Long Acting Parenteral Nanosuspension Following Single Dose Administration to Healthy Adults" Presentation; 19th International AIDSConference; Jul. 22-27; Washington DC.

Spreen, W. et al. (2013) "Pharmacokinetics, Safety, and Monotherapy Antiviral Activity of GSK1265744, an HIV Integrase Strand Transfer Inhibitor" HIV Clin Trials 14(5):192-203.

Stellbrink, H. et al. (2013) "Dolutegravir in antiretroviral-naive adults with HIV-1: 96-week results from a randomized dose-ranging study" AIDS 27:1771-1778.

Summa, V., et al. (2006) "4,5-Dihydroxypyrimidine Carboxamides and N-Alkyl-5-hydroxypyrimidinone Carboxamides are Potent, Selective HIV Integrase Inhibitors with Good Pharmacokinetic Profiles in Preclinical Species" J. Med. Chem; 49:6646-6649.

Summary of Product Characteristics—Annex I, Leaflet, 62 pages—EU—Triumeq [downloaded Sep. 8, 2014].

Taoda, Y. et al. (2013) "Discovery of Novel HIV Integrase Inhibitors Part 1. Molecular Design and SAR of Azabicyclic Carbamoyl Pyridone Inhibitors" Poster; 245.sup.th American Chemical Society National Meeting and Exposition; Apr. 7-11; New Orleans,LA.

Tchaparian, Eskouhie, "Drug Transporters: An Overview of Their Role in Drug Interactions; Recommended Strategies to Assess Drug Transporters froma Regulatory and Industry Perspective," FDA Guidance Compliance Regulatory Information Guidances (Feb. 14, 2013), 19 pages.

Thackaberry, E. et al. (2010) "Comprehensive Investigation of Hydroxypropyl Methylcellulose, Propylene Glycol, Polysorbate 80, and Hydroxypropyl-Beta-Cyclodextrin for use in General Toxicology Studies" Toxicological Sciences 117(2):485-492.

Thomson Reuters Drug New, "Coadministration of long-acting GSK-744 and rilpivirine found feasible" [downloaded on the web http://drugnews.thomson-pharma.com/ddn/article.do?id=124544] Jul. 8, 2013 8:33:31 AM on Mon Jul. 8, 2013, 1 page; retrieved byHaolun Jin.

Thomson Reuters Drug News "Results from phase III trials of dolutegravir presented," Fri Jul. 5, 2013, 1 page; retrieved by Haolun Jin.

Trinite, B. et al. (2013) "An HIV-1 Replication Pathway Utilizing Reverse Transcription Products That Fail to Integrate" Journal of Virology 87(23):12701-12720.

Tseng, A. et al. (2014) "Drug Interactions with Integrase Inhibitors" Pharm. D.

Van Lunzen, J. et al. (2012) "Once daily dolutegravir (S/GSK1349572) in combination therapy in antiretroviral-naive adults with HIV: planned interim 48 week results from SPRING-1, a dose-ranging, randomised, phase 2b trial" Lancet Infectious Disease12(2):111-118.

Wai, J., et al. (2007) "Dihydroxypyridopyrazine-1,6-dione HIV-1 Integrase Inhibitors" Bioorganic & Medicinal Chemistry Letters; 17:5595-5599.

Walmsley, S. et al. (2012) "Dolutegravir (DTG; S/GSK1349572) + Abacavir/Lamivudine Once Daily Statistically Superior to Tenofovir/Emtricitabine/Efavirenz: 48-Week Results—SINGLE

(56) References Cited

OTHER PUBLICATIONS (ING114467)" Presentation H-556b; 52nd Interscience Conference onAntimicrobial Agents and Chemotherapy; Sep. 9-12; San Francisco, CA.
Walmsley, S. et al. (2013) "Dolutegravir plus Abacavir-Lamivudine for the Treatment of HIV-1 Infection" N Engl J Med 369(19):1807-1818.
Wang, F. et al. (1999) "Modifications of norditerpenoid alkaloids. I. N-deethylation reactions" Abstract, Chinese Chemical Letters 10(5):375-378.
Wang, F. et al. (2005) "To seek an approach toward the chemical conversion of C19-diterpenoid alkaloids to taxoids" Tetrahedron 61(8):2149-2167.
Wang, H. et al. (2015) "An Efficient and Highly Diastereoselective Synthesis of GSK1265744, a Potent HIV Integrase Inhibitor" Org. Letters 17:564-567.
Wang, Y., et al., (2002) "Switch in asymmetric induction sense in cycloadditions using camphor-based nitroso dienop", Tetrahedron: Asymmetry 13:691-5.
Weller, S. et al. (2013) "Pharmacokinetics (PK) and Safety of Dolutegravir (DTG) in Subjects With Severe Renal Impairment and Healthy Controls" Poster A-1571; 53rd Interscience Conference on Antimicrobial Agents and Chemotherapy; Sep. 10-13; Denver,CO.
Weller, S., et al., (2013) "Bioequivalence of a Dolutegravir, Abacavir, and Lamivudine Fixed-Dose Combination Tablet and the Effect of Food", Poster A-1572; 53rd Interscience Conference on Antimicrobial Agents and Chemotherapy; Sep. 10-13, 2013; Denver, CO.
Weller, S., et al., (2014), "Bioequivalence of a Dolutegravir, Abacavir, and Lamivudine Fixed-Dose Combination Tablet and the Effect of Food", Acquir Immune Defic Syndr 66(4):393-398.
Wensing, A. et al. (2014) "Special Contribution 2014 Update of the Drug Resistance Mutations in HIV-1" IAS-USA Topics in Antiviral Medicine 22(3):642-650.
Wolkowicz, U. et al. (2014) "Structural Basis of Mos1 Transposase Inhibition by the Anti-retroviral Drug Raltegravir" ACS Chem. Biol. 9:743-751.
Wu, B. et al. (2009) "Enantioselective Desymmetrization of meso-Aziridines with TMSN.sub.3 or TMSCN Catalyzed by Discrete Yttrium Complexes" Angew. Chem. Int. Ed. 48:1126-1129.
Wu, B. et al. (2008) "Enantioselective Desymmetrization of meso-Aziridines with TMSN.sub.3 and TMSCN Catalyzed by Discrete Yttrium Complexes" Supporting Information, Angew. Chem. Int. Ed., 64pgs.
Zhao, X. et al. (2014) "4-Amino-1-hydroxy-2-oxo-1,8-naphthyridine-Containing Compounds Having High Potency against Raltegravir-Resistant Integrase Mutants of HIV-1" J Med Chem 57:5190-5202.
Zheng, X. et al. (2008) "Rapid analysis of a Chinese herbal prescription by liquid chromatography-time-of-flight tandem mass spectrometry" Abstract, Journal of Chromatography A 1206(2:140-146).

* cited by examiner

POLYCYCLIC-CARBAMOYLPYRIDONE COMPOUNDS AND THEIR PHARMACEUTICAL USE

BACKGROUND

Field

Compounds, compositions, and methods that may be used for the treatment of human immunodeficiency virus (HIV) infection are disclosed. In particular, novel polycyclic carbamoylpyridone compounds and methods for their preparation and use as therapeutic or prophylactic agents are disclosed.

Description of Related Art

Human immunodeficiency virus infection and related diseases are a major public health problem worldwide. Human immunodeficiency virus type 1 (HIV-1) encodes three enzymes which are required for viral replication: reverse transcriptase, protease, and integrase. Although drugs targeting reverse transcriptase and protease are in wide use and have shown effectiveness, particularly when employed in combination, toxicity and development of resistant strains have limited their usefulness (Palella, et al. *N. Engl. J Med.* (1998) 338:853-860; Richman, D. D. *Nature* (2001) 410:995-1001). Accordingly, there is a need for new agents that inhibit the replication of HIV.

A goal of antiretroviral therapy is to achieve viral suppression in the HIV infected patient. Current treatment guidelines published by the United States Department of Health and Human Services provide that achievement of viral suppression requires the use of combination therapies, i.e., several drugs from at least two or more drug classes. In addition, decisions regarding the treatment of HIV infected patients are complicated when the patient requires treatment for other medical conditions (Id. at E-12). Because the standard of care requires the use of multiple different drugs to suppress HIV, as well as to treat other conditions the patient may be experiencing, the potential for drug interaction is a criterion for selection of a drug regimen. As such, there is a need for antiretroviral therapies having a decreased potential for drug interactions.

In addition, the HIV virus is known to mutate in infected subjects (Tang et al., *Drugs* (2012) 72 (9) e1-e25). Because of the proclivity of the HIV virus to mutate, there is a need for anti-HIV drugs to be effective against a range of known HIV variants (Hurt et al., *HIV/AIDS CID* (2014) 58, 423-431).

BRIEF SUMMARY

The present disclosure is directed to novel polycyclic carbamoylpyridone compounds having antiviral activity, including stereoisomers and pharmaceutically acceptable salts thereof. In some embodiments, the compounds may be used to treat HIV infections, to inhibit the activity of HIV integrase and/or to reduce HIV replication. In some embodiments, compounds disclosed herein may be effective against a range of known drug-resistant HIV mutants. In some embodiments, compounds disclosed herein may minimize the potential for drug-drug interactions when co-administered with other drugs.

In one embodiment, compounds having the following Formula (Ia) are provided:

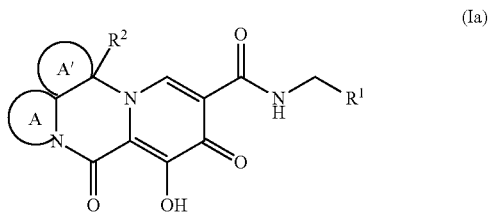

or a pharmaceutically acceptable salt thereof, wherein:

A is a 4 to 7 membered monocyclic heterocyclyl saturated or partially unsaturated and optionally substituted with 1 to 5 $R^3$ groups;

each $R^3$ is independently selected from the group consisting of $C_{1-4}$alkyl, halogen and oxo; or two $R^3$ connected to the same or adjacent carbon atoms form a spiro or fused $C_{3-6}$cycloalkyl or 4 to 6 membered heterocyclyl ring;

A' is selected from the group consisting of $C_{3-7}$ monocyclic cycloalkyl and 4 to 7 membered monocyclic heterocyclyl; wherein each $C_{3-7}$ monocyclic cycloalkyl and 4 to 7 membered monocyclic heterocyclyl is optionally substituted with 1 to 5 $R^4$ groups;

each $R^4$ is independently selected from the group consisting of $C_{1-4}$alkyl, halogen and oxo; or two $R^4$ connected to the same or adjacent carbon atoms form a spiro or fused $C_{3-6}$cycloalkyl or 4 to 6 membered heterocyclyl ring;

$R^1$ is phenyl optionally substituted with 1 to 5 $R^5$ groups;

each $R^5$ is independently selected from the group consisting of halogen and $C_{1-3}$alkyl; and $R^2$ is selected from the group consisting of H, $C_{1-3}$haloalkyl and $C_{1-4}$alkyl.

In another embodiment, a pharmaceutical composition is provided comprising a compound having the Formula (Ia) or pharmaceutically acceptable salt thereof, and a pharmaceutically acceptable excipient.

In another embodiment, a method of treating an HIV infection in a human having or at risk of having the infection by administering to the human a therapeutically effective amount of a compound of Formula (Ia), or a pharmaceutically acceptable salt thereof, or a pharmaceutical composition of a compound of Formula (Ia) or a pharmaceutically acceptable salt thereof, is provided.

In another embodiment, a use of a compound of Formula (Ia), or a pharmaceutically acceptable salt thereof, or a pharmaceutical composition of a compound of Formula (Ia) or a pharmaceutically acceptable salt thereof, for the treatment of an HIV infection in a human having or at risk of having the infection is provided.

In another embodiment, a compound of Formula (Ia), or a pharmaceutically acceptable salt thereof, or a pharmaceutical composition of a compound of Formula (Ia) or a pharmaceutically acceptable salt thereof, for use in medical therapy is provided.

In another embodiment, a compound of Formula (Ia), or a pharmaceutically acceptable salt thereof, or a pharmaceutical composition of a compound of Formula (Ia) or a pharmaceutically acceptable salt thereof, for use in the prophylactic or therapeutic treatment of an HIV infection is provided.

In another embodiment, a method of using a compound having the Formula (Ia) in therapy is provided. In particular, a method of treating the proliferation of the HIV virus, treating AIDS, or delaying the onset of AIDS or ARC symptoms in a mammal (e.g., a human) is provided, comprising administering to the mammal a compound having the Formula (Ia) or a stereoisomer or a pharmaceutically acceptable salt thereof, and a pharmaceutically acceptable excipient.

In another embodiment, a composition comprising a compound having the Formula (Ia) or a stereoisomer or a pharmaceutically acceptable salt thereof, and a pharmaceutically acceptable excipient, for use in a method of treating the proliferation of the HIV virus, treating AIDS, or delaying the onset of AIDS or ARC symptoms in a mammal (e.g., a human) is provided.

In another embodiment, the use of a compound of Formula (Ia) as described herein, or a pharmaceutically acceptable salt thereof, for the manufacture of a medicament for the treatment of an HIV infection in a human being having or at risk of having the infection is disclosed.

In another embodiment, an article of manufacture comprising a composition effective to treat an HIV infection; and packaging material comprising a label which indicates that the composition can be used to treat infection by HIV is disclosed. Exemplary compositions comprise a compound of Formula (Ia) as disclosed herein or a pharmaceutically acceptable salt thereof.

In still another embodiment, a method of inhibiting the replication of HIV is disclosed. The method comprises exposing the virus to an effective amount of the compound of Formula (Ia) or a salt thereof, under conditions where replication of HIV is inhibited.

In another embodiment, the use of a compound of Formula (Ia) to inhibit the activity of the HIV integrase enzyme is disclosed.

In another embodiment, the use of a compound of Formula (Ia) or a pharmaceutically acceptable salt thereof to inhibit the activity of the HIV integrase enzyme is disclosed.

In another embodiment, the use of a compound of Formula (Ia) or a salt thereof, to inhibit the replication of HIV is disclosed.

In another embodiment, the use of a compound of Formula (Ia) or a pharmaceutically acceptable salt thereof, as a research tool is disclosed.

Other embodiments, objects, features and advantages may be set forth in the detailed description of the embodiments that follows, and in part may be apparent from the description, or may be learned by practice, of the claimed embodiments. These objects and advantages may be realized and attained by the processes and compositions particularly pointed out in the written description and claims thereof. The foregoing Summary has been made with the understanding that it is to be considered as a brief and general synopsis of some of the embodiments disclosed herein, is provided solely for the benefit and convenience of the reader, and is not intended to limit in any manner the scope, or range of equivalents, to which the appended claims are lawfully entitled.

DETAILED DESCRIPTION

In the following description, certain specific details are set forth in order to provide a thorough understanding of various embodiments disclosed herein. However, one skilled in the art will understand that the embodiments disclosed herein may be practiced without these details. The description below of several embodiments is made with the understanding that the present disclosure is to be considered as an exemplification of the claimed subject matter, and is not intended to limit the appended claims to the specific embodiments illustrated. The headings used throughout this disclosure are provided for convenience only and are not to be construed to limit the claims in any way. Embodiments illustrated under any heading may be combined with embodiments illustrated under any other heading.

DEFINITIONS

Unless the context requires otherwise, throughout the present disclosure and claims, the word "comprise" and variations thereof, such as, "comprises" and "comprising" are to be construed in an open, inclusive sense, that is as "including, but not limited to".

Reference throughout this specification to "one embodiment" or "an embodiment" means that a particular feature, structure or characteristic described in connection with the embodiment is included in at least one embodiment disclosed herein. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

"Amino" refers to the $-NH_2$ radical.

"Hydroxy" or "hydroxyl" refers to the $-OH$ radical.

"Oxo" refers to the $=O$ substituent.

A prefix such as "$C_{u-v}$" or ($C_u$-$C_v$) indicates that the following group has from u to v carbon atoms. For example, "$C_{1-6}$alkyl" indicates that the alkyl group has from 1 to 6 carbon atoms.

"Alkyl" refers to a straight or branched hydrocarbon chain radical consisting solely of carbon and hydrogen atoms, which is saturated, having from one to twelve carbon atoms ($C_1$-$C_{12}$ alkyl), in certain embodiments one to eight carbon atoms ($C_1$-$C_8$ alkyl) or one to six carbon atoms ($C_1$-$C_6$ alkyl), and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl, and the like.

"Cycloalkyl" or "carbocyclic ring" refers to a stable non-aromatic monocyclic hydrocarbon consisting solely of carbon and hydrogen atoms, having from three to fifteen carbon atoms, in certain embodiments having from three to ten carbon atoms, and which is saturated and attached to the rest of the molecule by a single bond, or in the case of A' attached to the rest of the molecule by two single bonds. Cycloalkyls include, for example, cyclopropyl, cyclobutyl, cyclopentyl, cyclohexyl, cycloheptyl, and cyclooctyl.

"Fused" refers to any ring structure described herein which is fused to an existing ring structure in the compounds disclosed herein.

"Halo" or "halogen" refers to bromo, chloro, fluoro or iodo.

"Haloalkyl" refers to an alkyl group, as defined above, that is substituted by one or more halo radicals, as defined above, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like.

"Heterocyclyl" or "heterocyclic ring" refers to a stable monocyclic 3- to 18-membered non-aromatic ring which consists of two to twelve carbon atoms and from one to six heteroatoms selected from the group consisting of nitrogen, oxygen and sulfur and attached to the rest of the molecule by a single bond, or in the case of A and A' attached to the rest of the molecule by two single bonds. The nitrogen, carbon or sulfur atoms in the heterocyclyl may be optionally oxidized; the nitrogen atom may be optionally quaternized. As used herein, "heterocyclyl" or "heterocyclic ring" refers to rings that are saturated unless otherwise indicated, e.g., in some embodiments "heterocyclyl" or "heterocyclic ring" refers to rings that are saturated or partially saturated where specified. Examples of such heterocyclyl include, but are not limited to, dioxolanyl, imidazolidinyl, isothiazolidinyl, isoxazolidinyl, morpholinyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, thiazolidinyl, tetrahydrofuranyl, trithianyl, tetrahydropyranyl, thiomorpholinyl, thiamorpholinyl, 1-oxo-thiomorpholinyl, and 1,1-dioxo-thiomorpholinyl.

The embodiments disclosed herein are also meant to encompass all pharmaceutically acceptable compounds of Formulas (Ia) being isotopically-labeled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, and iodine, such as $^{123}I$, and $^{125}I$, respectively. These radiolabeled compounds could be useful to help determine or measure the effectiveness of the compounds, by characterizing, for example, the site or mode of action, or binding affinity to pharmacologically important site of action. Certain isotopically-labeled compounds of Formulas (Ia), (II), and (III) for example, those incorporating a radioactive isotope, are useful in drug and/or substrate tissue distribution studies. The radioactive isotopes tritium, i.e. $^{3}H$, and carbon-14, i.e. $^{14}C$, are particularly useful for this purpose in view of their ease of incorporation and ready means of detection.

Substitution with heavier isotopes such as deuterium, i.e. $^{2}H$, may afford certain therapeutic advantages resulting from greater metabolic stability. For example, in vivo half-life may increase or dosage requirements may be reduced. Thus, heavier isotopes may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of Formulas (Ia) can generally be prepared by conventional techniques known to those skilled in the art or by processes analogous to those described in the Examples as set out below using an appropriate isotopically-labeled reagent in place of the non-labeled reagent previously employed.

The methods, compositions, kits and articles of manufacture provided herein use or include compounds (e.g., (Ia)) or pharmaceutically acceptable salts, prodrugs, or solvates thereof, in which from 1 to n hydrogen atoms attached to a carbon atom may be replaced by a deuterium atom or D, in which n is the number of hydrogen atoms in the molecule. As known in the art, the deuterium atom is a non-radioactive isotope of the hydrogen atom. Such compounds may increase resistance to metabolism, and thus may be useful for increasing the half-life of compounds or pharmaceutically acceptable salts, prodrugs, or solvates thereof, when administered to a mammal. See, e.g., Foster, "Deuterium Isotope Effects in Studies of Drug Metabolism", Trends Pharmacol. Sci., 5(12):524-527 (1984). Such compounds are synthesized by means well known in the art, for example by employing starting materials in which one or more hydrogen atoms have been replaced by deuterium.

The embodiments disclosed herein are also meant to encompass the in vivo metabolic products of the disclosed compounds. Such products may result from, for example, the oxidation, reduction, hydrolysis, amidation, esterification, and the like of the administered compound, primarily due to enzymatic processes. Accordingly, the embodiments disclosed herein include compounds produced by a process comprising administering a compound according to the embodiments disclosed herein to a mammal for a period of time sufficient to yield a metabolic product thereof. Such products are typically identified by administering a radiolabeled compound according to the embodiments disclosed herein in a detectable dose to an animal, such as rat, mouse, guinea pig, monkey, or to human, allowing sufficient time for metabolism to occur, and isolating its conversion products from the urine, blood or other biological samples.

"Stable compound" and "stable structure" are meant to indicate a compound that is sufficiently robust to survive isolation to a useful degree of purity from a reaction mixture, and formulation into an efficacious therapeutic agent.

"Mammal" includes humans and both domestic animals such as laboratory animals and household pets (e.g., cats, dogs, swine, cattle, sheep, goats, horses, rabbits), and non-domestic animals such as wildlife and the like.

"Optional" or "optionally" means that the subsequently described event or circumstances may or may not occur, and that the description includes instances where said event or circumstance occurs and instances in which it does not. For example, "optionally substituted heterocyclyl" means that the heterocyclyl radical may or may not be substituted and that the description includes both substituted heterocyclyl radicals and heterocyclyl radicals having no substitution.

"Pharmaceutically acceptable excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

Examples of "pharmaceutically acceptable salts" of the compounds disclosed herein include salts derived from an appropriate base, such as an alkali metal (for example, sodium), an alkaline earth metal (for example, magnesium), ammonium and $NX_4^+$ (wherein X is $C_1$-$C_4$ alkyl). Pharmaceutically acceptable salts of a nitrogen atom or an amino group include for example salts of organic carboxylic acids such as acetic, benzoic, lactic, fumaric, tartaric, maleic, malonic, malic, isethionic, lactobionic and succinic acids; organic sulfonic acids, such as methanesulfonic, ethanesulfonic, benzenesulfonic and p-toluenesulfonic acids; and inorganic acids, such as hydrochloric, hydrobromic, sulfuric, phosphoric and sulfamic acids. Pharmaceutically acceptable salts of a compound of a hydroxy group include the anion of said compound in combination with a suitable cation such as $Na^+$ and $NX_4^+$ (wherein X is independently selected from H or a $C_1$-$C_4$ alkyl group).

For therapeutic use, salts of active ingredients of the compounds disclosed herein will typically be pharmaceutically acceptable, i.e. they will be salts derived from a physiologically acceptable acid or base. However, salts of acids or bases which are not pharmaceutically acceptable may also find use, for example, in the preparation or purification of a compound of Formula (Ia) or another compound of the embodiments disclosed herein. All salts, whether or not derived from a physiologically acceptable acid or base, are within the scope of the embodiments disclosed herein.

Metal salts typically are prepared by reacting the metal hydroxide with a compound according to the embodiments disclosed herein. Examples of metal salts which are prepared in this way are salts containing $Li^+$, $Na^+$, and $K^+$. A less soluble metal salt can be precipitated from the solution of a more soluble salt by addition of the suitable metal compound.

In addition, salts may be formed from acid addition of certain organic and inorganic acids, e.g., HCl, HBr, $H_2SO_4$, $H_3PO_4$ or organic sulfonic acids, to basic centers, typically amines. Finally, it is to be understood that the compositions herein comprise compounds disclosed herein in their un-ionized, as well as zwitterionic form, and combinations with stoichiometric amounts of water as in hydrates.

Often crystallizations produce a solvate of a compound of the embodiments disclosed herein. As used herein, the term "solvate" refers to an aggregate that comprises one or more molecules of a compound of the embodiments disclosed herein with one or more molecules of solvent. The solvent may be water, in which case the solvate may be a hydrate. Alternatively, the solvent may be an organic solvent. Thus, the compounds of the embodiments disclosed herein may exist as a hydrate, including a monohydrate, dihydrate, hemihydrate, sesquihydrate, trihydrate, tetrahydrate and the like, as well as the corresponding solvated forms. The compounds of the embodiments disclosed herein may be true solvates, while in other cases, a compound of the embodiments disclosed herein may merely retain adventitious water or be a mixture of water plus some adventitious solvent. In any of the embodiments disclosed herein, compounds disclosed herein may be in the form of a solvate thereof.

A "pharmaceutical composition" refers to a formulation of a compound of the embodiments disclosed herein and a medium generally accepted in the art for the delivery of the biologically active compound to mammals, e.g., humans. Such a medium includes all pharmaceutically acceptable excipients.

"Effective amount" or "therapeutically effective amount" refers to an amount of a compound according to the embodiments disclosed herein, which when administered to a patient in need thereof, is sufficient to effect treatment of disease-states, conditions, or disorders disclosed herein. Such an amount would be sufficient to elicit the biological or medical response of a tissue system, or patient that is sought by a researcher or clinician. The amount of a compound according to the embodiments disclosed herein which constitutes a therapeutically effective amount will vary depending on such factors as the compound and its biological activity, the composition used for administration, the time of administration, the route of administration, the rate of excretion of the compound, the duration of the treatment, the type of disease-state or disorder being treated and its severity, drugs used in combination with or coincidentally with the compounds of the embodiments disclosed herein, and the age, body weight, general health, sex and diet of the patient. Such a therapeutically effective amount can be determined routinely by one of ordinary skill in the art having regard to their own knowledge, the state of the art, and this disclosure.

The term "treatment" as used herein is intended to mean the administration of a compound or composition according to the present embodiments disclosed herein to alleviate or eliminate symptoms of HIV infection and/or to reduce viral load in a patient. The term "treatment" also encompasses the administration of a compound or composition according to the present embodiments disclosed herein post-exposure of the individual to the virus but before the appearance of symptoms of the disease, and/or prior to the detection of the virus in the blood, to prevent the appearance of symptoms of the disease and/or to prevent the virus from reaching detectable levels in the blood, and the administration of a compound or composition according to the present embodiments disclosed hereinto prevent perinatal transmission of HIV from mother to baby, by administration to the mother before giving birth and to the child within the first days of life. The term "treatment" also encompasses the administration of a compound or composition according to the present embodiments disclosed herein before the exposure of the individual to the virus (also called pre-exposure prophylaxis or PrEP), to prevent HIV infection from taking hold if the individual is exposed to the virus and/or to keep the virus from establishing a permanent infection and/or to prevent the appearance of symptoms of the disease and/or to prevent the virus from reaching detectable levels in the blood. The term "treatment" also encompasses the administration of a compound or composition according to the present embodiments disclosed herein both before and after the exposure of the individual to the virus.

The term "antiviral agent" as used herein is intended to mean an agent (compound or biological) that is effective to inhibit the formation and/or replication of a virus in a human being, including but not limited to agents that interfere with either host or viral mechanisms necessary for the formation and/or replication of a virus in a human being.

The term "inhibitor of HIV replication" as used herein is intended to mean an agent capable of reducing or eliminating the ability of HIV to replicate in a host cell, whether in vitro, ex vivo or in vivo.

The compounds of the embodiments disclosed herein, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present disclosure is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centres of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present disclosure contemplates various stereoisomers and mixtures thereof and includes "enantiomers", which refers to two stereoisomers whose molecules are non-superimposable mirror images of one another. In any of the embodiments disclosed herein, compounds disclosed herein may be in the form of a stereoisomer thereof.

A "tautomer" refers to a proton shift from one atom of a molecule to another atom of the same molecule. The present disclosure includes tautomers of any said compounds.

"Partially unsaturated" refers for a cyclic group to a cyclic group which contains at least one double bond but is not aromatic.

A "prodrug" is a biologically inactive derivative of a drug that upon administration to the human body is converted to the biologically active parent drug according to some chemical or enzymatic pathway.

Compounds

As noted above, in one embodiment, compounds are provided having the following Formula (Ia):

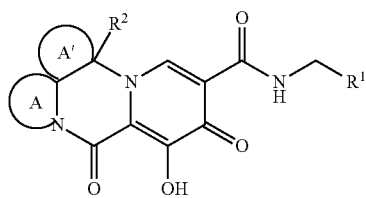

(Ia)

or a pharmaceutically acceptable salt thereof, wherein:

A is a 4 to 7 membered monocyclic heterocyclyl saturated or partially unsaturated and optionally substituted with 1 to 5 $R^3$ groups;

each $R^3$ is independently selected from the group consisting of $C_{1-4}$alkyl, halogen and oxo; or two $R^3$ connected to the same or adjacent carbon atoms form a spiro or fused $C_{3-6}$cycloalkyl or 4 to 6 membered heterocyclyl ring;

A' is selected from the group consisting of $C_{3-7}$ monocyclic cycloalkyl and 4 to 7 membered monocyclic heterocyclyl; wherein each $C_{3-7}$ monocyclic cycloalkyl and 4 to 7 membered monocyclic heterocyclyl is optionally substituted with 1 to 5 $R^4$ groups;

each $R^4$ is independently selected from the group consisting of $C_{1-4}$alkyl, halogen and oxo; or two $R^4$ connected to the same or adjacent carbon atoms form a spiro or fused $C_{3-6}$cycloalkyl or 4 to 6 membered heterocyclyl ring;

$R^1$ is phenyl optionally substituted with 1 to 5 $R^5$ groups;

each $R^5$ is independently selected from the group consisting of halogen and $C_{1-3}$alkyl; and $R^2$ is selected from the group consisting of H, $C_{1-3}$haloalkyl and $C_{1-4}$alkyl.

In another embodiment, A is a 5 or 6 membered monocyclic heterocyclyl saturated or partially unsaturated and optionally substituted with 1 to 5 $R^3$ groups.

In another embodiment, A is a 5 membered monocyclic heterocyclyl saturated or partially unsaturated and optionally substituted with 1 to 5 $R^3$ groups.

In another embodiment, A is a 6 membered monocyclic heterocyclyl saturated or partially unsaturated and optionally substituted with 1 to 5 $R^3$ groups.

In another embodiment, A is selected from the group consisting of oxazolidinyl, piperidinyl, 3,4-unsaturated piperidinyl, pyrrolidinyl, tetrahydro-1,3-oxazinyl and thiazolidinyl; each of which is optionally substituted with 1 to 5 $R^3$ groups.

In another embodiment, A is selected from the group consisting of oxazolidinyl, pyrrolidinyl, and thiazolidinyl; each of which is optionally substituted with 1 to 5 $R^3$ groups.

In another embodiment, A is selected from the group consisting of piperidinyl, tetrahydro-1,3-oxazinyl and 3,4-unsaturated piperidinyl; each of which is optionally substituted with 1 to 5 $R^3$ groups.

In another embodiment, A is piperidinyl optionally substituted with 1 to 5 $R^3$ groups.

In another embodiment, A is selected from the group consisting of oxazolidinyl, piperidinyl, 3,4-unsaturated piperidinyl, pyrrolidinyl, tetrahydro-1,3-oxazinyl and thiazolidinyl; each of which is optionally substituted with one or two $R^3$ groups; wherein $R^3$ is $C_{1-4}$alkyl; or two $R^3$ connected to the same or adjacent carbon atoms form a spiro or fused $C_{3-6}$cycloalkyl or 4 to 6 membered heterocyclyl ring.

In another embodiment, A is selected from the group consisting of oxazolidinyl, pyrrolidinyl, and thiazolidinyl; each of which is optionally substituted with one or two $R^3$ groups; wherein $R^3$ is $C_{1-4}$alkyl; or two $R^3$ connected to the same or adjacent carbon atoms form a spiro or fused $C_{3-6}$cycloalkyl or 4 to 6 membered heterocyclyl ring.

In another embodiment, A is selected from the group consisting of piperidinyl, tetrahydro-1,3-oxazinyl and 3,4-unsaturated piperidinyl; each of which is optionally substituted with one or two $R^3$ groups; wherein $R^3$ is $C_{1-4}$alkyl; or two $R^3$ connected to the same or adjacent carbon atoms form a spiro or fused $C_{3-6}$cycloalkyl or 4 to 6 membered heterocyclyl ring.

In another embodiment, A is piperidinyl optionally substituted with one or two $R^3$ groups; wherein $R^3$ is $C_{1-4}$alkyl; or two $R^3$ connected to the same or adjacent carbon atoms form a spiro or fused $C_{3-6}$cycloalkyl or 4 to 6 membered heterocyclyl ring.

In another embodiment, A is selected from the group consisting of oxazolidinyl, piperidinyl, 3,4-unsaturated piperidinyl, pyrrolidinyl, tetrahydro-1,3-oxazinyl and thiazolidinyl; each of which is optionally substituted with methyl.

In another embodiment, A is piperidinyl optionally substituted with methyl.

In another embodiment, A is piperidinyl.

In another embodiment,

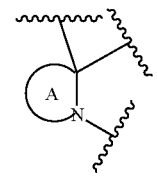

is selected from the group consisting of:

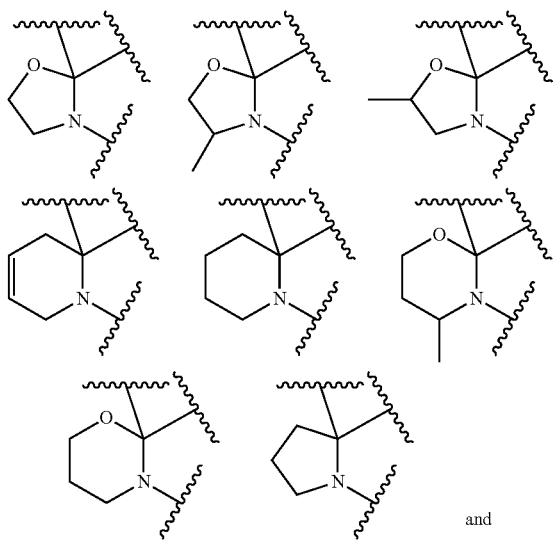

and

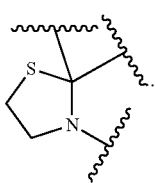
In another embodiment,
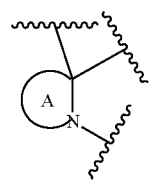
is selected from the group consisting of:
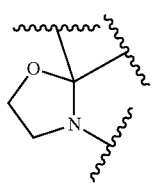 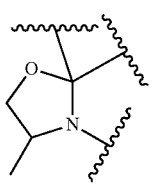 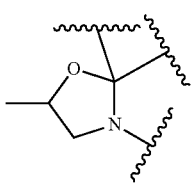
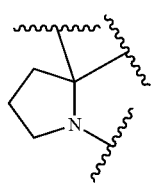 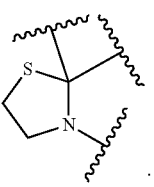
and
In another embodiment,
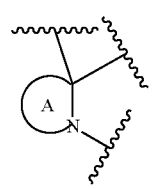
is selected from the group consisting of:
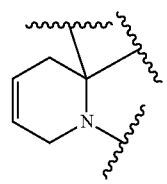 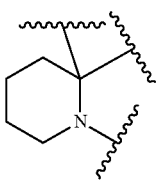
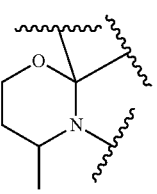 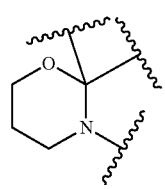
and
In another embodiment,
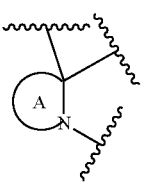
is
In another embodiment,
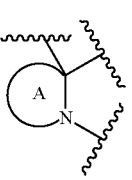
is selected from the group consisting of:
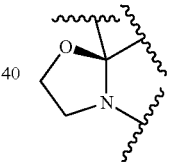 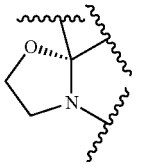 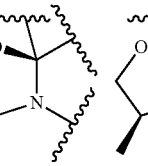
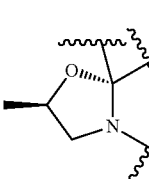 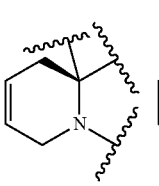 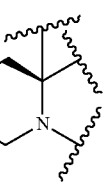
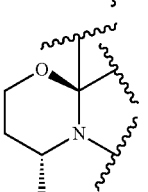 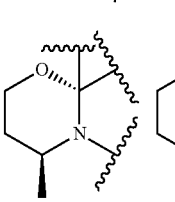 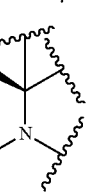
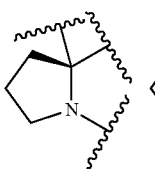 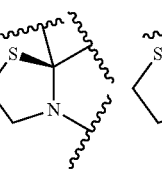 

-continued

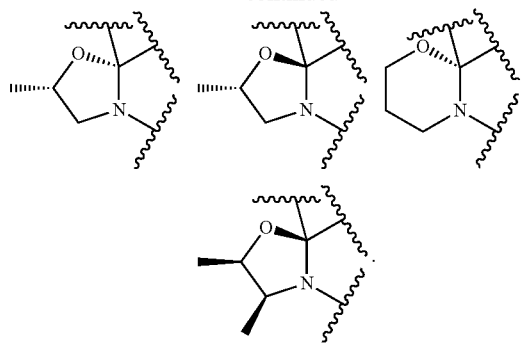
and

In another embodiment,

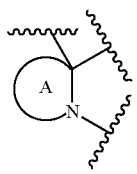

is selected from the group consisting of:

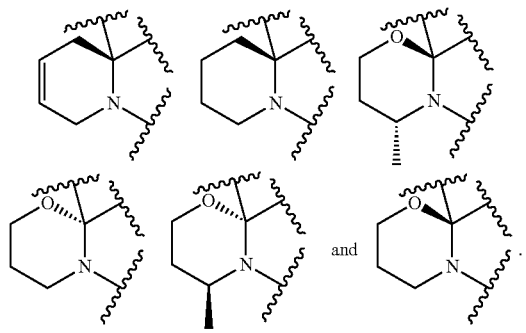
and

In another embodiment,

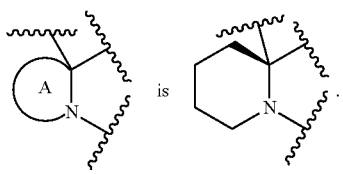

In another embodiment,

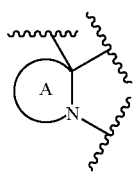

is selected from the group consisting of:

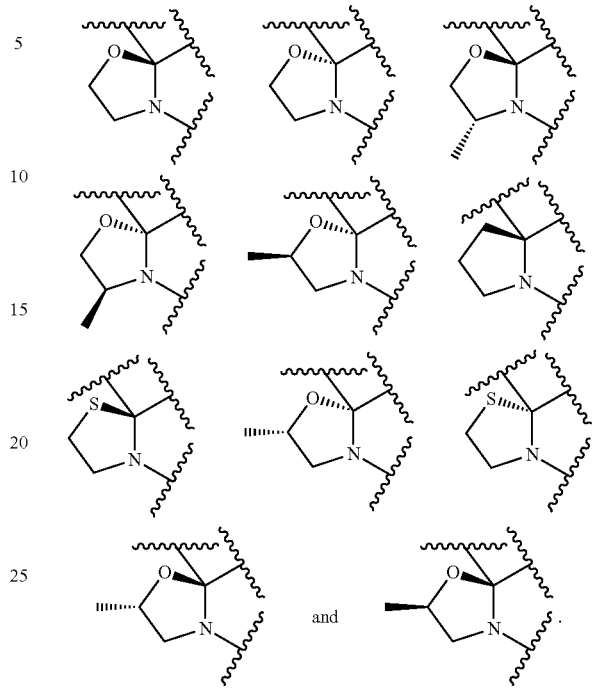
and

In another embodiment, A' is selected from the group consisting of $C_{4-6}$ monocyclic cycloalkyl and 5 to 6 membered monocyclic heterocyclyl; wherein each $C_{4-6}$ monocyclic cycloalkyl and 5 to 6 membered monocyclic heterocyclyl is optionally substituted with 1 to 5 $R^4$ groups.

In another embodiment, A' is selected from the group consisting of $C_{5-6}$ monocyclic cycloalkyl and 5 to 6 membered monocyclic heterocyclyl; wherein each $C_{5-6}$ monocyclic cycloalkyl and 5 to 6 membered monocyclic heterocyclyl is optionally substituted with 1 to 5 $R^4$ groups.

In another embodiment, A' is selected from the group consisting of cyclopentyl, tetrahydrofuranyl, cyclohexyl and tetrahydropyranyl; each of which is optionally substituted with 1 to 5 $R^4$ groups.

In another embodiment, A' is selected from the group consisting of cyclopentyl and cyclohexyl; each of which is optionally substituted with 1 to 5 $R^4$ groups.

In another embodiment, A' is selected from the group consisting of tetrahydropyranyl and tetrahydrofuranyl; each of which is optionally substituted with 1 to 5 $R^4$ groups.

In another embodiment, A' is tetrahydrofuranyl optionally substituted with 1 to 5 $R^4$ groups.

In another embodiment, A' is tetrahydropyranyl optionally substituted with 1 to 5 $R^4$ groups.

In another embodiment, A' is selected from the group consisting of cyclopentyl, tetrahydrofuranyl, cyclohexyl and tetrahydropyranyl; each of which is optionally substituted with one or two $R^4$ groups, wherein each $R^4$ is independently selected from the group consisting of $C_{1-4}$alkyl, halogen and oxo; or two $R^2$ connected to the same or adjacent carbon atoms form a spiro or fused $C_{3-6}$cycloalkyl or 4 to 6 membered heterocyclyl ring.

In another embodiment, A' is selected from the group consisting of cyclopentyl, and cyclohexyl; each of which is optionally substituted with one or two $R^4$ groups, wherein each $R^4$ is independently selected from the group consisting of $C_{1-4}$alkyl, halogen and oxo; or two $R^2$ connected to the same or adjacent carbon atoms form a spiro or fused $C_{3-6}$cycloalkyl or 4 to 6 membered heterocyclyl ring.

In another embodiment, A' is selected from the group consisting of tetrahydropyranyl and tetrahydrofuranyl; each of which is optionally substituted with one or two $R^4$ groups, wherein each $R^4$ is independently selected from the group consisting of $C_{1-4}$alkyl, halogen and oxo; or two $R^2$ connected to the same or adjacent carbon atoms form a spiro or fused $C_{3-6}$cycloalkyl or 4 to 6 membered heterocyclyl ring.

In another embodiment, A' is tetrahydropyranyl optionally substituted with one or two $R^4$ groups, wherein each $R^4$ is independently selected from the group consisting of $C_{1-4}$alkyl, halogen and oxo; or two $R^2$ connected to the same or adjacent carbon atoms form a spiro or fused $C_{3-6}$cycloalkyl or 4 to 6 membered heterocyclyl ring.

In another embodiment, A' is tetrahydrofuranyl optionally substituted with one or two $R^4$ groups, wherein each $R^4$ is independently selected from the group consisting of $C_{1-4}$alkyl, halogen and oxo; or two $R^2$ connected to the same or adjacent carbon atoms form a spiro or fused $C_{3-6}$cycloalkyl or 4 to 6 membered heterocyclyl ring.

In another embodiment, A' is selected from the group consisting of cyclopentyl, tetrahydrofuranyl, cyclohexyl and tetrahydropyranyl; each of which is optionally fused with a $C_{3-6}$cycloalkyl ring.

In another embodiment, A' is cyclopentyl optionally fused with a $C_{3-6}$cycloalkyl ring.

In another embodiment, A' is selected from the group consisting of tetrahydrofuranyl and tetrahydropyranyl; each of which is optionally fused with a $C_{3-6}$cycloalkyl ring.

In another embodiment, A' is tetrahydrofuranyl optionally fused with a $C_{3-6}$cycloalkyl ring.

In another embodiment, A' is tetrahydropyranyl optionally fused with a $C_{3-6}$cycloalkyl ring.

In another embodiment, A' is selected from the group consisting of cyclopentyl, tetrahydrofuranyl, cyclohexyl and tetrahydropyranyl; each of which is optionally fused with a cyclopropyl group.

In another embodiment, A' is cyclopentyl optionally fused with a cyclopropyl group.

In another embodiment, A' is selected from the group consisting of tetrahydrofuranyl and tetrahydropyranyl; each of which is optionally fused with a cyclopropyl group.

In another embodiment, A' is tetrahydrofuranyl optionally fused with a cyclopropyl group.

In another embodiment, A' is tetrahydrofuranyl.

In another embodiment, A' is tetrahydropyranyl optionally fused with a cyclopropyl group.

In another embodiment, A' is tetrahydropyranyl.

In another embodiment, A' is selected from the group consisting of tetrahydrofuranyl and tetrahydropyranyl, and A is piperidinyl.

In another embodiment, A' is tetrahydrofuranyl and A is piperidinyl.

In another embodiment, A' is tetrahydropyranyl, and A is piperidinyl.

In another embodiment, $R^2$ is H.

In another embodiment, A' is selected from the group consisting of tetrahydrofuranyl and tetrahydropyranyl, and $R^2$ is H.

In another embodiment, A' is selected from the group consisting of tetrahydrofuranyl and tetrahydropyranyl, A is piperidinyl, and $R^2$ is H.

In another embodiment, A' is tetrahydrofuranyl, A is piperidinyl, and $R^2$ is H.

In another embodiment, A' is tetrahydropyranyl, A is piperidinyl, and $R^2$ is H.

In another embodiment,

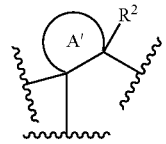

is selected from the group consisting of:

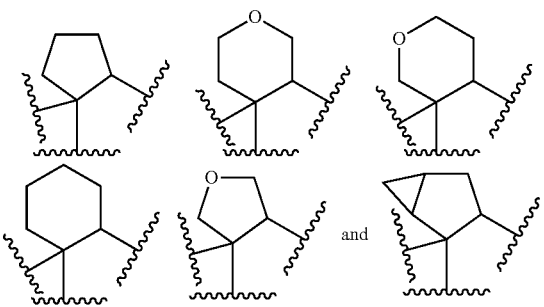

In another embodiment,

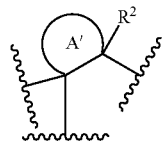

is selected from the group consisting of:

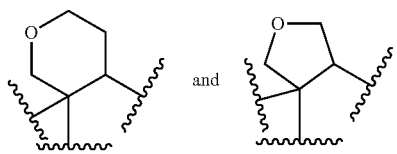

In another embodiment,

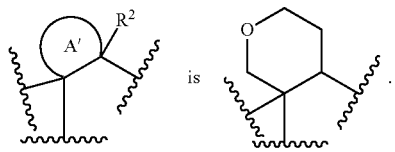

is

In another embodiment,

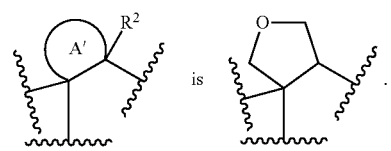

is

In another embodiment,
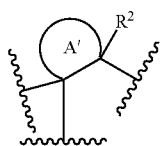
is selected from the group consisting of:
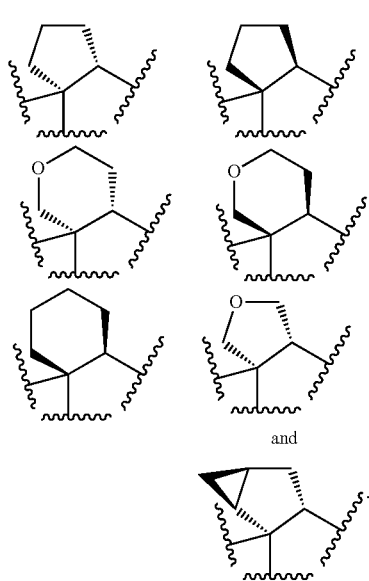
In another embodiment,
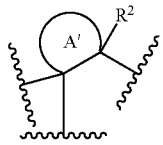
is selected from the group consisting of:
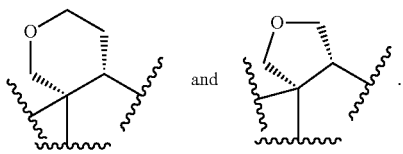
In another embodiment,
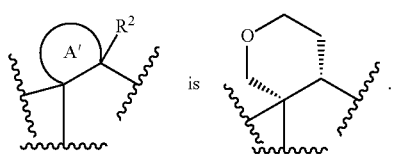
In another embodiment,
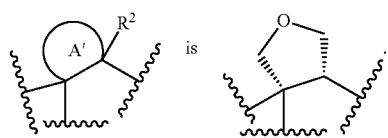 is 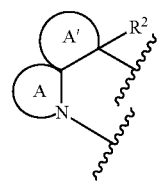.
In another embodiment,
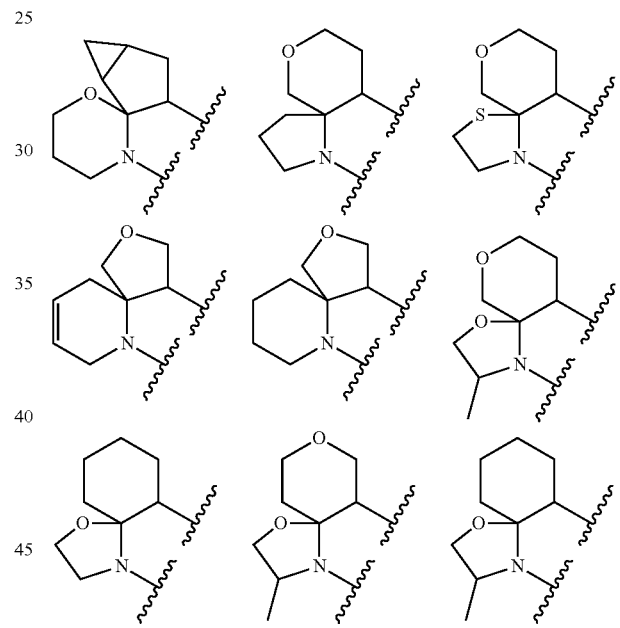
is selected from the group consisting of:
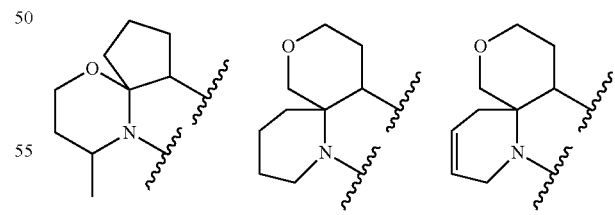
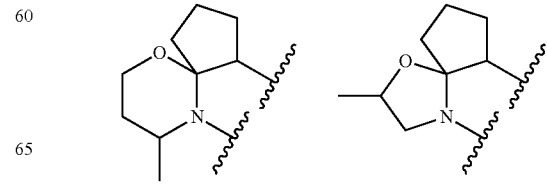

-continued
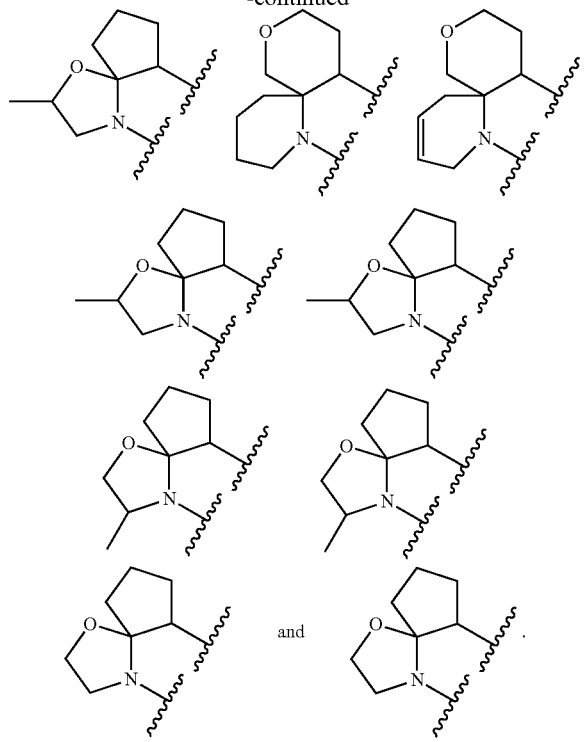
In another embodiment,
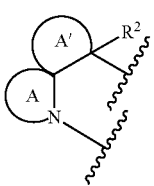 is 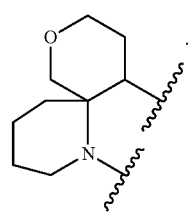.
In another embodiment,
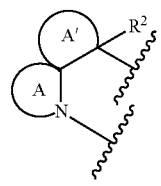
is selected from the group consisting of:
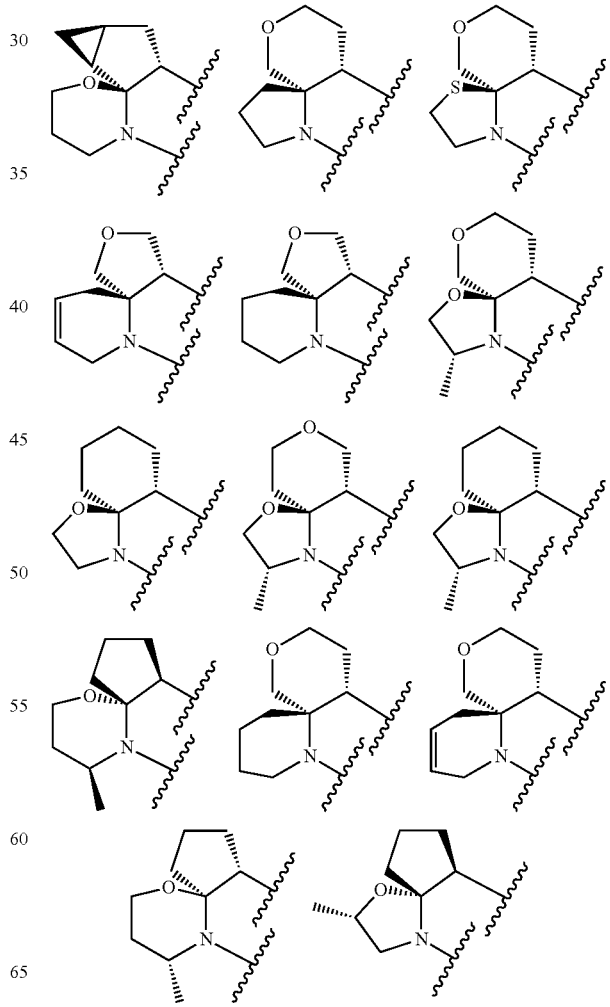
In another embodiment,
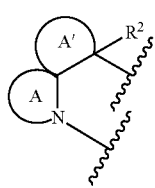
is selected from the group consisting of:
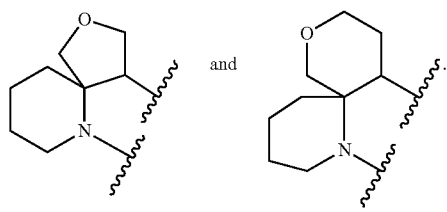 [SMILES: *C1COCC12CCCCN2* ; *C1CCOCC12CCCCN2*]
In another embodiment,
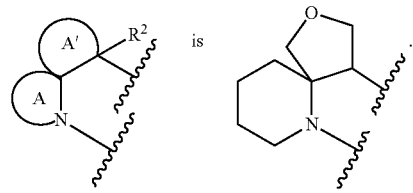

-continued

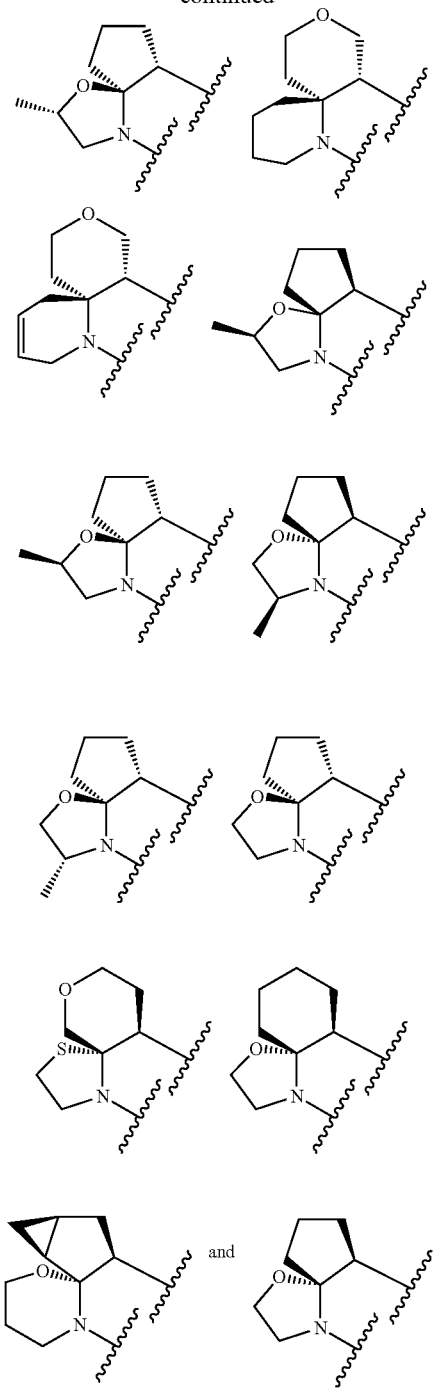

In another embodiment, is selected from the group consisting of:

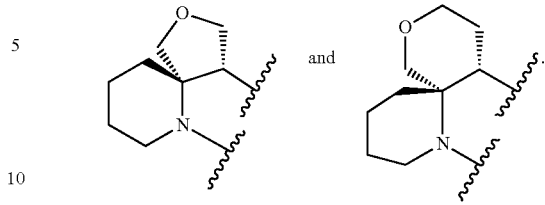

In another embodiment,

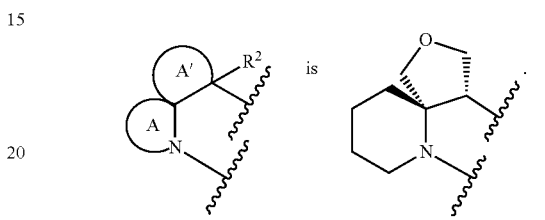 is 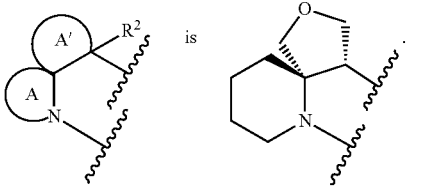

In another embodiment,

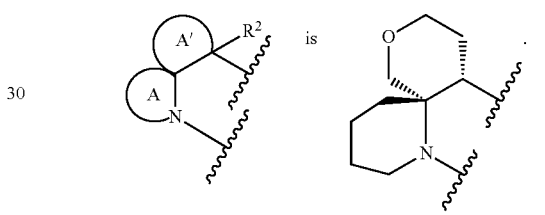 is 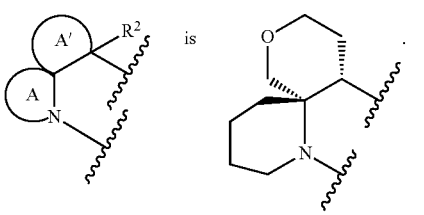

In another embodiment, R$^1$ is phenyl substituted with two or three R$^5$ groups, wherein each R$^5$ is independently selected from the group consisting of halogen and C$_{1-3}$alkyl.

In another embodiment, R$^1$ is phenyl substituted with two or three R$^5$ groups, wherein each R$^5$ is independently selected from the group consisting of fluoro and chloro.

In another embodiment, R$^1$ is selected from the group consisting of:

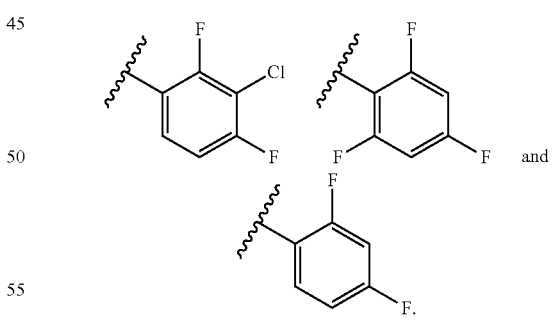

In another embodiment, R$^1$ is

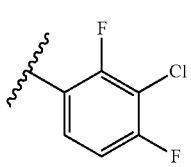

In another embodiment, compounds are provided having the following Formula (Ia):

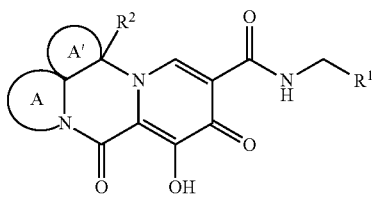

(Ia)

or a pharmaceutically acceptable salt thereof, wherein:

A is selected from the group consisting of oxazolidinyl, piperidinyl, 3,4-unsaturated piperidinyl, pyrrolidinyl, tetrahydro-1,3-oxazinyl and thiazolidinyl; each of which is optionally substituted with 1 to 5 $R^3$ groups;

each $R^3$ is independently selected from the group consisting of $C_{1-4}$alkyl, halogen and oxo; or two $R^3$ connected to the same or adjacent carbon atoms form a spiro or fused $C_{3-6}$cycloalkyl or 4 to 6 membered heterocyclyl ring;

A' is selected from the group consisting of cyclopentyl, tetrahydrofuranyl, cyclohexyl and tetrahydropyranyl; each of which is optionally substituted with 1 to 5 $R^4$ groups;

each $R^4$ is independently selected from the group consisting of $C_{1-4}$alkyl, halogen and oxo; or two $R^4$ connected to the same or adjacent carbon atoms form a spiro or fused $C_{3-6}$cycloalkyl or 4 to 6 membered heterocyclyl ring;

$R^1$ is phenyl substituted with two or three $R^5$ groups, wherein each $R^5$ is independently selected from the group consisting of halogen and $C_{1-3}$alkyl; and $R^2$ is selected from the group consisting of H, $C_{1-3}$haloalkyl and $C_{1-4}$alkyl.

In another embodiment, compounds are provided having the following Formula (Ia):

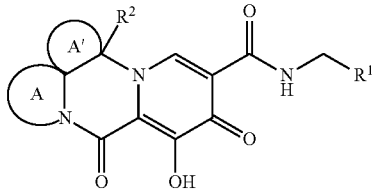

(Ia)

or a pharmaceutically acceptable salt thereof, wherein:

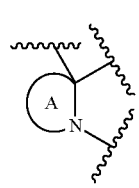

is selected from the group consisting of:

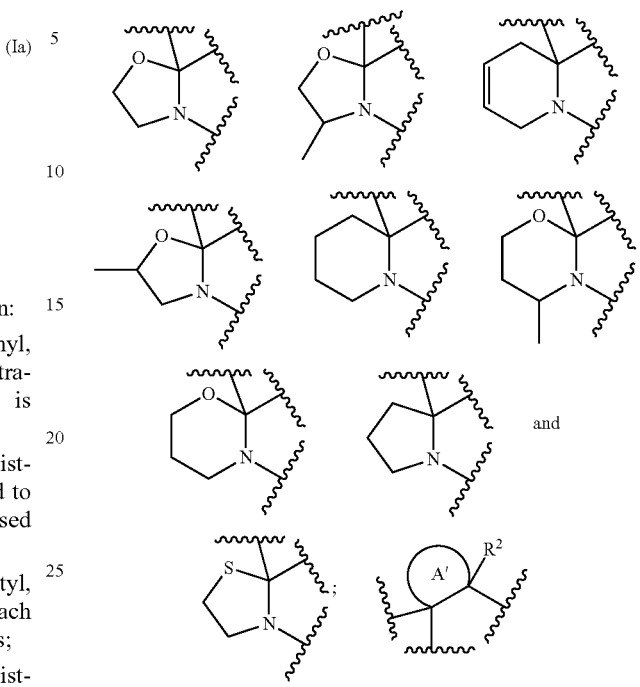

is selected from the group consisting of:

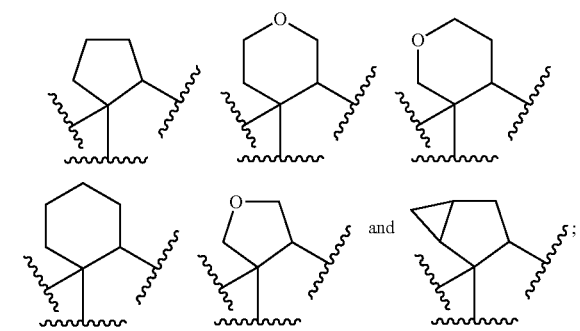

and $R^1$ is phenyl substituted with two or three $R^5$ groups, wherein each $R^5$ is independently selected from the group consisting of fluoro and chloro.

In another embodiment, compounds are provided having the following structures:

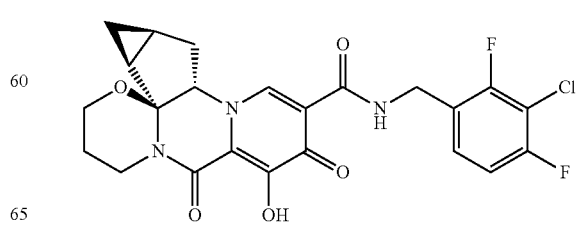

25
-continued
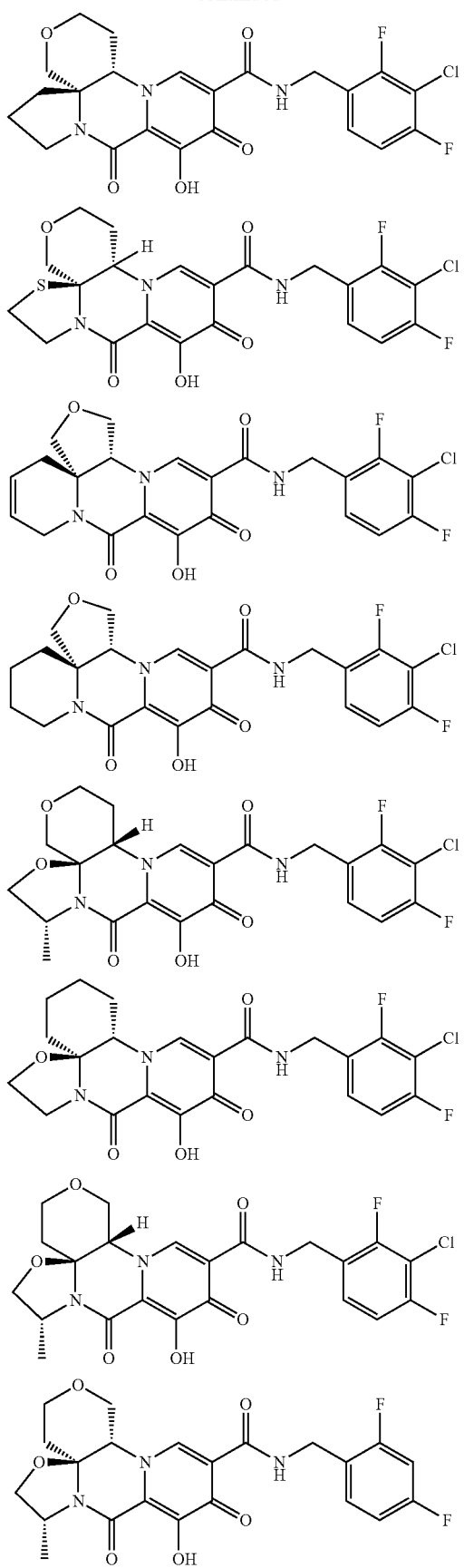
26
-continued
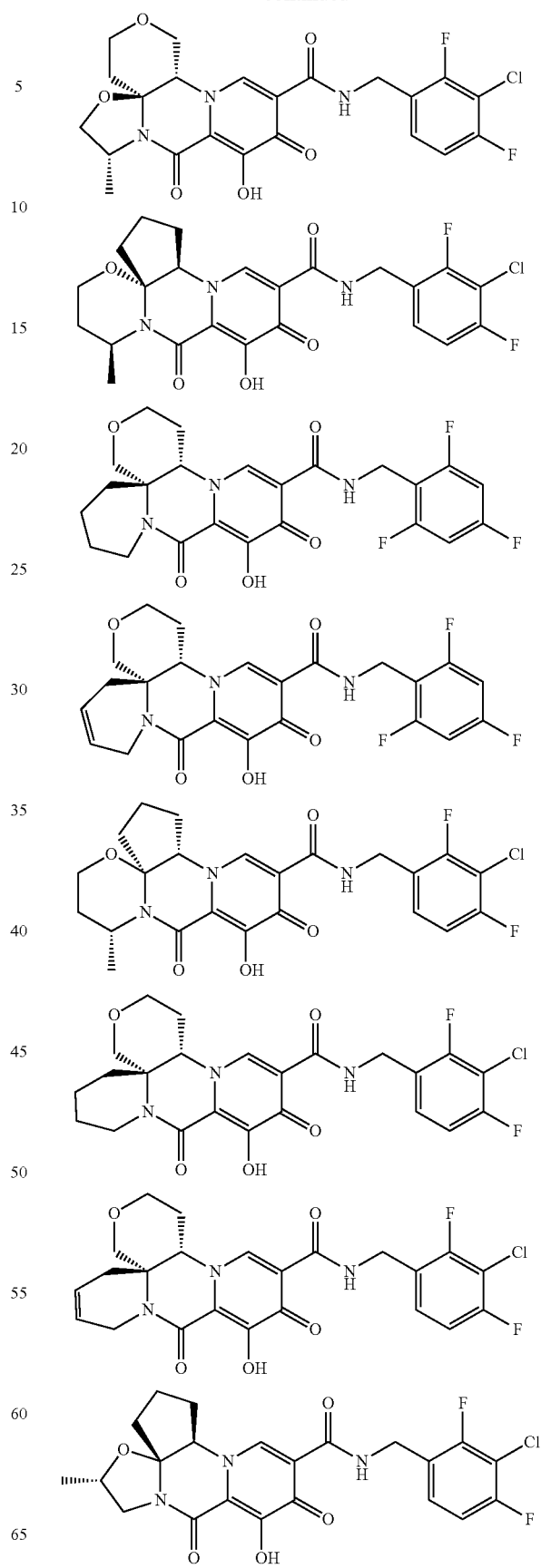

27
-continued
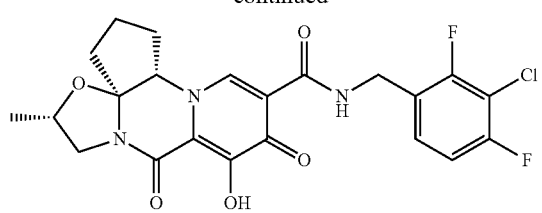
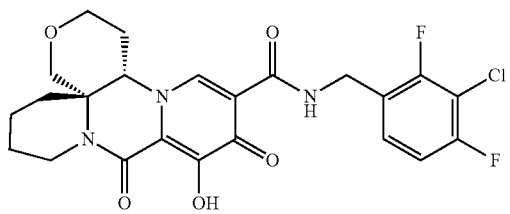
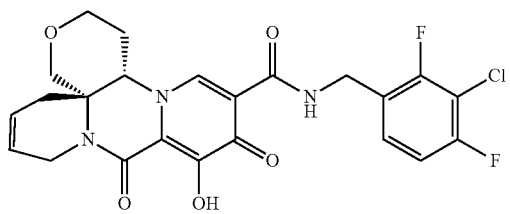
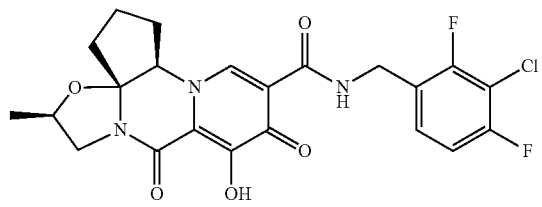
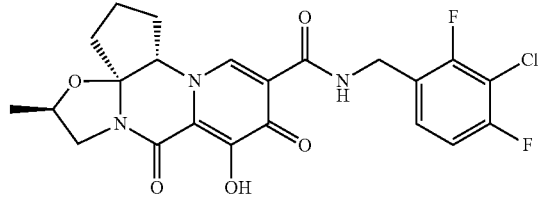
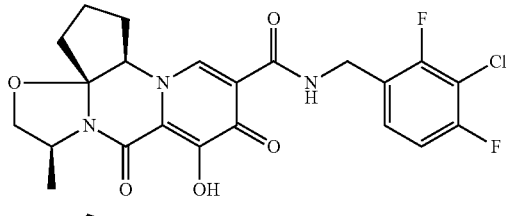
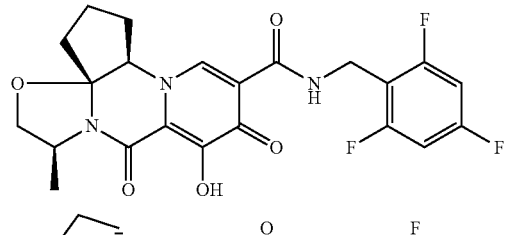
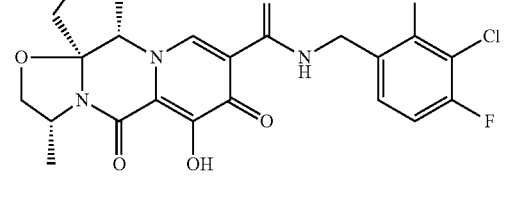
28
-continued
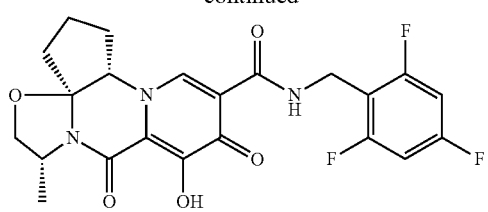
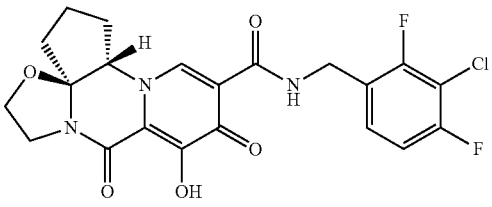
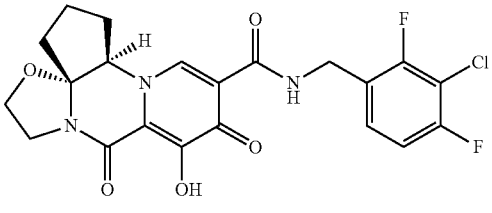
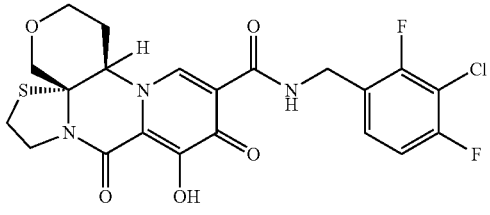
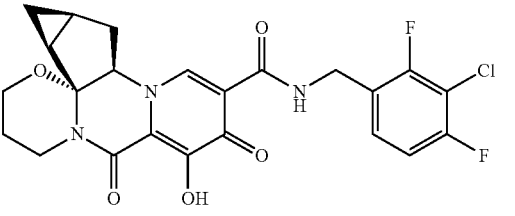
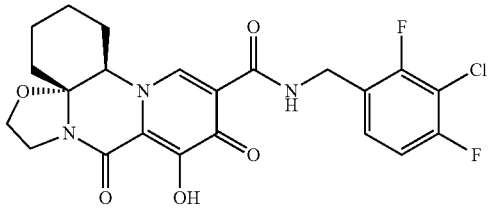
or a pharmaceutically acceptable salt thereof.
In another embodiment, compounds are provided having the following structures:
(II)
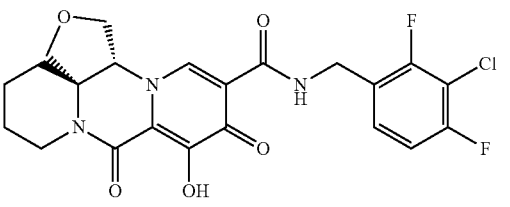
and -continued

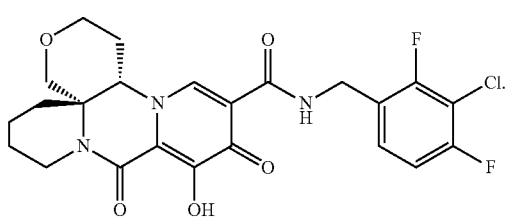

(III)

or a pharmaceutically acceptable salt thereof.

In another embodiment, a compound is provided having the following structure:

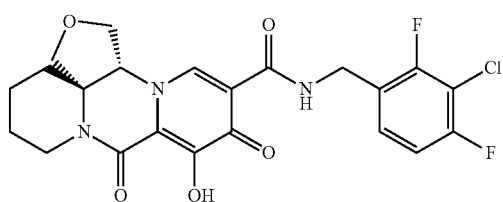

(II)

or a pharmaceutically acceptable salt thereof.

In another embodiment, a compound is provided having the following structure:

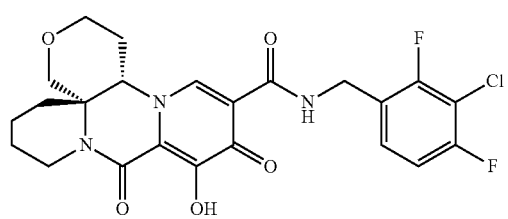

(III)

or a pharmaceutically acceptable salt thereof.

In another embodiment, a pharmaceutical composition is provided comprising a compound having the Formula (Ia), (II) or (III) or a pharmaceutically acceptable salt thereof, and a pharmaceutically acceptable excipient.

In another embodiment, the pharmaceutical composition further comprises one or more additional therapeutic agents.

In another embodiment, the pharmaceutical composition further comprises one or more anti-HIV agent.

In another embodiment, the pharmaceutical composition further comprises one or more additional therapeutic agents selected from the group consisting of HIV protease inhibitors, HIV non-nucleoside inhibitors of reverse transcriptase, HIV nucleoside or nucleotide inhibitors of reverse transcriptase, HIV non-catalytic site integrase inhibitors, HIV capsid inhibitors, and combinations thereof.

In another embodiment, the pharmaceutical composition further comprises one or more additional therapeutic agents selected from the group consisting of HIV protease inhibitors, HIV non-nucleoside inhibitors of reverse transcriptase, HIV nucleoside or nucleotide inhibitors of reverse transcriptase, and combinations thereof.

In another embodiment, the pharmaceutical composition further comprises a first additional therapeutic agent selected from the group consisting of: abacavir sulfate, tenofovir, tenofovir disoproxil, tenofovir disoproxil fumarate, tenofovir alafenamide, and tenofovir alafenamide hemifumarate and a second additional therapeutic agent selected from the group consisting of emtricitabine and lamivudine.

In another embodiment, the pharmaceutical composition further comprises a first additional therapeutic agent selected from the group consisting of: tenofovir disoproxil, tenofovir disoproxil fumarate, tenofovir alafenamide, and tenofovir alafenamide hemifumarate, and emtricitabine.

In another embodiment, the pharmaceutical composition further comprises tenofovir disoproxil fumarate and emtricitabine.

In another embodiment, the pharmaceutical composition further comprises tenofovir alafenamide hemifumarate and emtricitabine.

In another embodiment, a method of treating an HIV infection in a human having or at risk of having the infection by administering to the human a therapeutically effective amount of a compound of Formula (Ia), (II) or (III) or a pharmaceutically acceptable salt thereof, or a pharmaceutical composition of a compound of Formula (Ia), (II) or (III) or a pharmaceutically acceptable salt thereof, is provided.

In another embodiment, the method of treating an HIV infection in a human having or at risk of having the infection, further comprises administering to the human a therapeutically effective amount of one or more additional therapeutic agents.

In another embodiment, the method of treating an HIV infection in a human having or at risk of having the infection, further comprises administering to the human a therapeutically effective amount of one or more additional therapeutic agents selected from the group consisting of HIV protease inhibitors, HIV non-nucleoside inhibitors of reverse transcriptase, HIV nucleoside or nucleotide inhibitors of reverse transcriptase, HIV non-catalytic site integrase inhibitors, HIV capsid inhibitors, and combinations thereof.

In another embodiment, the method of treating an HIV infection in a human having or at risk of having the infection, further comprises administering to the human a therapeutically effective amount of one or more additional therapeutic agents selected from the group consisting of HIV protease inhibitors, HIV non-nucleoside inhibitors of reverse transcriptase, HIV nucleoside or nucleotide inhibitors of reverse transcriptase, and combinations thereof. In a specific embodiment, the method of treating an HIV infection in a human having or at risk of having the infection, further comprises administering to the human a therapeutically effective amount of HIV non-nucleoside inhibitors of reverse transcriptase.

In another embodiment, the method of treating an HIV infection in a human having or at risk of having the infection, further comprises administering to the human a therapeutically effective amount of a first additional therapeutic agent selected from the group consisting of: abacavir sulfate, tenofovir, tenofovir disoproxil, tenofovir disoproxil fumarate, tenofovir alafenamide, and tenofovir alafenamide hemifumarate and a second additional therapeutic agent selected from the group consisting of emtricitabine and lamivudine.

In another embodiment, the method of treating an HIV infection in a human having or at risk of having the infection, comprises administering simultaneously to the human a compound of Formula (Ia), (II) or (III) or a pharmaceutically acceptable salt thereof, with a first additional therapeutic agent selected from the group consisting of: abacavir sulfate, tenofovir, tenofovir disoproxil, tenofovir disoproxil fumarate, tenofovir alafenamide, and tenofovir alafenamide hemifumarate and a second additional therapeutic agent selected from the group consisting of emtricitabine and lamivudine.

In another embodiment, the method of treating an HIV infection in a human having or at risk of having the infection, comprises administering to the human a fixed dose combination of a compound of Formula (Ia), (II) or (III) or a pharmaceutically acceptable salt thereof, with a first additional therapeutic agent selected from the group consisting of: abacavir sulfate, tenofovir, tenofovir disoproxil, tenofovir disoproxil fumarate, tenofovir alafenamide, and tenofovir alafenamide hemifumarate and a second additional therapeutic agent selected from the group consisting of emtricitabine and lamivudine.

In another embodiment, the method of treating an HIV infection in a human having or at risk of having the infection, comprises administering to the human a unitary dosage form for simultaneous administration to a patient, for example as a solid dosage form for oral administration, of a compound of Formula (Ia), (II) or (III) or a pharmaceutically acceptable salt thereof, with a first additional therapeutic agent selected from the group consisting of: abacavir sulfate, tenofovir, tenofovir disoproxil, tenofovir disoproxil fumarate, tenofovir alafenamide, and tenofovir alafenamide hemifumarate and a second additional therapeutic agent selected from the group consisting of emtricitabine and lamivudine.

In another embodiment, the method of treating an HIV infection in a human having or at risk of having the infection, further comprises administering to the human a therapeutically effective amount of tenofovir disoproxil and emtricitabine.

In another embodiment, the method of treating an HIV infection in a human having or at risk of having the infection, further comprises administering to the human a therapeutically effective amount of tenofovir alafenamide and emtricitabine.

In another embodiment, a use of a compound of Formula (Ia), (II) or (III), or a pharmaceutically acceptable salt thereof, or a pharmaceutical composition of a compound of (Ia), (II) or (III) or a pharmaceutically acceptable salt thereof, for the treatment of an HIV infection in a human having or at risk of having the infection is provided.

In another embodiment, a compound of Formula (Ia), (II) or (III), or a pharmaceutically acceptable salt thereof, or a pharmaceutical composition of a compound of Formula (Ia), (II) or (III) or a pharmaceutically acceptable salt thereof, for use in medical therapy is provided.

In another embodiment, a compound of Formula (Ia), (II) or (III), or a pharmaceutically acceptable salt thereof, or a pharmaceutical composition of a compound of Formula (Ia), (II) or (III) or pharmaceutically acceptable salt thereof, for use in the prophylactic or therapeutic treatment of an HIV infection is provided.

In another embodiment, a compound of Formula (Ia), (II) or (III) or a pharmaceutically acceptable salt thereof, or a pharmaceutical composition of a compound of Formula (Ia), (II) or (III) or a pharmaceutically acceptable salt thereof for use in a method of treating an HIV infection in a human having or at risk of having the infection, is provided.

In another embodiment, a compound of Formula (Ia), (II) or (III) or a pharmaceutically acceptable salt thereof, or a pharmaceutical composition of a compound of Formula (Ia), (II) or (III) or a pharmaceutically acceptable salt thereof for use in a method of treating an HIV infection in a human having or at risk of having the infection, is provided wherein said method further comprises administering to the human one or more additional therapeutic agents.

In another embodiment, a compound of Formula (Ia), (II) or (III) or a pharmaceutically acceptable salt thereof, or a pharmaceutical composition of a compound of Formula (Ia), (II) or (III) or a pharmaceutically acceptable salt thereof for use in a method of treating an HIV infection in a human having or at risk of having the infection, is provided wherein said method further comprises administering to the human one or more additional therapeutic agents selected from the group consisting of HIV protease inhibitors, HIV non-nucleoside inhibitors of reverse transcriptase, HIV nucleoside or nucleotide inhibitors of reverse transcriptase, HIV non-catalytic site integrase inhibitors, HIV capsid inhibitors, and combinations thereof. In one embodiment the one or more additional therapeutic agents is selected from the group consisting of HIV protease inhibitors, HIV non-nucleoside inhibitors of reverse transcriptase, HIV nucleoside or nucleotide inhibitors of reverse transcriptase, and combinations thereof. In one embodiment, the one or more additional therapeutic agents is an HIV non-nucleoside inhibitor of reverse transcriptase.

In another embodiment, a compound of Formula (Ia), (II) or (III) or a pharmaceutically acceptable salt thereof, or a pharmaceutical composition of a compound of Formula (Ia), (II) or (III) or a pharmaceutically acceptable salt thereof for use in a method of treating an HIV infection in a human having or at risk of having the infection, is provided wherein said method further comprises administering to the human a first additional therapeutic agent selected from the group consisting of: abacavir sulfate, tenofovir, tenofovir disoproxil, tenofovir disoproxil fumarate, tenofovir alafenamide, and tenofovir alafenamide hemifumarate and a second additional therapeutic agent selected from the group consisting of emtricitabine and lamivudine. In one embodiment, said method comprises administering simultaneously to the human said compound of Formula (Ia), (II) or (III) or a pharmaceutically acceptable salt thereof, with said first additional therapeutic agent selected from the group consisting of: abacavir sulfate, tenofovir, tenofovir disoproxil, tenofovir disoproxil fumarate, tenofovir alafenamide, and tenofovir alafenamide hemifumarate and a second additional therapeutic agent selected from the group consisting of emtricitabine and lamivudine.

In another embodiment, a compound of Formula (Ia), (II) or (III) or a pharmaceutically acceptable salt thereof, or a pharmaceutical composition of a compound of Formula (Ia), (II) or (III) or a pharmaceutically acceptable salt thereof for use in a method of treating an HIV infection in a human having or at risk of having the infection, is provided wherein the method comprises administering to the human a fixed dose combination of a compound of Formula (Ia), (II) or (III) or a pharmaceutically acceptable salt thereof, with a first additional therapeutic agent selected from the group consisting of: abacavir sulfate, tenofovir, tenofovir disoproxil, tenofovir disoproxil fumarate, tenofovir alafenamide, and tenofovir alafenamide hemifumarate and a second additional therapeutic agent selected from the group consisting of emtricitabine and lamivudine.

In another embodiment, a compound of Formula (Ia), (II) or (III) or a pharmaceutically acceptable salt thereof, or a pharmaceutical composition of a compound of Formula (Ia), (II) or (III) or a pharmaceutically acceptable salt thereof for use in a method of treating an HIV infection in a human having or at risk of having the infection, is provided wherein the method comprises administering to the human a unitary dosage form for simultaneous administration to a patient, for example as a solid dosage form for oral administration, of a compound of Formula (Ia), (II) or (III) or a pharmaceutically acceptable salt thereof, with a first additional therapeutic agent selected from the group consisting of: abacavir sulfate, tenofovir, tenofovir disoproxil, tenofovir disoproxil fumarate, tenofovir alafenamide, and tenofovir alafenamide hemifumarate and a second additional therapeutic agent selected from the group consisting of emtricitabine and lamivudine.

In another embodiment, a compound of Formula (Ia), (II) or (III) or a pharmaceutically acceptable salt thereof, or a pharmaceutical composition of a compound of Formula (Ia), (II) or (III) or a pharmaceutically acceptable salt thereof for use in a method of treating an HIV infection in a human having or at risk of having the infection, is provided wherein said method further comprises administering to the human a therapeutically effective amount of tenofovir disoproxil and emtricitabine.

In another embodiment, a compound of Formula (Ia), (II) or (III) or a pharmaceutically acceptable salt thereof, or a pharmaceutical composition of a compound of Formula (Ia), (II) or (III) or a pharmaceutically acceptable salt thereof for use in a method of treating an HIV infection in a human having or at risk of having the infection, is provided wherein said method further comprises administering to the human a therapeutically effective amount of tenofovir alafenamide and emtricitabine.

In another embodiment, a method of using a compound having the Formula (Ia), (II) or (III) in therapy is provided. In particular, a method of treating the proliferation of the HIV virus, treating AIDS, or delaying the onset of AIDS or ARC symptoms in a mammal (e.g., a human) is provided, comprising administering to the mammal a compound having the Formula (Ia), (II) or (III), or a stereoisomer or pharmaceutically acceptable salt thereof, and a pharmaceutically acceptable excipient.

In another embodiment, a composition comprising a compound having the Formula (Ia), (II) or (III), or a stereoisomer or pharmaceutically acceptable salt thereof, and a pharmaceutically acceptable excipient, for use in a method of treating the proliferation of the HIV virus, treating AIDS, or delaying the onset of AIDS or ARC symptoms in a mammal (e.g., a human) is provided.

In another embodiment, a compound of Formula (Ia), (II) or (III), or a pharmaceutically acceptable salt thereof, or a pharmaceutical composition of a compound of Formula (Ia), (II) or (III) or a pharmaceutically acceptable salt thereof, is provided for use in pre-exposure prophylaxis (PrEP) before the exposure of the individual to the HIV virus to prevent HIV infection from taking hold if the individual is exposed to the virus and/or to keep the virus from establishing a permanent infection and/or to prevent the appearance of symptoms of the disease and/or to prevent the virus from reaching detectable levels in the blood.

In another embodiment, the use of a compound of Formula (Ia), (II) or (III) as described herein, or a pharmaceutically acceptable salt thereof, for the manufacture of a medicament for the treatment of an HIV infection in a human being having or at risk of having the infection is disclosed.

In another embodiment, the use of a compound of Formula (Ia), (II) or (III), or a pharmaceutically acceptable salt thereof, as a research tool is disclosed.

In another embodiment, an article of manufacture comprising a composition effective to treat an HIV infection; and packaging material comprising a label which indicates that the composition can be used to treat infection by HIV is disclosed. Exemplary compositions comprise a compound of Formula (Ia), (II) or (III) according to this embodiments disclosed herein or a pharmaceutically acceptable salt thereof.

In still another embodiment, a method of inhibiting the replication of HIV is disclosed. The method comprises exposing the virus to an effective amount of the compound of Formula (Ia), (II) or (III), or a salt thereof, under conditions where replication of HIV is inhibited.

In another embodiment, the use of a compound of Formula (Ia), (II) or (III) to inhibit the activity of the HIV integrase enzyme is disclosed.

In another embodiment, the use of a compound of Formula (Ia), (II) or (III), or a salt thereof, to inhibit the replication of HIV is disclosed.

The present disclosure also provides compounds of each of the Formulae herein, as well as each subgroup and embodiment thereof, including a compound selected from the group of Formula (Ia), (II), and (III), or a pharmaceutically acceptable salt thereof, or a pharmaceutical composition comprising a compound of Formula (Ia), (II), or (III), or a pharmaceutically acceptable salt thereof, or one of the specific compounds of the examples herein, or a salt thereof for use in any of the methods of the invention as defined herein.

It is understood that any embodiment of the compounds of any one of Formulas (Ia), (II) or (III), as set forth above, and any specific substituent set forth herein A, A', $R^1$, $R^2$, $R^3$, $R^4$ or $R^5$ group in the compounds of Formulas (Ia) as set forth above, may be independently combined with other embodiments and/or substituents of compounds of any one of Formulas (Ia) to form embodiments not specifically set forth above. In addition, in the event that a list of substituents is listed for any particular A, A', $R^1$, $R^2$, $R^3$, $R^4$, and $R^5$ in a particular embodiment and/or claim, it is understood that each individual substituent may be deleted from the particular embodiment and/or claim and that the remaining list of substituents will be considered to be within the scope of the embodiments disclosed herein.

Pharmaceutical Compositions

For the purposes of administration, in certain embodiments, the compounds described herein are administered as a raw chemical or are formulated as pharmaceutical compositions. Pharmaceutical compositions within the scope of the embodiments disclosed herein comprise a compound of Formula (Ia), (II) or (III), and a pharmaceutically acceptable excipient. The compound of Formula (Ia), (II) or (III) is present in the composition in an amount which is effective to treat a particular disease or condition of interest. The activity of compounds of Formulas (Ia), (II) or (III) can be determined by one skilled in the art, for example, as described in the Examples below. Appropriate concentrations and dosages can be readily determined by one skilled in the art.

Administration of the compounds of the embodiments disclosed herein, or their pharmaceutically acceptable salts, in pure form or in an appropriate pharmaceutical composition, can be carried out via any of the accepted modes of administration of agents for serving similar utilities. The pharmaceutical compositions of the embodiments disclosed herein can be prepared by combining a compound of the embodiments disclosed herein with an appropriate pharmaceutically acceptable excipient, and may be formulated into preparations in solid, semi-solid, liquid or gaseous forms, such as tablets, capsules, powders, granules, ointments, solutions, suppositories, injections, inhalants, gels, microspheres, and aerosols. Typical routes of administering such pharmaceutical compositions include, without limitation, oral, topical, transdermal, inhalation, parenteral, sublingual, buccal, rectal, vaginal, and intranasal. Pharmaceutical compositions of the embodiments disclosed herein are formulated so as to allow the active ingredients contained therein to be bioavailable upon administration of the composition to a patient. Compositions that will be administered to a subject or patient take the form of one or more dosage units, where for example, a tablet may be a single dosage unit, and a container of a compound of the embodiments disclosed herein in aerosol form may hold a plurality of dosage units. Actual methods of preparing such dosage forms are known, or will be apparent, to those skilled in this art; for example, see Remington: The Science and Practice of Pharmacy, 20th Edition (Philadelphia College of Pharmacy and Science, 2000). The composition to be administered will, in any event, contain a therapeutically effective amount of a compound of the embodiments disclosed herein, or a pharmaceutically acceptable salt thereof, for treatment of a disease or condition of interest in accordance with the teachings of this disclosure.

In one embodiment, the pharmaceutical composition is a oral dosage unit. In one embodiment, the pharmaceutical composition is a solid oral dosage unit. In one embodiment, the pharmaceutical composition is a tablet.

The pharmaceutical compositions disclosed herein may be prepared by methodology well known in the pharmaceutical art. For example, a pharmaceutical composition intended to be administered by injection can be prepared by combining a compound of the embodiments disclosed herein with sterile, distilled water so as to form a solution. A surfactant may be added to facilitate the formation of a homogeneous solution or suspension. Surfactants are compounds that non-covalently interact with the compound of the embodiments disclosed herein so as to facilitate dissolution or homogeneous suspension of the compound in the aqueous delivery system.

The compounds of the embodiments disclosed herein, or their pharmaceutically acceptable salts, are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy.

Combination Therapy

In certain embodiments, a method for treating or preventing an HIV infection in a human having or at risk of having the infection is provided, comprising administering to the human a therapeutically effective amount of a compound disclosed herein, or a pharmaceutically acceptable salt thereof, in combination with a therapeutically effective amount of one or more (e.g., one, two, three, one or two, or one to three) additional therapeutic agents. In one embodiment, a method for treating an HIV infection in a human having or at risk of having the infection is provided, comprising administering to the human a therapeutically effective amount of a compound disclosed herein, or a pharmaceutically acceptable salt thereof, in combination with a therapeutically effective amount of one or more (e.g., one, two, three, one or two, or one to three) additional therapeutic agents.

In certain embodiments, the present disclosure provides a method for treating an HIV infection, comprising administering to a patient in need thereof a therapeutically effective amount of a compound disclosed herein, or a pharmaceutically acceptable salt, thereof, in combination with a therapeutically effective amount of one or more additional therapeutic agents which are suitable for treating an HIV infection.

A compound as disclosed herein (e.g., any compound of Formula (Ia), (II) or (III)) may be combined with one or more additional therapeutic agents in any dosage amount of the compound of Formula (Ia), (II) or (III) (e.g., from 50 mg to 1000 mg of compound).

In one embodiment, pharmaceutical compositions comprising a compound disclosed herein, or a pharmaceutically acceptable salt thereof, in combination with one or more (e.g., one, two, three, one or two, or one to three) additional therapeutic agents, and a pharmaceutically acceptable excipient are provided.

In one embodiment, kits comprising a compound disclosed herein, or a pharmaceutically acceptable salt thereof, in combination with one or more (e.g., one, two, three, one or two, or one to three) additional therapeutic agents are provided.

In the above embodiments, the additional therapeutic agent may be an anti-HIV agent. For example, in some embodiments, the additional therapeutic agent is selected from the group consisting of HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors (e.g., CCR5 inhibitors, gp41 inhibitors (i.e., fusion inhibitors) and CD4 attachment inhibitors), CXCR4 inhibitors, gp120 inhibitors, G6PD and NADH-oxidase inhibitors, HIV vaccines, HIV maturation inhibitors, latency reversing agents (e.g., histone deacetylase inhibitors, proteasome inhibitors, protein kinase C (PKC) activators, and BRD4 inhibitors), compounds that target the HIV capsid ("capsid inhibitors"; e.g., capsid polymerization inhibitors or capsid disrupting compounds, HIV nucleocapsid p7 (NCp7) inhibitors, HIV p24 capsid protein inhibitors), pharmacokinetic enhancers, immune-based therapies (e.g., Pd-1 modulators, Pd-L1 modulators, toll like receptors modulators, IL-15 agonists,), HIV antibodies, bispecific antibodies and "antibody-like" therapeutic proteins (e.g., DARTs®, Duobodies®, Bites®, XmAbs®, TandAbs®, Fab derivatives) including those targeting HIV gp120 or gp41, combination drugs for HIV, HIV p17 matrix protein inhibitors, IL-13 antagonists, Peptidyl-prolyl cis-trans isomerase A modulators, Protein disulfide isomerase inhibitors, Complement C5a receptor antagonists, DNA methyltransferase inhibitor, HIV vif gene modulators, HIV-1 viral infectivity factor inhibitors, TAT protein inhibitors, HIV-1 Nef modulators, Hck tyrosine kinase modulators, mixed lineage kinase-3 (MLK-3) inhibitors, HIV-1 splicing inhibitors, Rev protein inhibitors, Integrin antagonists, Nucleoprotein inhibitors, Splicing factor modulators, COMM domain containing protein 1 modulators, HIV Ribonuclease H inhibitors, Retrocyclin modulators, CDK-9 inhibitors, Dendritic ICAM-3 grabbing nonintegrin 1 inhibitors, HIV GAG protein inhibitors, HIV POL protein inhibitors, Complement Factor H modulators, Ubiquitin ligase inhibitors, Deoxycytidine kinase inhibitors, Cyclin dependent kinase inhibitors Proprotein convertase PC9 stimulators, ATP dependent RNA helicase DDX3X inhibitors, reverse transcriptase priming complex inhibitors, HIV gene therapy, PI3K inhibitors, compounds such as those disclosed in WO 2013/006738 (Gilead Sciences), US 2013/0165489 (University of Pennsylvania), WO 2013/091096A1 (Boehringer Ingelheim), WO 2009/062285 (Boehringer Ingelheim), US20140221380

(Japan Tobacco), US20140221378 (Japan Tobacco), WO 2010/130034 (Boehringer Ingelheim), WO 2013/159064 (Gilead Sciences), WO 2012/145728 (Gilead Sciences), WO2012/003497 (Gilead Sciences), WO2014/100323 (Gilead Sciences), WO2012/145728 (Gilead Sciences), WO2013/159064 (Gilead Sciences) and WO 2012/003498 (Gilead Sciences) and WO 2013/006792 (Pharma Resources), and other drugs for treating HIV, and combinations thereof.

In certain embodiments, the additional therapeutic is selected from the group consisting of HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, pharmacokinetic enhancers, and combinations thereof.

In certain embodiments a compound of Formula (Ia), (II) or (III) is formulated as a tablet, which may optionally contain one or more other compounds useful for treating HIV. In certain embodiments, the tablet can contain another active ingredient for treating HIV, such as HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, pharmacokinetic enhancers, and combinations thereof.

In certain embodiments, such tablets are suitable for once daily dosing. In certain embodiments, the additional therapeutic agent is selected from one or more of:

(1) Combination drugs selected from the group consisting of ATRIPLA® (efavirenz+tenofovir disoproxil fumarate+emtricitabine), COMPLERA® (EVIPLERA®, rilpivirine+tenofovir disoproxil fumarate+emtricitabine), STRIBILD® (elvitegravir+cobicistat+tenofovir disoproxil fumarate+emtricitabine), dolutegravir+abacavir sulfate+lamivudine, TRIUMEQ® (dolutegravir+abacavir+lamivudine), lamivudine+nevirapine+zidovudine, dolutegravir+rilpivirine, atazanavir sulfate+cobicistat, atazanavir+cobicistat, darunavir+cobicistat, efavirenz+lamivudine+tenofovir disoproxil fumarate, tenofovir alafenamide hemifumarate+emtricitabine+cobicistat+elvitegravir, tenofovir alafenamide hemifumarate+emtricitabine, tenofovir alafenamide+emtricitabine, tenofovir alafenamide hemifumarate+emtricitabine+rilpivirine, tenofovir alafenamide+emtricitabine+rilpivirine, Vacc-4x+romidepsin, darunavir+tenofovir alafenamide hemifumarate+emtricitabine+cobicistat, APH-0812, raltegravir+lamivudine, KALETRA® (ALUVIA®, lopinavir+ritonavir), atazanavir sulfate+ritonavir, COMBIVIR® (zidovudine+lamivudine, AZT+3TC), EPZICOM® (Livexa®, abacavir sulfate+lamivudine, ABC+3TC), TRIZIVIR® (abacavir sulfate+zidovudine+lamivudine, ABC+AZT+3TC), TRUVADA® (tenofovir disoproxil fumarate+emtricitabine, TDF+FTC), tenofovir+lamivudine and lamivudine+tenofovir disoproxil fumarate;

(2) HIV protease inhibitors selected from the group consisting of amprenavir, atazanavir, fosamprenavir, fosamprenavir calcium, indinavir, indinavir sulfate, lopinavir, ritonavir, nelfinavir, nelfinavir mesylate, saquinavir, saquinavir mesylate, tipranavir, brecanavir, darunavir, DG-17, TMB-657 (PPL-100) and TMC-310911;

(3) HIV non-nucleoside or non-nucleotide inhibitors of reverse transcriptase selected from the group consisting of delavirdine, delavirdine mesylate, nevirapine, etravirine, dapivirine, doravirine, rilpivirine, efavirenz, KM-023, VM-1500, lentinan and AIC-292;

(4) HIV nucleoside or nucleotide inhibitors of reverse transcriptase selected from the group consisting of VIDEX® and VIDEX® EC (didanosine, ddl), zidovudine, emtricitabine, didanosine, stavudine, zalcitabine, lamivudine, censavudine, abacavir, abacavir sulfate, amdoxovir, elvucitabine, alovudine, phosphazid, fozivudine tidoxil, apricitabine, amdoxovir, KP-1461, fosalvudine tidoxil, tenofovir, tenofovir disoproxil, tenofovir disoproxil fumarate, tenofovir disoproxil hemifumarate, tenofovir alafenamide, tenofovir alafenamide hemifumarate, tenofovir alafenamide fumarate, adefovir, adefovir dipivoxil, and festinavir;

(5) HIV integrase inhibitors selected from the group consisting of curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, raltegravir, elvitegravir, dolutegravir and cabotegravir;

(6) HIV non-catalytic site, or allosteric, integrase inhibitors (NCINI) selected from the group consisting of CX-05168, CX-05045 and CX-14442;

(7) HIV gp41 inhibitors selected from the group consisting of enfuvirtide, sifuvirtide and albuvirtide;

(8) HIV entry inhibitors selected from the group consisting of cenicriviroc;

(9) HIV gp120 inhibitors selected from the group consisting of Radha-108 (Receptol) and BMS-663068;

(10) CCR5 inhibitors selected from the group consisting of aplaviroc, vicriviroc, maraviroc, cenicriviroc, PRO-140, Adaptavir (RAP-101), TBR-220 (TAK-220), nifeviroc (TD-0232), TD-0680, and vMIP (Haimipu);

(11) CD4 attachment inhibitors selected from the group consisting of ibalizumab;

(12) CXCR4 inhibitors selected from the group consisting of plerixafor, ALT-1188, vMIP and Haimipu;

(13) Pharmacokinetic enhancers selected from the group consisting of cobicistat and ritonavir;

(14) Immune-based therapies selected from the group consisting of dermaVir, interleukin-7, plaquenil (hydroxychloroquine), proleukin (aldesleukin, IL-2), interferon alfa, interferon alfa-2b, interferon alfa-n3, pegylated interferon alfa, interferon gamma, hydroxyurea, mycophenolate mofetil (MPA) and its ester derivative mycophenolate mofetil (MMF), WF-10, ribavirin, IL-2, IL-12, polymer polyethyleneimine (PEI), Gepon, VGV-1, MOR-22, BMS-936559, toll-like receptors modulators (tlr1, tlr2, tlr3, tlr4, tlr5, tlr6, tlr7, tlr8, tlr9, tlr10, tlr11, tlr12 and tlr13), rintatolimod and IR-103;

(15) HIV vaccines selected from the group consisting of peptide vaccines, recombinant subunit protein vaccines, live vector vaccines, DNA vaccines, virus-like particle vaccines (pseudovirion vaccine), CD4-derived peptide vaccines, vaccine combinations, rgp120 (AIDSVAX), ALVAC HIV (vCP1521)/AIDSVAX B/E (gp120) (RV144), Remune, ITV-1, Contre Vir, Ad5-ENVA-48, DCVax-001 (CDX-2401), PEP-6409, Vacc-4x, Vacc-C5, VAC-3S, multiclade DNA recombinant adenovirus-5 (rAd5), Pennvax-G, VRC-HIV MAB060-00-AB, AVX-101, Tat Oyi vaccine, AVX-201, HIV-LAMP-vax, Ad35, Ad35-GRIN, NAcGM3/VSSP ISA-51, poly-ICLC adjuvanted vaccines, TatImmune, GTU-multiHIV (FIT-06), AGS-004, gp140[delta]V2.TV1+MF-59, rVSVIN HIV-1 gag vaccine, SeV-Gag vaccine, AT-20, DNK-4, Ad35-GRIN/ENV, TBC-M4, HIVAX, HIVAX-2, NYVAC-HIV-PT1, NYVAC-HIV-PT4, DNA-HIV-PT123, rAAV1-PG9DP, GOVX-B11, GOVX-B21, ThV-01, TUTI-16, VGX-3300, TVI-HIV-1, Ad-4 (Ad4-env Clade C+Ad4-mGag), EN41-UGR7C, EN41-FPA2, PreVaxTat, TL-01, SAV-001, AE-H, MYM-V101, CombiHIVvac, ADVAX, MYM-V201, MVA-CMDR, ETV-01 and DNA-Ad5 gag/pol/nef/nev (HVTN505);

(16) HIV antibodies, bispecific antibodies and "antibody-like" therapeutic proteins (such as DARTs®, Duobodies®, Bites®, XmAbs®, TandAbs®, Fab derivatives) including BMS-936559, TMB-360 and those targeting HIV gp120 or gp41 selected from the group consisting of bavituximab, UB-421, C2F5, C2G12, C4E10, C2F5+C2G12+C4E10, 3-BNC-117, PGT145, PGT121, MDX010 (ipilimumab), VRC01, A32, 7B2, 10E8 and VRC07;

(17) latency reversing agents selected from the group consisting of Histone deacetylase inhibitors such as Romidepsin, vorinostat, panobinostat; Proteasome inhibitors such as Velcade; protein kinase C (PKC) activators such as Indolactam, Prostratin, Ingenol B and DAG-lactones, Ionomycin, GSK-343, PMA, SAHA, BRD4 inhibitors, IL-15, JQ1, disulfram, and amphotericin B;

(18) HIV nucleocapsid p7 (NCp7) inhibitors selected from the group consisting of azodicarbonamide;

(19) HIV maturation inhibitors selected from the group consisting of BMS-955176 and GSK-2838232;

(20) PI3K inhibitors selected from the group consisting of idelalisib, AZD-8186, buparlisib, CLR-457, pictilisib, neratinib, rigosertib, rigosertib sodium, EN-3342, TGR-1202, alpelisib, duvelisib, UCB-5857, taselisib, XL-765, gedatolisib, VS-5584, copanlisib, CAI orotate, perifosine, RG-7666, GSK-2636771, DS-7423, panulisib, GSK-2269557, GSK-2126458, CUDC-907, PQR-309, INCB-040093, pilaralisib, BAY-1082439, puquitinib mesylate, SAR-245409, AMG-319, RP-6530, ZSTK-474, MLN-1117, SF-1126, RV-1729, sonolisib, LY-3023414, SAR-260301 and CLR-1401;

(21) the compounds disclosed in WO 2004/096286 (Gilead Sciences), WO 2006/110157 (Gilead Sciences), WO 2006/015261 (Gilead Sciences), WO 2013/006738 (Gilead Sciences), US 2013/0165489 (University of Pennsylvania), US20140221380 (Japan Tobacco), US20140221378 (Japan Tobacco), WO 2013/006792 (Pharma Resources), WO 2009/062285 (Boehringer Ingelheim), WO 2010/130034 (Boehringer Ingelheim), WO 2013/091096A1 (Boehringer Ingelheim), WO 2013/159064 (Gilead Sciences), WO 2012/145728 (Gilead Sciences), WO2012/003497 (Gilead Sciences), WO2014/100323 (Gilead Sciences), WO2012/145728 (Gilead Sciences), WO2013/159064 (Gilead Sciences) and WO 2012/003498 (Gilead Sciences); and

(22) other drugs for treating HIV selected from the group consisting of BanLec, MK-8507, AG-1105, TR-452, MK-8591, REP 9, CYT-107, alisporivir, NOV-205, IND-02, metenkefalin, PGN-007, Acemannan, Gamimune, Prolastin, 1,5-dicaffeoylquinic acid, BIT-225, RPI-MN, VSSP, Hlviral, IMO-3100, SB-728-T, RPI-MN, VIR-576, HGTV-43, MK-1376, rHIV7-shl-TAR-CCR5RZ, MazF gene therapy, BlockAide, ABX-464, SCY-635, naltrexone, AAV-eCD4-Ig gene therapy and PA-1050040 (PA-040).

In certain embodiments, a compound disclosed herein, or a pharmaceutically acceptable salt thereof, is combined with one, two, three, four or more additional therapeutic agents. In certain embodiments, a compound disclosed herein, or a pharmaceutically acceptable salt thereof, is combined with two additional therapeutic agents. In other embodiments, a compound disclosed herein, or a pharmaceutically acceptable salt thereof, is combined with three additional therapeutic agents. In further embodiments, a compound disclosed herein, or a pharmaceutically acceptable salt thereof, is combined with four additional therapeutic agents. The one, two, three, four or more additional therapeutic agents can be different therapeutic agents selected from the same class of therapeutic agents, and/or they can be selected from different classes of therapeutic agents. In a specific embodiment, a compound disclosed herein, or a pharmaceutically acceptable salt thereof, is combined with an HIV non-nucleoside inhibitor of reverse transcriptase. In a specific embodiment, a compound disclosed herein, or a pharmaceutically acceptable salt thereof, is combined with an HIV nucleoside or nucleotide inhibitor of reverse transcriptase and an HIV non-nucleoside inhibitor of reverse transcriptase. In another specific embodiment, a compound disclosed herein, or a pharmaceutically acceptable salt thereof, is combined with an HIV nucleoside or nucleotide inhibitor of reverse transcriptase, and an HIV protease inhibiting compound. In a further embodiment, a compound disclosed herein, or a pharmaceutically acceptable salt thereof, is combined with an HIV nucleoside or nucleotide inhibitor of reverse transcriptase, an HIV non-nucleoside inhibitor of reverse transcriptase, and an HIV protease inhibiting compound. In an additional embodiment, a compound disclosed herein, or a pharmaceutically acceptable salt thereof, is combined with an HIV nucleoside or nucleotide inhibitor of reverse transcriptase, an HIV non-nucleoside inhibitor of reverse transcriptase, and a pharmacokinetic enhancer. In certain embodiments, a compound disclosed herein, or a pharmaceutically acceptable salt thereof, is combined with at least one HIV nucleoside inhibitor of reverse transcriptase, an integrase inhibitor, and a pharmacokinetic enhancer. In another embodiment, a compound disclosed herein, or a pharmaceutically acceptable salt thereof, is combined with two HIV nucleoside or nucleotide inhibitors of reverse transcriptase.

In a particular embodiment, a compound disclosed herein, or a pharmaceutically acceptable salt thereof, is combined with one, two, three, four or more additional therapeutic agents selected from Triumeq® (dolutegravir+abacavir+lamivudine), dolutegravir+abacavir sulfate+lamivudine, raltegravir, raltegravir+lamivudine, Truvada® (tenofovir disoproxil fumarate+emtricitabine, TDF+FTC), maraviroc, enfuvirtide, Epzicom® (Livexa®, abacavir sulfate+lamivudine, ABC+3TC), Trizivir® (abacavir sulfate+zidovudine+lamivudine, ABC+AZT+3TC), adefovir, adefovir dipivoxil, Stribild® (elvitegravir+cobicistat+tenofovir disoproxil fumarate+emtricitabine), rilpivirine, rilpivirine hydrochloride, Complera® (Eviplera®, rilpivirine+tenofovir disoproxil fumarate+emtricitabine), Cobicistat, atazanavir sulfate+cobicistat, atazanavir+cobicistat, darunavir+cobicistat, Atripla® (efavirenz+tenofovir disoproxil fumarate+emtricitabine), atazanavir, atazanavir sulfate, dolutegravir, elvitegravir, Aluvia® (Kaletra®, lopinavir+ritonavir), ritonavir, emtricitabine, atazanavir sulfate+ritonavir, darunavir, lamivudine, Prolastin, fosamprenavir, fosamprenavir calcium, efavirenz, Combivir® (zidovudine+lamivudine, AZT+3TC), etravirine, nelfinavir, nelfinavir mesylate, interferon, didanosine, stavudine, indinavir, indinavir sulfate, tenofovir+lamivudine, zidovudine, nevirapine, saquinavir, saquinavir mesylate, aldesleukin, zalcitabine, tipranavir, amprenavir, delavirdine, delavirdine mesylate, Radha-108 (Receptol), Hlviral, lamivudine+tenofovir disoproxil fumarate, efavirenz+lamivudine+tenofovir disoproxil fumarate, phosphazid, lamivudine+nevirapine+zidovudine, abacavir, abacavir sulfate, tenofovir, tenofovir disoproxil, tenofovir disoproxil fumarate, darunavir+cobicistat, atazanavir sulfate+cobicistat, atazanavir+cobicistat, tenofovir alafenamide and tenofovir alafenamide hemifumarate.

In a particular embodiment, a compound disclosed herein, or a pharmaceutically acceptable salt thereof, is combined with abacavir sulfate, tenofovir, tenofovir disoproxil, tenofovir disoproxil fumarate, tenofovir disoproxil hemifumarate, tenofovir alafenamide or tenofovir alafenamide hemifumarate.

In a particular embodiment, a compound disclosed herein, or a pharmaceutically acceptable salt thereof, is combined with tenofovir, tenofovir disoproxil, tenofovir disoproxil fumarate, tenofovir alafenamide, or tenofovir alafenamide hemifumarate.

In a particular embodiment, a compound disclosed herein, or a pharmaceutically acceptable salt thereof, is combined with a first additional therapeutic agent selected from the group consisting of: abacavir sulfate, tenofovir, tenofovir disoproxil, tenofovir disoproxil fumarate, tenofovir alafenamide, and tenofovir alafenamide hemifumarate and a second additional therapeutic agent selected from the group consisting of emtricitabine and lamivudine.

In a particular embodiment, a compound disclosed herein, or a pharmaceutically acceptable salt thereof, is combined with a first additional therapeutic agent selected from the group consisting of: tenofovir, tenofovir disoproxil, tenofovir disoproxil fumarate, tenofovir alafenamide, and tenofovir alafenamide hemifumarate and a second additional therapeutic agent, wherein the second additional therapeutic agent is emtricitabine.

In certain embodiments, a compound disclosed herein, or a pharmaceutically acceptable salt thereof, is combined with 5-30 mg tenofovir alafenamide fumarate, tenofovir alafenamide hemifumarate, or tenofovir alafenamide and 200 mg emtricitabine. In certain embodiments, a compound disclosed herein, or a pharmaceutically acceptable salt thereof, is combined with 5-10; 5-15; 5-20; 5-25; 25-30; 20-30; 15-30; or 10-30 mg tenofovir alafenamide fumarate, tenofovir alafenamide hemifumarate, or tenofovir alafenamide and 200 mg emtricitabine. In certain embodiments, a compound disclosed herein, or a pharmaceutically acceptable salt thereof, is combined with 10 mg tenofovir alafenamide fumarate, tenofovir alafenamide hemifumarate, or tenofovir alafenamide and 200 mg emtricitabine. In certain embodiments, a compound disclosed herein, or a pharmaceutically acceptable salt thereof, is combined with 25 mg tenofovir alafenamide fumarate, tenofovir alafenamide hemifumarate, or tenofovir alafenamide and 200 mg emtricitabine. A compound as disclosed herein (e.g., a compound of formula (Ia)) may be combined with the agents provided herein in any dosage amount of the compound (e.g., from 50 mg to 500 mg of compound) the same as if each combination of dosages were specifically and individually listed.

In certain embodiments, a compound disclosed herein, or a pharmaceutically acceptable salt thereof, is combined with 200-400 mg tenofovir disoproxil fumarate, tenofovir disoproxil hemifumarate, or tenofovir disoproxil and 200 mg emtricitabine. In certain embodiments, a compound disclosed herein, or a pharmaceutically acceptable salt thereof, is combined with 200-250; 200-300; 200-350; 250-350; 250-400; 350-400; 300-400; or 250-400 mg tenofovir disoproxil fumarate, tenofovir disoproxil hemifumarate, or tenofovir disoproxil and 200 mg emtricitabine. In certain embodiments, a compound disclosed herein, or a pharmaceutically acceptable salt thereof, is combined with 300 mg tenofovir disoproxil fumarate, tenofovir disoproxil hemifumarate, or tenofovir disoproxil and 200 mg emtricitabine. A compound as disclosed herein (e.g., a compound of formula (Ia)) may be combined with the agents provided herein in any dosage amount of the compound (e.g., from 50 mg to 500 mg of compound) the same as if each combination of dosages were specifically and individually listed.

In certain embodiments, when a compound disclosed herein is combined with one or more additional therapeutic agents as described above, the components of the composition are administered as a simultaneous or sequential regimen. When administered sequentially, the combination may be administered in two or more administrations.

In certain embodiments, a compound disclosed herein is combined with one or more additional therapeutic agents in a unitary dosage form for simultaneous administration to a patient, for example as a solid dosage form for oral administration.

In certain embodiments, a compound disclosed herein is administered with one or more additional therapeutic agents. Co-administration of a compound disclosed herein with one or more additional therapeutic agents generally refers to simultaneous or sequential administration of a compound disclosed herein and one or more additional therapeutic agents, such that therapeutically effective amounts of the compound disclosed herein and one or more additional therapeutic agents are both present in the body of the patient.

Co-administration includes administration of unit dosages of the compounds disclosed herein before or after administration of unit dosages of one or more additional therapeutic agents, for example, administration of the compound disclosed herein within seconds, minutes, or hours of the administration of one or more additional therapeutic agents. For example, in some embodiments, a unit dose of a compound disclosed herein is administered first, followed within seconds or minutes by administration of a unit dose of one or more additional therapeutic agents. Alternatively, in other embodiments, a unit dose of one or more additional therapeutic agents is administered first, followed by administration of a unit dose of a compound disclosed herein within seconds or minutes. In some embodiments, a unit dose of a compound disclosed herein is administered first, followed, after a period of hours (e.g., 1-12 hours), by administration of a unit dose of one or more additional therapeutic agents. In other embodiments, a unit dose of one or more additional therapeutic agents is administered first, followed, after a period of hours (e.g., 1-12 hours), by administration of a unit dose of a compound disclosed herein.

General Synthetic Procedures

The embodiments are also directed to processes and intermediates useful for preparing the subject compounds or pharmaceutically acceptable salts thereof.

Exemplary chemical entities useful in methods of the embodiments will now be described by reference to illustrative synthetic schemes for their general preparation herein and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Furthermore, one of skill in the art will recognize that the transformations shown in the schemes below may be performed in any order that is compatible with the functionality of the particular pendant groups.

Representative syntheses of compounds of the present disclosure are described in schemes below, and the particular examples that follow. Schemes 1 and 2 are provided as further embodiments of the invention and illustrate general methods which were used to prepare compounds having the Formula (Ia) and which can be used to prepare additional compounds having the Formula (Ia). The methodology is compatible with a wide variety of functionalities.

Scheme 1

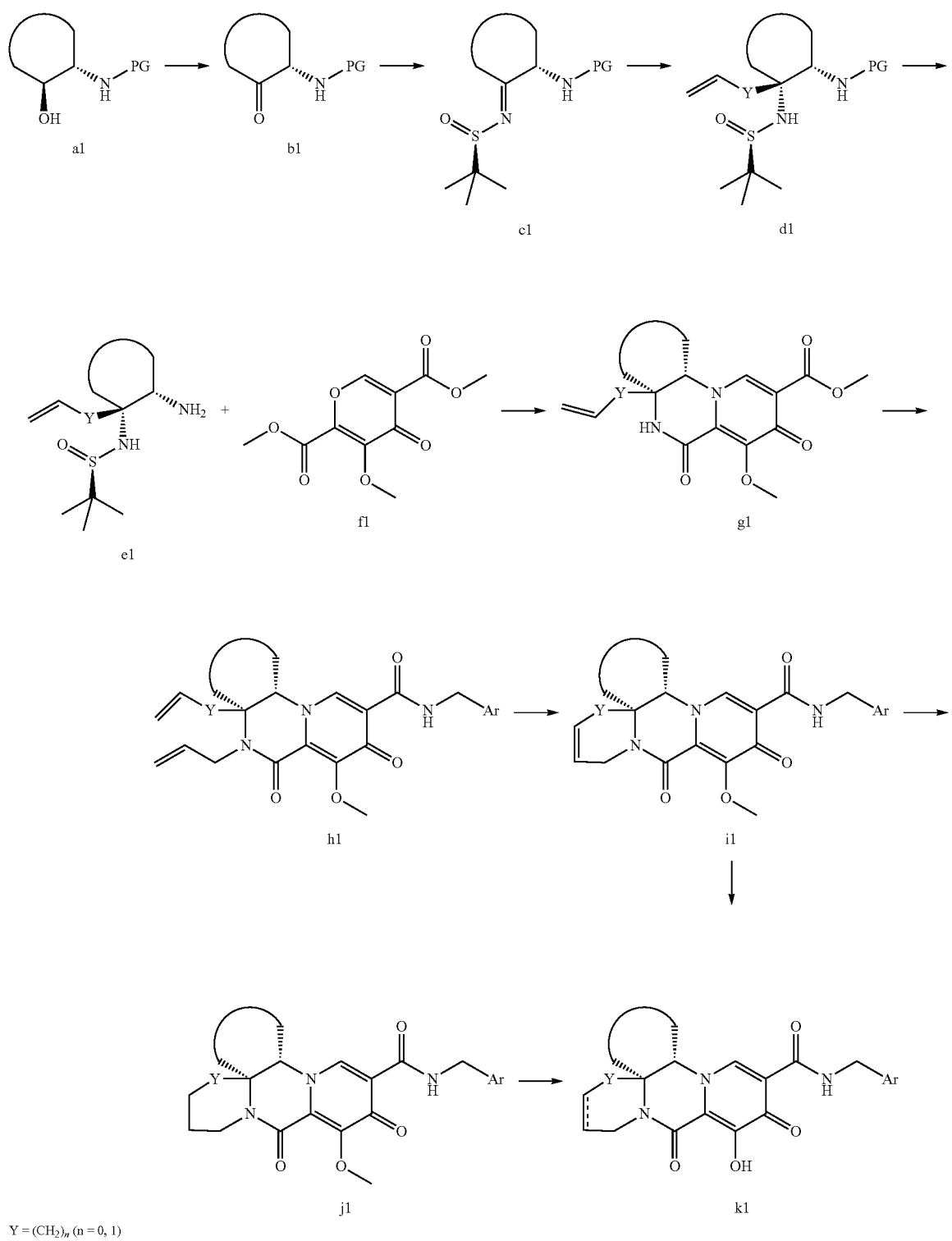

Y = (CH$_2$)$_n$ (n = 0, 1)
PG=Protecting Group

Alcohol a1 is oxidized to form the ketone b1 which is further reacted to form the sulfinylimine c1. Reaction with an activated vinyl containing reagent such as allyl or vinyl magnesium bromide forms the adduct d1. The amine is then deprotected to form e1 which is reacted with f1 to form bicycle g1. Allylation of the amide forms h1 which is further cyclized to form i1. The internal alkene can be kept or reduced to form k1. Finally, the methoxy group is converted to the hydroxyl to form j1.

The following Examples illustrate various methods of making compounds of this disclosure, i.e., compound of Formula (Ia):

Scheme 2

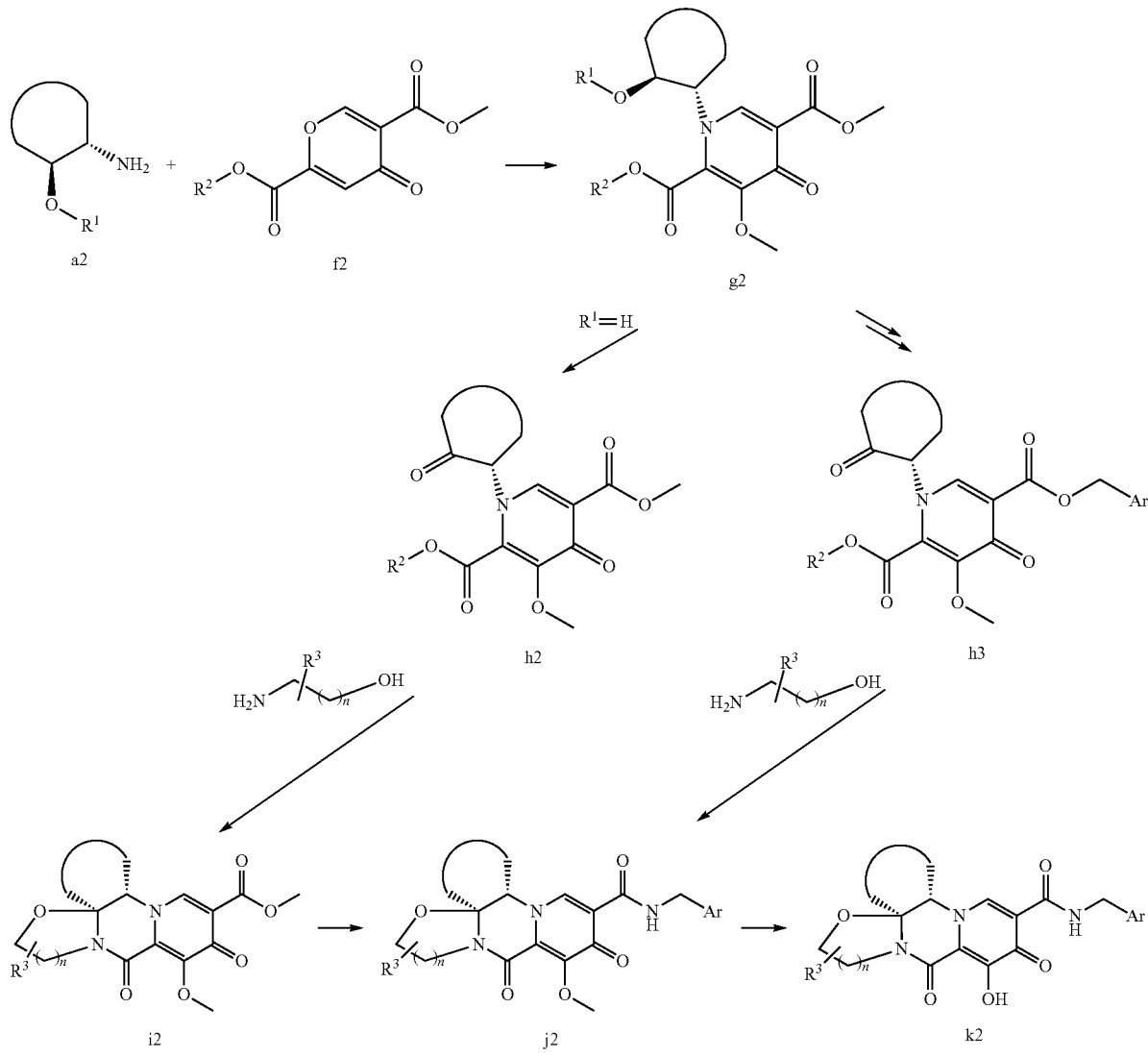

$R^1$ = H or protecting group
$R^2$ = alkyl
$R^3$ = substituent (H or alkyl)
n = 1, 2

Reaction between the amine a2 and 12 forms g2. When $R^1$ is H, the hydroxyl is oxidized to form the ketone h2. Cyclization with an hydroxyl alkyl amine gives tetracyclic i2. Hydrolysis of the ester followed by amide coupling provides j2. The methoxy group is then be converted to the hydroxy to give k2.

In certain embodiments, when $R^1$ is a protecting group, the methyl ester of g2 is selectively hydrolyzed and converted to the amide. Deprotection of the alcohol, followed by oxidation provides h3. At this point, coupling with an hydroxyl alkyl amine provides tricycle j2. Finally, the methoxy is converted to hydroxy to give k2.

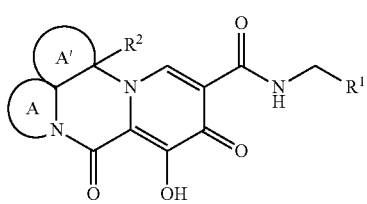

(Ia)

wherein A, A', $R^1$ and $R^2$ are as defined above. It is understood that one skilled in the art may be able to make these compounds by similar methods or by combining other methods known to one skilled in the art. It is also understood that one skilled in the art would be able to make, in a similar manner as described above and below, other compounds of Formula (Ia) not specifically illustrated below by using the appropriate starting components and modifying the parameters of the synthesis as needed. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, for example, Advanced Organic Chemistry: Reactions, Mechanisms, and Structure, 5th edition (Wiley, December 2000)) or prepared as described herein.

The following examples are provided for purposes of illustration, not limitation.

EXAMPLES

Example 1

Preparation of Compound 14

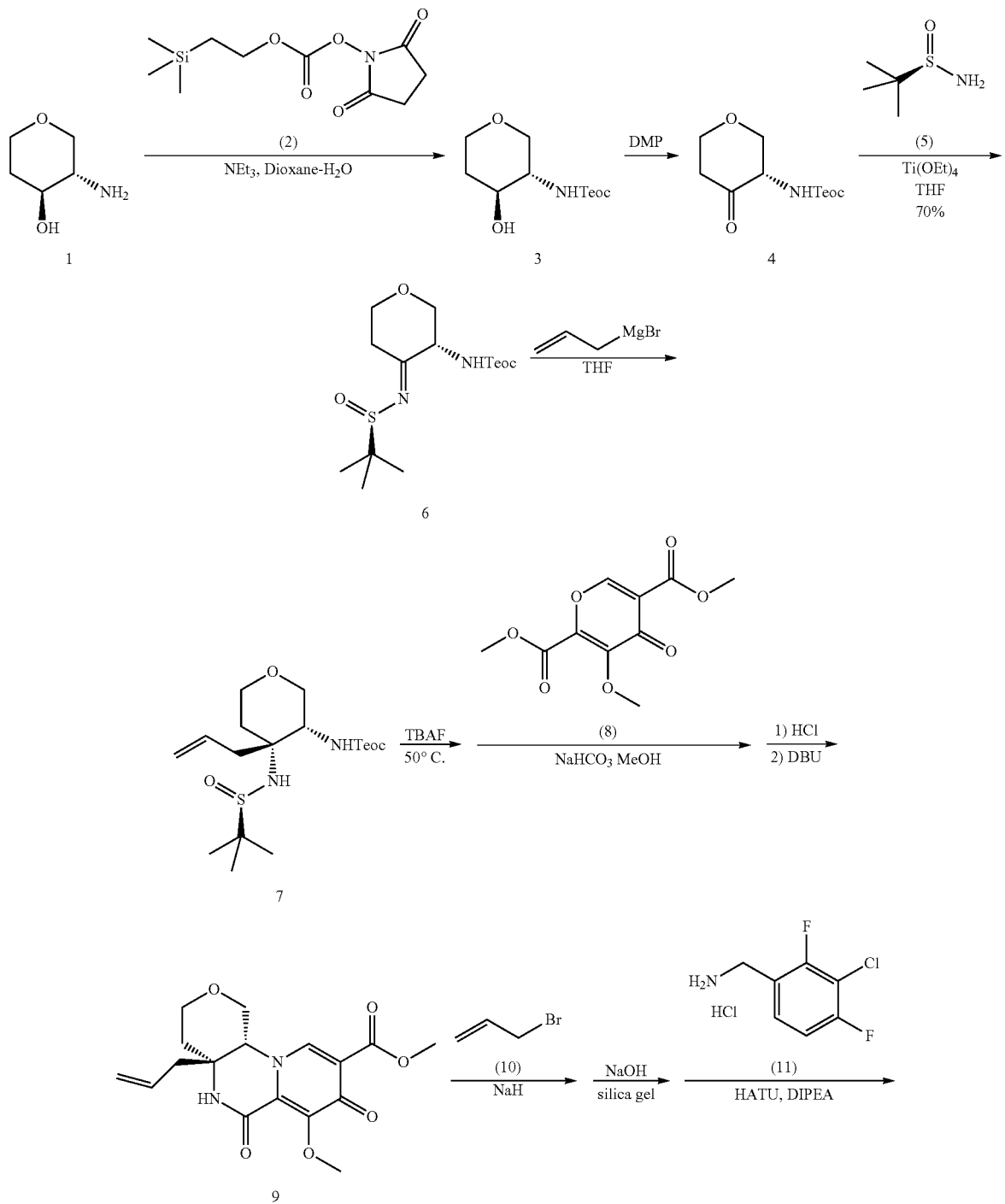

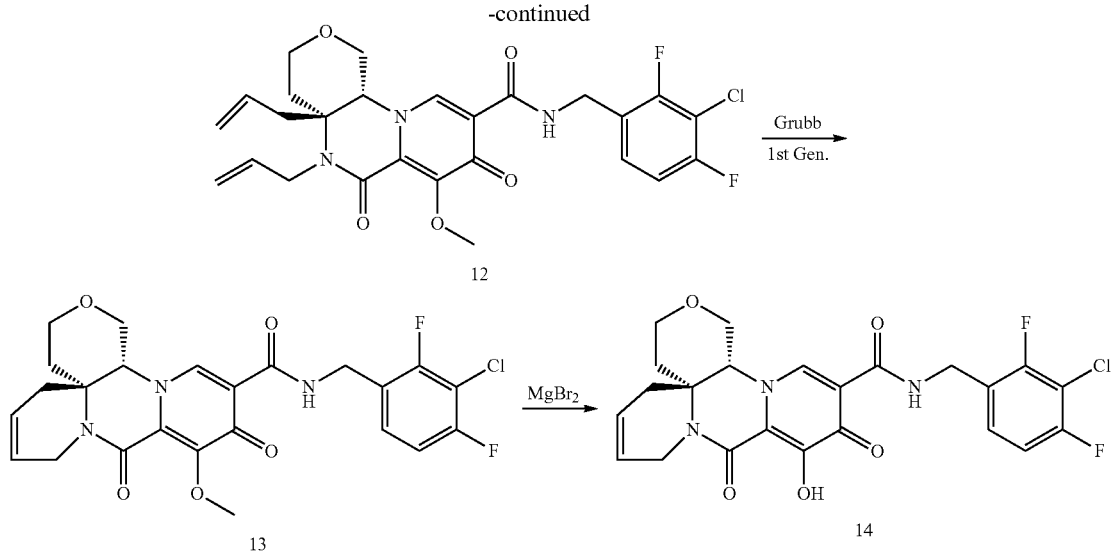

Step 1

A solution of (3S,4S)-3-aminotetrahydro-2H-pyran-4-ol (1, 2667 mg, 22.77 mmol) and triethylamine (4.76 mL, 34.15 mmol) in water (23 mL) and 1,4-dioxane (23 mL) was stirred at room temperature as 1-[(2-trimethylsilyl)ethoxycarbonyloxy]pyrrolidin-2,5-dione (2, 6498 mg, 25.06 mmol) was added. The resulting mixture was stirred at room temperature. After 71 h, the reaction mixture was diluted with water (~125 mL) and extracted with ethyl acetate (~125 mL×2). The extracts were washed with water (125 mL×1), combined, dried ($Na_2SO_4$) and concentrated. The residue was purified by column chromatography on silica gel (120 g column) using hexanes-ethyl acetate as eluents and the product containing fractions were pooled and concentrated to get compound 3: $^1$H NMR (400 MHz, Chloroform-d) δ 4.81 (s, 1H), 4.25-4.09 (m, 2H), 4.09-3.97 (m, 1H), 3.91 (dt, J=11.6, 4.7 Hz, 1H), 3.69 (s, 1H), 3.52 (d, J=9.5 Hz, 1H), 3.46 (ddd, J=11.9, 9.1, 3.1 Hz, 1H), 3.21 (t, J=9.4 Hz, 1H), 2.46 (s, 1H), 2.01 (dddd, J=13.1, 5.4, 4.4, 3.2 Hz, 1H), 1.65 (dtd, J=13.2, 8.8, 4.1 Hz, 1H), 1.07-0.90 (m, 2H), 0.04 (s, 9H). LCMS-ESI$^+$ (m/z): [M+H—$C_2H_4$]$^+$ calculated for $C_9H_{20}NO_4Si$: 234.12. found: 233.94.

Step 2

A mixture of compound 3 (4.994 g, 19.11 mmol) in dichloromethane (98 mL) was stirred at 0° C. as Dess-Martin periodinane (9724 mg, 22.93 mmol) was added in portion. After 15 min, the mixture was stirred at room temperature for 1.5 h. The reaction mixture was filtered to remove the precipitate, and the solids were washed with dichloromethane. After the filtrate and washing solutions were combined and concentrated, the residue was purified by column chromatography on silica gel (120 g column) using hexanes-ethyl acetate as eluents to get compound 4: $^1$H NMR (400 MHz, Chloroform-d) δ 5.54 (s, 1H), 4.62 (dd, J=10.3, 6.9 Hz, 1H), 4.45 (s, 1H), 4.33 (ddt, J=11.0, 7.4, 1.5 Hz, 1H), 4.25-4.05 (m, 2H), 3.62 (ddd, J=12.4, 11.3, 2.6 Hz, 1H), 3.19 (t, J=10.6 Hz, 1H), 2.77 (td, J=13.1, 7.3 Hz, 1H), 2.52 (ddd, J=13.9, 2.5, 1.3 Hz, 1H), 1.09-0.89 (m, 2H), 0.04 (s, 9H). LCMS-ESI$^+$ (m/z): [M+H—$C_2H_4$]$^+$ calculated for $C_9H_{18}NO_4Si$: 232.10. found: 231.83.

Step 3

To a solution of compound 4 (997 mg, 3.844 mmol) and (R)-t-Bu-sulfinimide (5, 562 mg, 4.637 mmol) in THF (16 mL, 0.25 M) was added Ti(OEt)$_4$ (1.63 ml, 7.775 mmol) at room temperature for 16 h. The reaction mixture was poured into a stirred mixture of ethyl acetate (~20 mL) and aq. NaHCO$_3$ (~15 mL). After some celite was added to the mixture, it was filtered through Celite pad. The filter cake was washed with ethyl acetate (×2). The filtrate and washing were combined, dried (MgSO$_4$), and concentrated. The residue was purified by column chromatography on silica gel (40 g column) using dichloromethane-ethyl acetate as eluents to get compound 6: $^1$H NMR (400 MHz, Chloroform-d) δ 5.55 (s, 1H), 4.51 (s, 1H), 4.41 (s, 1H), 4.15 (q, J=7.7 Hz, 3H), 3.77 (d, J=14.6 Hz, 1H), 3.53 (td, J=11.8, 2.4 Hz, 1H), 3.22 (t, J=10.3 Hz, 1H), 2.63 (ddd, J=14.5, 12.1, 6.5 Hz, 1H), 1.26 (s, 9H), 1.06-0.89 (m, 2H), 0.03 (s, 10H). LCMS-ESI$^+$ (m/z): [M+H—$C_2H_4$]$^+$ calculated for $C_{13}H_{27}N_2O_4SSi$: 335.15. found: 334.83.

Step 4

To a solution of compound 6 (725 mg, 2.000 mmol) in THF (7.2 mL) stirred in an acetone-dry ice bath, was added allylmagnesium bromide (1 M in ether, 6 mL) over ~3 min. The bath was warmed to −35° C. over 50 min and then the reaction mixture was quenched with saturated NH$_4$Cl. After some water was added to dissolve the solids formed, the mixture was extracted with ethyl acetate (~25 mL×2) and the extracts were washed with water (×2). The combined extracts were dried (Na$_2$SO$_4$) and concentrated. The residue was purified by column chromatography on silica gel (80 g column) using hexanes-ethyl acetate to obtain compound 7: $^1$H NMR (400 MHz, Chloroform-d) δ 5.92 (dt, J=16.7, 8.6 Hz, 1H), 5.26-5.07 (m, 3H), 4.17 (t, J=8.5 Hz, 2H), 4.05-3.96 (m, 1H), 3.93 (dd, J=11.7, 2.4 Hz, 1H), 3.81-3.64 (m, 2H), 3.59 (dd, J=11.7, 4.2 Hz, 1H), 2.68 (dd, J=14.4, 6.8 Hz, 1H), 2.49-2.38 (m, 1H), 1.81 (ddd, J=14.5, 9.3, 5.2 Hz, 1H), 1.67 (d, J=15.0 Hz, 1H), 1.25 (s, 9H), 0.99 (t, J=8.5 Hz, 2H), 0.04 (d, J=0.8 Hz, 9H). LCMS-ESI$^+$ (m/z): [M+H]$^+$ calculated for $C_{18}H_{37}N_2O_4SSi$: 405.22. found: 404.82.

Step 5

A mixture of compound 7 (463 mg, 1.144 mmol), and tetrabutylammonium fluoride hydrate (640 mg, 2.290 mmol) in acetonitrile (5 mL) was stirred for 8 h at 50° C. After additional tetrabutylammonium fluoride hydrate (640 mg, 2.290 mmol) was added, the mixture was stirred for 8 h at 50° C. The reaction mixture was acidified with 2 N HCl and then ~1 mL saturated NaHCO$_3$ was added to neutralize the solution. The resulting mixture was concentrated to syrup and dried in vacuum. The resulting residue was used for the next reaction: LCMS-ESI$^+$ (m/z): [M+H]$^+$ calculated for C$_{12}$H$_{25}$N$_2$O$_2$S: 261.16. found: 260.91.

To the above crude residue were added the pyrone 8 (278 mg, 1.148 mmol), NaHCO$_3$ (194 mg, 2.309 mmol), water (2 mL), and methanol (2 mL). The resulting mixture was stirred at room temperature for 1 h. After the reaction mixture was concentrated to remove most of solvent and the residue was triturated in dichloromethane (~50 mL), the resulting mixture was dried (MgSO$_4$), filtered, and concentrated.

To the crude concentrated residue in dichloromethane (6 mL) was added 4 N HCl in dioxane (6 mL) and the resulting mixture was stirred at room temperature for 1 h. The mixture was concentrated and dried in vacuum for ~10 min: LCMS-ESI$^+$ (m/z): [M+H]$^+$ calculated for C$_{18}$H$_{25}$N$_2$O$_7$: 381.17. found: 381.06.

A mixture of the above residue and DBU (0.9 mL, 6.018 mmol) in methanol (10 mL) was stirred for 15 min at 50° C. bath. After the solution was concentrated, the residue was purified by column chromatography on silica gel (40 g column) using ethyl acetate-20% methanol in ethyl acetate as eluents to get compound 9: $^1$H NMR (400 MHz, Chloroform-d) δ 8.17 (s, 1H), 8.08 (s, 1H), 5.69 (dddd, J=16.8, 10.1, 8.2, 6.5 Hz, 1H), 5.21-5.12 (m, 1H), 5.05 (dd, J=17.0, 1.7 Hz, 1H), 4.14-4.05 (m, 1H), 3.99 (s, 3H), 3.95 (dd, J=11.5, 5.5 Hz, 1H), 3.87 (s, 3H), 3.83-3.92 (m, 1H), 3.73 (ddt, J=18.3, 6.7, 3.5 Hz, 1H), 3.61 (t, J=11.3 Hz, 1H), 2.43 (dd, J=14.0, 6.5 Hz, 1H), 2.26 (dd, J=14.0, 8.3 Hz, 1H), 1.98-1.85 (m, 2H). LCMS-ESI$^+$ (m/z): [M+H]$^+$ calculated for C$_{17}$H$_{21}$N$_2$O$_6$: 349.14. found: 349.09.

Step 6

A mixture of compound 9 (326 mg, 0.936 mmol) and 60% NaH (149 mg, 3.725 mmol) was placed in an ice bath and DMF (4 mL) was added to the mixture. After stirring for 5 min, allyl bromide (10, 0.2 mL, 2.311 mmol) was added and the resulting mixture was stirred at room temperature for 1.25 h: LCMS-ESI$^+$ (m/z): [M+H]$^+$ calculated for C$_{20}$H$_{25}$N$_2$O$_6$: 389.17. found: 389.13.

To the reaction mixture was added 1 N NaOH (1.9 mL) and the mixture was stirred at 0° C. for 20 min. The reaction mixture was acidified with 4 N HCl in dioxane (~1.5 mL) and the acidified reaction mixture was concentrated to remove all the solvents using rotorvap with vacuum pump and 55° C. bath. The residual mixture was co-evaporated with toluene to get the crude acid: LCMS-ESI$^+$ (m/z): [M+H]$^+$ calculated for C$_{19}$H$_{23}$N$_2$O$_6$: 375.16. found: 375.13.

A mixture of the above crude acid, 3-chloro-2,4-difluorobenzyl amine HCl salt (11, 222 mg, 1.037 mmol), and (dimethylamino)-N,N-dimethyl(3H-[1,2,3]triazolo[4,5-b]pyridin-3-yloxy)methaniminium hexafluorophosphate (HATU, 715 mg, 1.881 mmol) in dichloromethane (10 mL) was stirred at rt as DIPEA (1.75 mL, 10.05 mmol) was added. The mixture was stirred at room temperature for 30 min. The reaction mixture was diluted with ethyl acetate, washed with saturated NH$_4$Cl (×2), saturated NaHCO$_3$ (×2), and brine (×1). After the aqueous fractions were extracted with ethyl acetate (×1), two organic fractions were combined, dried (Na$_2$SO$_4$) and concentrated. The residue was purified by column chromatography on silica gel (40 g column) using ethyl acetate-20% methanol in ethyl acetate as eluent to obtain compound 12: $^1$H NMR (400 MHz, Methanol-d$_4$) δ 8.56 (d, J=2.5 Hz, 1H), 7.37 (td, J=8.4, 6.3 Hz, 1H), 7.08 (td, J=8.7, 1.8 Hz, 1H), 6.10-5.92 (m, 1H), 5.67-5.47 (m, 1H), 5.35 (dd, J=17.3, 1.6 Hz, 1H), 5.24 (dt, J=10.3, 1.3 Hz, 1H), 5.03-4.92 (m, 2H), 4.64 (s, 2H), 4.61 (dd, J=11.0, 5.0 Hz, 1H), 4.44 (dd, J=15.5, 6.5 Hz, 1H), 4.08 (tt, J=11.1, 7.1 Hz, 2H), 3.93 (dd, J=11.4, 5.1 Hz, 1H), 3.90 (s, 3H), 3.86-3.77 (m, 1H), 3.57 (dt, J=14.7, 12.0 Hz, 2H), 2.49 (dd, J=14.3, 7.4 Hz, 1H), 2.44-2.38 (m, 1H), 2.36 (d, J=15.4 Hz, 1H), 2.00 (m, 1H). $^{19}$F NMR (376 MHz, Methanol-d$_4$) δ -117.21 (ddt, J=9.1, 6.0, 2.9 Hz, 1F), -119.79 (d, J=8.8 Hz, 1F). LCMS-ESI$^+$ (m/z): [M+H]$^+$ calculated for C$_{26}$H$_{27}$ClF$_2$N$_3$O$_5$: 534.16. found: 534.17.

Step 7

A solution of compound 12 (63 mg, 0.118 mmol) in dichloromethane (12 mL) was stirred in an ice bath while Ar gas was bubbled. After 30 min, Grubbs Catalyst 1st generation (3.5 mg, 4.654 μmol) was added and the Ar bubbling continued for 15 min. Then, the reaction mixture was refluxed at 47° C. After 2 h, additional Grubbs Catalyst 1st generation (3 mg, 3.99 μmol) was added and the mixture was refluxed. After another 2.75 h, additional Grubbs Catalyst 1st generation (5 mg, 6.649 μmol) was added. After refluxed 45 min, the reaction mixture was concentrated and the residue was purified by column chromatography on silica gel (24 g column) using hexanes-ethyl acetate-20% methanol in ethyl acetate as eluents to get compound 13: $^1$H NMR (400 MHz, Chloroform-d) δ 10.43 (t, J=6.0 Hz, 1H), 8.43 (s, 1H), 7.35-7.21 (m, 1H), 6.92 (td, J=8.5, 1.8 Hz, 1H), 5.72 (d, J=3.2 Hz, 2H), 5.20-5.04 (m, 1H), 4.73-4.56 (m, 2H), 4.18-4.09 (m, 1H), 4.03 (d, J=0.9 Hz, 3H), 3.92 (td, J=14.0, 12.9, 4.7 Hz, 2H), 3.68 (t, J=11.3 Hz, 1H), 3.63-3.53 (m, 1H), 3.47 (dt, J=19.2, 3.7 Hz, 1H), 2.57-2.40 (m, 2H), 1.99-1.86 (m, 1H), 1.68 (ddd, J=16.0, 12.4, 4.4 Hz, 1H). $^{19}$F NMR (376 MHz, Chloroform-d) δ -114.68--115.04 (m, 1F), -117.28 (d, J=7.9 Hz, 1F). LCMS-ESI$^+$ (m/z): [M+H]$^+$ calculated for C$_{24}$H$_{23}$ClF$_2$N$_3$O$_5$: 506.13. found: 506.16.

Step 8

To a solution of compound 13 (11.4 mg, 0.023 mmol) in MeCN (1 mL) was added MgBr$_2$ (10.7 mg, 0.058 mmol) at room temperature and the resulting mixture was stirred for 30 min at 50° C. The reaction mixture was stirred at 0° C. and 1 N HCl (~6 drops) was added to make the mixture a solution. The resulting solution was diluted with water before the product was extracted with dichloromethane (×3). The combined extracts were dried (MgSO$_4$) and concentrated. The residue was purified by column chromatography on silica gel (12 g column) using dichloromethane-20% methanol in dichloromethane as eluents to get compound 14: $^1$H NMR (400 MHz, Chloroform-d) δ 12.60 (s, 1H), 10.45 (s, 1H), 8.37 (s, 1H), 7.26 (m, 1H), 6.92 (td, J=8.5, 1.8 Hz, 1H), 5.85-5.61 (m, 2H), 5.19 (d, J=18.0 Hz, 1H), 4.67 (d, J=5.8 Hz, 2H), 4.13 (s, 1H), 4.00-3.85 (m, 2H), 3.72-3.54 (m, 2H), 3.49 (d, J=18.8 Hz, 1H), 2.57 (dd, J=20.6, 15.2 Hz, 2H), 1.99 (d, J=16.7 Hz, 1H), 1.75 (ddd, J=16.2, 12.4, 4.5 Hz, 1H). $^{19}$F NMR (376 MHz, Chloroform-d) δ -115.09 (s, 1F), -117.30 (s, 1F). LCMS-ESI$^+$ (m/z): [M+H]$^+$ calculated for C$_{23}$H$_{21}$ClF$_2$N$_3$O$_5$: 492.11. found: 492.15.

Example 2

Preparation of Compound 15

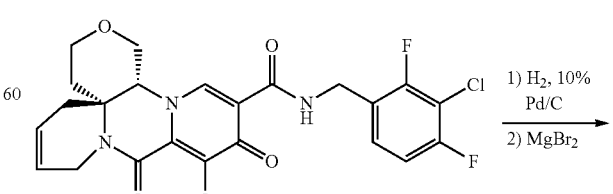

13

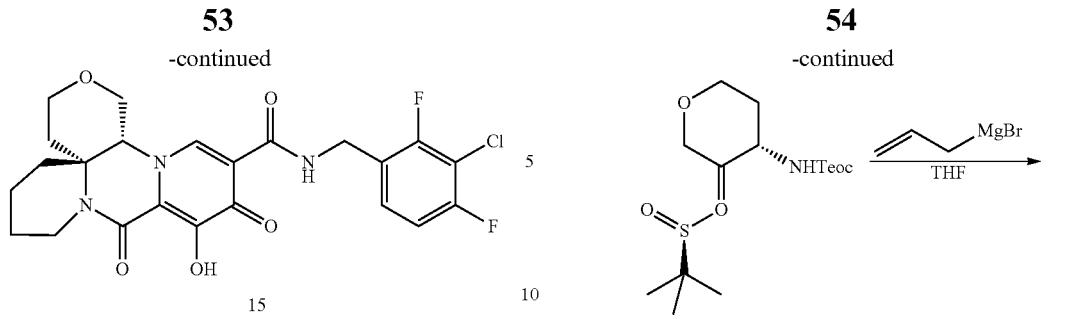

15

Step 1

A mixture of compound 13 (32 mg, 0.063 mmol) and 10% palladium on carbon (5 mg, 0.174 mmol) in ethanol (2 mL) was stirred under hydrogen atmosphere. After 2 h, the reaction mixture was filtered through celite pad and the celite was washed with ethanol. The combined filtrate and the washing were concentrated to dryness to get the crude saturated product, which was used for the next reaction: LCMS-ESI$^+$ (m/z): [M+H]$^+$ calculated for $C_{24}H_{25}ClF_2N_3O_5$: 508.15. found: 508.14.

To a solution of the above crude saturated product in MeCN (3 mL) was added magnesium bromide (32 mg, 0.174 mmol) at room temperature and the resulting mixture was stirred for 30 min at 50° C. bath. The reaction mixture was stirred at 0° C. and added 1 N HCl (~7 drops) to make the mixture a solution. After the solution was diluted with water, the product was extracted with dichloromethane (×3). The combined extracts were dried (MgSO$_4$) and concentrated. The residue was purified by column chromatography on silica gel (12 g column) using dichloromethane-20% methanol in dichloromethane as eluents to get compound 15: $^1$H NMR (400 MHz, Chloroform-d) δ 12.60 (s, 1H), 10.45 (s, 1H), 8.37 (s, 1H), 7.26 (m, 1H), 6.92 (td, J=8.5, 1.8 Hz, 1H), 5.85-5.61 (m, 2H), 5.19 (d, J=18.0 Hz, 1H), 4.67 (d, J=5.8 Hz, 2H), 4.13 (s, 1H), 4.00-3.85 (m, 2H), 3.72-3.54 (m, 2H), 3.49 (d, J=18.8 Hz, 1H), 2.57 (dd, J=20.6, 15.2 Hz, 2H), 1.99 (d, J=16.7 Hz, 1H), 1.75 (ddd, J=16.2, 12.4, 4.5 Hz, 1H). $^{19}$F NMR (376 MHz, Chloroform-d) δ −115.09 (s, 1F), −117.30 (s, 1F). LCMS-ESI$^+$ (m/z): [M+H]$^+$ calculated for $C_{23}H_{21}ClF_2N_3O_5$: 492.11. found: 492.15.

Example 3

Preparation of Compound 25

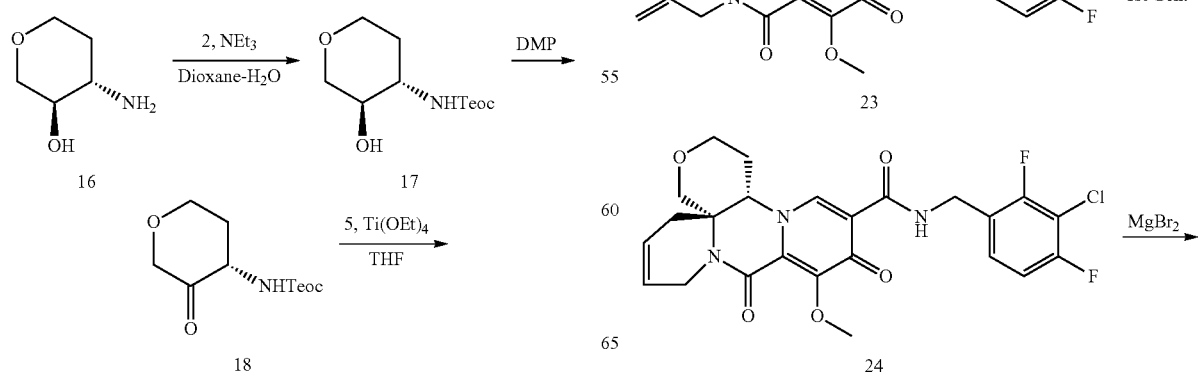

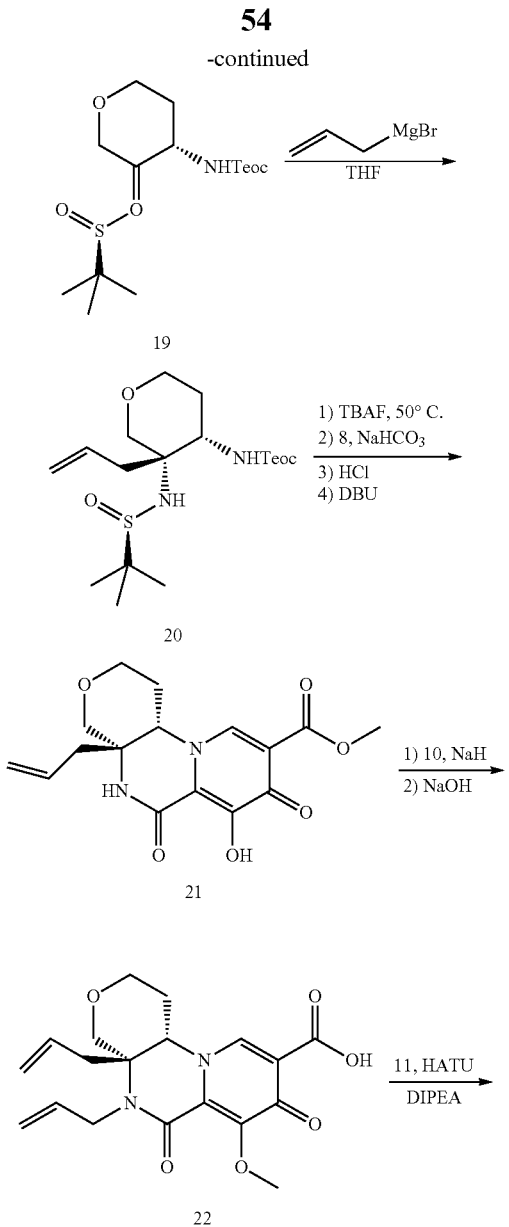

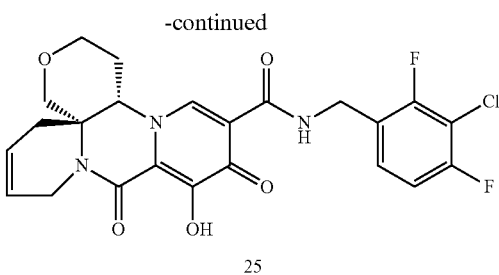

25

Step 1

A solution of compound 16 (4.00 g, 26.04 mmol) and triethylamine (5.44 mL, 39.06 mmol) in water (35 mL) and 1,4-dioxane (35 mL) was stirred at room temperature as compound 2 (7.428 g, 28.64 mmol) was added. The resulting mixture was stirred at room temperature overnight. After 16 h, the reaction mixture was diluted with water (~125 mL) and extracted with ethyl acetate (~125 mL×2). The extracts were washed with water (125 mL×1), combined, dried ($Na_2SO_4$), and concentrated. The residue was purified by column chromatography on silica gel (120 g column used with cartridge) using hexanes-ethyl acetate as eluents to get compound 17: $^1$H NMR (400 MHz, Chloroform-d) δ 4.68 (s, 1H), 4.23-4.13 (m, 2H), 4.01 (ddd, J=11.4, 4.8, 1.1 Hz, 1H), 3.92 (dd, J=12.0, 4.8 Hz, 1H), 3.56 (ddd, J=12.3, 9.7, 5.4 Hz, 1H), 3.48 (td, J=9.3, 4.8 Hz, 1H), 3.41 (td, J=11.9, 2.3 Hz, 1H), 3.14 (dd, J=11.4, 9.5 Hz, 1H), 1.99-1.87 (m, 1H), 1.55 (dtd, J=13.2, 11.6, 4.8 Hz, 1H), 1.06-0.91 (m, 2H), 0.04 (s, 9H). LCMS-ESI$^+$ (m/z): [M+H—$C_2H_4$]$^+$ calculated for $C_9H_{20}NO_4Si$: 234.12. found: 233.95.

Step 2

A solution of compound 17 (6.430 g, 24.6 mmol) in dichloromethane (125 mL) was stirred at 0° C. (some reactant precipitated) as Dess-Martin periodinane (12.52 g, 29.52 mmol) was added in portion. After 15 min, the mixture was stirred at room temperature for 7 h. The reaction mixture was filtered to remove the precipitate, and the solids were washed with dichloromethane. The filtrate and washing layers were concentrated and purified by column chromatography on silica gel (120 g column) using hexanes-ethyl acetate as eluents to get compound 18: $^1$H NMR (400 MHz, Chloroform-d) δ 5.48 (s, 1H), 4.49 (dt, J=12.8, 6.6 Hz, 1H), 4.22-4.09 (m, 3H), 4.09-3.98 (m, 2H), 3.90 (td, J=11.7, 3.2 Hz, 1H), 2.84-2.61 (m, 1H), 1.89 (dddd, J=13.1, 12.1, 10.4, 5.4 Hz, 1H), 1.06-0.93 (m, 2H), 0.04 (s, 9H). LCMS-ESI$^+$ (m/z): [M+H—$C_2H_4$]$^+$ calculated for $C_9H_{18}NO_4Si$: 232.10. found: 231.83.

Step 3

To a solution of compound 18 (1.500 g, 5.789 mmol) and (R)-tert-butylsulfiamide (5, 841.11 mg, 6.94 mmol) in THF (10 mL) was added titanium tetraethoxide (2.452 mL, 11.7 mmol) at room temperature. The resulting solution was stirred at room temperature overnight. The reaction mixture was poured into a stirred mixture of ethyl acetate (~20 mL) and aqueous saturated $NaHCO_3$ (~15 mL). After some celite was added to the mixture, it was filtered through celite pad, and the pad was washed with ethyl acetate. The combined filtrate and washing layers was dried ($MgSO_4$) and concentrated. The residue was purified by column chromatography on silica gel (40 g column) using ethyl acetate-20% methanol in ethyl acetate as eluents to obtain compound 19: $^1$H NMR (400 MHz, Chloroform-d) δ 5.41 (d, J=14.4 Hz, 1H), 4.53 (d, J=10.0 Hz, 1H), 4.26-4.07 (m, 3H), 3.97 (d, J=11.1 Hz, 1H), 3.85-3.67 (m, 1H), 2.58 (d, J=8.6 Hz, 1H), 1.84 (qd, J=12.0, 5.4 Hz, 1H), 1.65-1.53 (m, 1H), 1.25 (s, 9H), 0.99 (td, J=8.9, 8.3, 4.7 Hz, 2H), 0.04 (s, 9H). LCMS-ESI$^+$ (m/z): [M+H—$C_2H_4$]$^+$ calculated for $C_{13}H_{27}N_2O_4SSi$: 335.15. found: 334.86.

Step 4

A solution of compound 19 (1125 mg, 3.103 mmol) in THF (12 mL) was stirred in a ~78° C. bath, as allylmagnesium bromide (1 M in ether, 9.31 mL) was added over 4 min. After 40 min, the temperature of the bath became −60° C. and the reaction mixture was removed from the bath and stirred for 30 min at room temperature. The reaction mixture was diluted with saturated $NH_4Cl$ with some water and extracted with ethyl acetate (~25 mL×2). After the extracts were washed with water (×2), the combined extracts were dried ($Na_2SO_4$) and concentrated. The residue was purified by column chromatography on silica gel (80 g column) using hexanes-ethyl acetate as eluents to get compound 20: $^1$H NMR (400 MHz, Chloroform-d) δ 6.78 (d, J=10.2 Hz, 1H), 5.85-5.65 (m, 1H), 5.17-5.01 (m, 2H), 4.17 (ddd, J=17.5, 10.3, 6.6 Hz, 2H), 3.98 (dd, J=11.7, 5.0 Hz, 1H), 3.84 (ddd, J=12.2, 10.2, 4.6 Hz, 1H), 3.74-3.60 (m, 1H), 3.55-3.39 (m, 1H), 3.37 (d, J=11.7 Hz, 1H), 2.67 (dd, J=15.0, 7.0 Hz, 1H), 2.45-2.27 (m, 1H), 1.83 (tt, J=12.7, 6.5 Hz, 1H), 1.76-1.53 (m, 2H), 1.28 (s, 9H), 1.01 (dt, J=10.2, 6.4 Hz, 2H), 0.03 (s, 10H). LCMS-ESI$^+$ (m/z): [M+H]$^+$ calculated for $C_{16}H_{33}N_2O_4SSi$: 377.19. found: 376.98.

Step 5

To a mixture of compound 20 (939 mg, 2.321 mmol) and tetrabutylammonium fluoride hydrate (2594.2 mg, 9.282 mmol) was added acetonitrile (10 mL) and the reaction was stirred overnight at 50° C. The reaction mixture was acidified with 2 N HCl and neutralized with ~1 mL saturated $NaHCO_3$. The resulting solution was concentrated and dried under vacuum.

To the crude residue, were added compound 8 (562 mg, 2.321 mmol), $NaHCO_3$ (389.89 mg, 4.641 mmol), water (5 mL), and methanol (8 mL). The resulting mixture was stirred at room temperature for 1 h. The reaction mixture was concentrated to remove most of the solvent. After the residue was dissolved in dichloromethane (~50 mL) and dried ($MgSO_4$), the insoluble material was filtered off and the filtrate was concentrated. The residue was dissolved in dichloromethane (12 mL) and treated with 4 N HCl in dioxane (12 mL) at room temperature. After 2 h, the reaction mixture was concentrated to remove the solvent and the residue was partially purified by column chromatography on silica gel (80 g column) using ethyl acetate-20% methanol in ethyl acetate as eluents. Partially purified product was further purified by preparative HPLC (acetonitrile/$H_2O$ with 0.1% TFA modifier) and the product containing fractions were pooled and freeze-dried to obtain compound 21: $^1$H NMR (400 MHz, Chloroform-d) δ 8.76 (s, 1H), 6.31 (s, 1H), 5.62 (d, J=7.8 Hz, 1H), 5.19 (d, J=10.2 Hz, 1H), 5.08 (d, J=17.0 Hz, 1H), 4.65 (s, 1H), 4.13 (s, 4H), 3.98 (s, 3H), 3.86 (d, J=13.2 Hz, 1H), 3.52 (t, J=11.8 Hz, 2H), 2.35 (dd, J=14.2, 6.6 Hz, 1H), 2.30-2.05 (m, 3H). LCMS-ESI$^+$ (m/z): [M+H]$^+$ calculated for $C_{17}H_{21}N_2O_6$: 349.14. found: 349.13.

Step 6

A mixture of compound 21 (376 mg, 1.079 mmol) and 60% NaH (173 mg, 4.317 mmol) was cooled at 0° C. as DMF (5 mL) was added to the mixture. After 5 min, allyl bromide (0.231 mL, 2.666 mmol) was added. After 10 min, 2 N NaOH (0.6 mL) was added and stirred at 0° C. for 10 min. The reaction mixture was then acidified with 2 N HCl (~2.5 mL) and the acidified reaction mixture was concentrated to remove solvents. The residue was dissolved in water and purified by preparative HPLC (acetonitrile/$H_2O$ with 0.1% TFA modifier). The product containing fractions were pooled and freeze-dried to obtain compound 22: $^1$H NMR (400 MHz, Chloroform-d) δ 8.33 (s, 1H), 5.93 (dq, J=14.7, 5.2, 4.5 Hz, 1H), 5.61-5.45 (m, 1H), 5.36 (d, J=17.2 Hz, 1H), 5.27 (d, J=10.0 Hz, 1H), 5.14 (d, J=10.0 Hz, 1H), 4.93 (dd, J=16.2, 8.2 Hz, 2H), 4.36 (d, J=13.5 Hz, 1H), 4.13 (s, 5H), 3.99 (dd, J=15.8, 8.8 Hz, 1H), 3.65-3.49 (m, 1H), 3.42 (d, J=13.7 Hz, 1H), 2.37 (dd, J=14.5, 6.7 Hz, 1H), 2.29-2.04 (m, 2H), 1.96 (d, J=13.5 Hz, 1H). LCMS-ESI$^+$ (m/z): [M+H]$^+$ calculated for $C_{19}H_{23}N_2O_6$: 375.16. found: 375.15.

Step 7

A mixture of compound 22 (141 mg, 0.377 mmol), compound 11 (89 mg, 0.414 mmol), and HATU (286.38 mg, 0.753 mmol) in dichloromethane (5 mL) was stirred at room temperature as N,N-diisopropylethylamine (0.7 mL, 4.011 mmol) was added. After 30 min, the reaction mixture was diluted with ethyl acetate and washed with saturated NH$_4$Cl (×2), saturated NaHCO$_3$ (×2), and brine (×1). After the aqueous fractions were extracted with ethyl acetate (×1), the organic fractions were combined, dried (Na$_2$SO$_4$) and concentrated. The residue was purified by column chromatography on silica gel (24 g column) using hexanes-ethyl acetate-20% methanol in ethyl acetate as eluents to get compound 23: $^1$H NMR (400 MHz, Chloroform-d) δ 10.51 (t, J=6.0 Hz, 1H), 8.36 (s, 1H), 7.21 (td, J=8.3, 5.9 Hz, 1H), 6.86 (td, J=8.5, 1.8 Hz, 1H), 5.87 (dddd, J=17.3, 10.1, 8.7, 4.3 Hz, 1H), 5.45 (dddd, J=17.1, 10.1, 8.3, 7.0 Hz, 1H), 5.32-5.21 (m, 1H), 5.17 (d, J=10.2 Hz, 1H), 5.06-4.98 (m, 1H), 4.86 (dd, J=16.8, 1.5 Hz, 1H), 4.82-4.74 (m, 1H), 4.57 (dd, J=6.1, 2.2 Hz, 2H), 4.26 (d, J=13.7 Hz, 1H), 4.19 (dd, J=12.0, 4.7 Hz, 1H), 4.00 (s, 1H), 3.98 (s, 3H), 3.93 (dd, J=15.8, 8.8 Hz, 1H), 3.48 (td, J=12.2, 2.4 Hz, 1H), 3.34 (d, J=13.7 Hz, 1H), 2.27 (dd, J=14.4, 7.1 Hz, 1H), 2.15 (dd, J=14.4, 8.2 Hz, 1H), 2.11-1.98 (m, 1H), 1.93-1.82 (m, 1H). LCMS-ESI$^+$ (m/z): [M+H]$^+$ calculated for $C_{26}H_{27}ClF_2N_3O_5$: 534.16. found: 534.19.

Step 8

A solution of compound 23 (142 mg, 0.266 mmol) in dichloromethane (26 mL) was stirred in an ice bath while Ar gas was bubbled through. After 20 min, Grubbs Catalyst 1$^{st}$ generation (20 mg, 26.59 μmol) was added and the Ar bubbling continued for 15 min. Then, the reaction mixture was refluxed at 50° C. After 2 h, the reaction mixture was concentrated and purified by column chromatography on silica gel (24 g column) using hexanes-ethyl acetate-20% methanol in ethyl acetate as eluents to get compound 24: $^1$H NMR (400 MHz, Chloroform-d) δ 10.43 (t, J=6.0 Hz, 1H), 8.43 (s, 1H), 7.35-7.21 (m, 1H), 6.92 (td, J=8.5, 1.8 Hz, 1H), 5.72 (d, J=3.2 Hz, 2H), 5.20-5.04 (m, 1H), 4.73-4.56 (m, 2H), 4.18-4.09 (m, 1H), 4.03 (d, J=0.9 Hz, 3H), 3.92 (td, J=14.0, 12.9, 4.7 Hz, 2H), 3.68 (t, J=11.3 Hz, 1H), 3.63-3.53 (m, 1H), 3.47 (dt, J=19.2, 3.7 Hz, 1H), 2.57-2.40 (m, 2H), 1.99-1.86 (m, 1H), 1.68 (ddd, J=16.0, 12.4, 4.4 Hz, 1H). $^{19}$F NMR (377 MHz, Chloroform-d) δ −114.68--115.04 (m, 1F), −117.28 (d, J=7.9 Hz, 1F). LCMS-ESI$^+$ (m/z): [M+H]$^+$ calculated for $C_{24}H_{23}ClF_2N_3O_5$: 506.13. found: 506.16.

Step 9

To a solution of compound 24 (15 mg, 0.03 mmol) in MeCN (1.4 mL) was added magnesium bromide (14.19 mg, 0.077 mmol) at room temperature and the resulting mixture was stirred at 50° C. After 30 min, the reaction mixture was stirred at 0° C. and 1 N HCl was add to make the mixture a solution, and diluted with water before extraction with CH$_2$Cl$_2$ (×3). The combined extracts were dried (MgSO$_4$) and concentrated. The residue was purified by column chromatography on silica gel (12 g column) using dichloromethane-20% methanol in dichloromethane as eluents.

The sample was dissolved in dioxane and freeze-dried to get compound 25: $^1$H NMR (400 MHz, Chloroform-d) δ 12.85 (s, 1H), 10.48 (t, J=6.1 Hz, 1H), 8.39 (s, 1H), 7.40-7.14 (m, 1H), 6.91 (td, J=8.5, 1.8 Hz, 1H), 4.64 (dd, J=17.4, 5.7 Hz, 3H), 4.08-3.98 (m, 1H), 3.87 (ddd, J=16.9, 11.7, 6.9 Hz, 2H), 3.65 (t, J=11.2 Hz, 1H), 3.61-3.52 (m, 1H), 3.03 (td, J=13.4, 3.1 Hz, 1H), 2.70 (d, J=15.7 Hz, 1H), 1.92 (ddd, J=19.2, 9.3, 4.7 Hz, 1H), 1.83-1.67 (m, 4H), 1.58 (m, 2H). $^{19}$F NMR (376 MHz, Chloroform-d) δ −115.18 (q, J=6.5, 5.4 Hz, 1F), −117.36 (dd, J=8.0, 3.3 Hz, 1F). LCMS-ESI$^+$ (m/z): [M+H]$^+$ calculated for $C_{23}H_{21}ClF_2N_3O_5$: 492.11. found: 492.15.

Example 4

Preparation of Compound 26

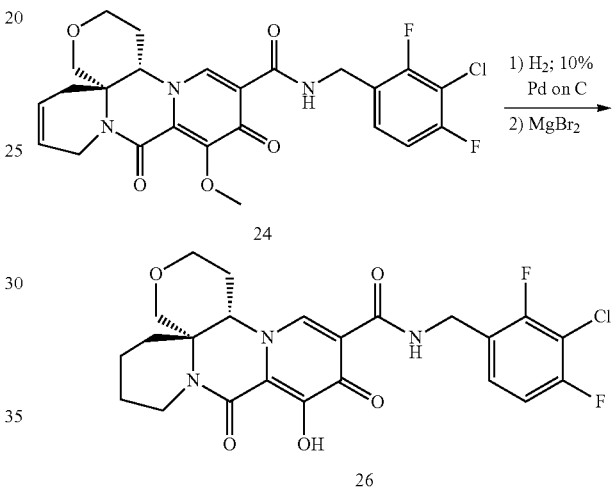

Step 1

To a solution of compound 24 (105 mg, 0.208 mmol) in ethanol (5 mL) was added 10% palladium on carbon (18.2 mg) and the resulting mixture was stirred under hydrogen atmosphere. After 2 h, the reaction mixture was filtered through celite pad and washed with ethanol. The filtrate was concentrated and dried in vacuum. The residue was dissolved in acetonitrile (10 mL) and magnesium bromide (98.96 mg, 0.573 mmol) was added to the solution at room temperature. The resulting mixture was stirred at 50° C. for 30 min. The reaction mixture was stirred at 0° C. and 1 N HCl was added to make the mixture a solution. The resulting solution was further diluted with water before the product was extracted with dichloromethane (×3). The combined extracts were dried (MgSO$_4$) and concentrated. The residue was purified by column chromatography on silica gel (12 g column) using dichloromethane-20% methanol in dichloromethane as eluents to get compound 26: $^1$H NMR (400 MHz, Chloroform-d) δ 12.85 (s, 1H), 10.48 (t, J=6.1 Hz, 1H), 8.39 (s, 1H), 7.40-7.14 (m, 1H), 6.91 (td, J=8.5, 1.8 Hz, 1H), 4.64 (dd, J=17.4, 5.7 Hz, 3H), 4.08-3.98 (m, 1H), 3.87 (ddd, J=16.9, 11.7, 6.9 Hz, 2H), 3.65 (t, J=11.2 Hz, 1H), 3.61-3.52 (m, 1H), 3.03 (td, J=13.4, 3.1 Hz, 1H), 2.70 (d, J=15.7 Hz, 1H), 1.92 (ddd, J=19.2, 9.3, 4.7 Hz, 1H), 1.83-1.67 (m, 4H), 1.58 (m, 2H). $^{19}$F NMR (376 MHz, Chloroform-d) δ −115.18 (q, J=6.5, 5.4 Hz, 1F), −117.36 (dd, J=8.0, 3.3 Hz, 1F). LCMS-ESI$^+$ (m/z): [M+H]$^+$ calculated for $C_{23}H_{23}ClF_2N_3O_5$: 494.13. found: 494.17.

Example 5

Preparation of Compound 30

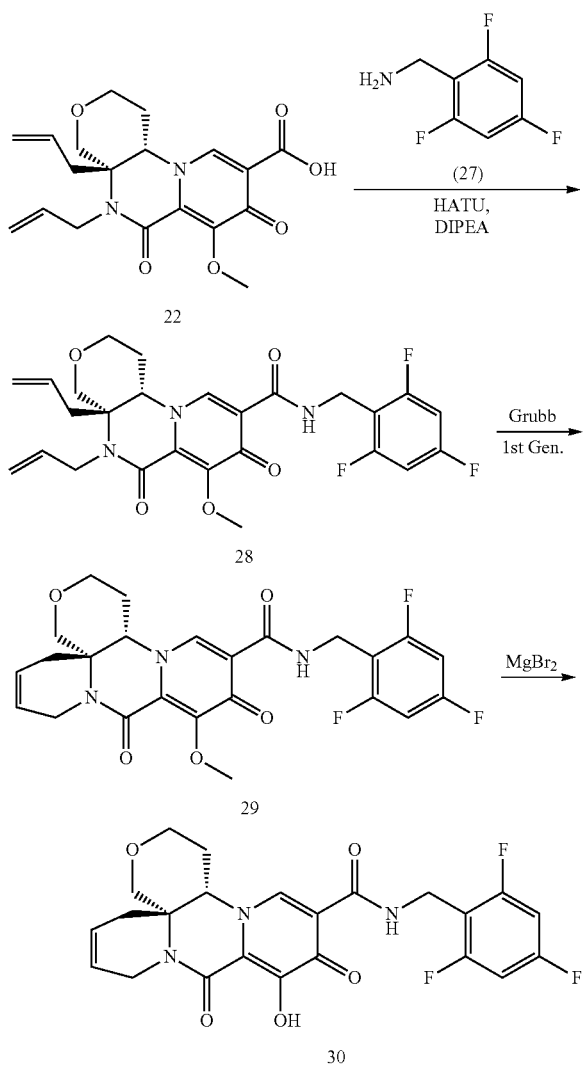

Step 1

A mixture of 22 (144 mg, 0.385 mmol), 2,4,6-trifluorobenzylamine (27, 68.17 mg, 0.423 mmol), and HATU (292.47 mg, 0.769 mmol) in dichloromethane (5 mL) was stirred at room temperature as N,N-diisopropylethylamine (0.713 mL, 4.096 mmol) was added. After 30 min, the reaction mixture was diluted with ethyl acetate, washed with saturated $NH_4Cl$ (×2), saturated $NaHCO_3$ (×2), and brine (×1). After the aqueous fractions were extracted with ethyl acetate (×1), the organic fractions were combined, dried ($Na_2SO_4$), and concentrated. The residue was purified by column chromatography on silica gel (24 g column) using hexanes-ethyl acetate-20% methanol in ethyl acetate as eluents to obtain compound 28: $^1$H NMR (400 MHz, Chloroform-d) δ 10.36 (s, 1H), 8.31 (s, 1H), 6.66 (dd, J=8.8, 7.4 Hz, 2H), 5.93 (dddd, J=17.3, 10.2, 8.8, 4.2 Hz, 1H), 5.50 (dddd, J=16.9, 10.1, 8.4, 6.8 Hz, 1H), 5.39-5.27 (m, 1H), 5.24 (d, J=10.1 Hz, 1H), 5.12 (dd, J=9.9, 1.4 Hz, 1H), 4.97-4.84 (m, 2H), 4.66 (dd, J=5.5, 2.0 Hz, 2H), 4.33 (d, J=13.6 Hz, 1H), 4.11 (dt, J=14.9, 7.4 Hz, 3H), 4.05 (s, 3H), 3.98 (dd, J=15.8, 8.8 Hz, 1H), 3.53 (td, J=12.3, 2.4 Hz, 1H), 3.39 (d, J=13.6 Hz, 1H), 2.33 (dd, J=14.4, 6.9 Hz, 1H), 2.19 (dd, J=14.4, 8.5 Hz, 1H), 2.16-2.05 (m, 1H), 1.97-1.85 (m, 1H). LCMS-ESI$^+$ (m/z): [M+H]+ calculated for $C_{26}H_{27}F_3N_3O_5$: 518.19. found: 518.20.

Step 2

A solution of compound 28 (164 mg, 0.317 mmol) in dichloromethane (32 mL, ~10 mM) was stirred in an ice bath while Ar gas was bubbled through. After 30 min, Grubbs Catalyst 1$^{st}$ generation (23.83 mg, 31.69 μmol) was added and the Ar bubbling continued for 15 min. Then, the reaction mixture was refluxed at 50° C. bath. After 1 h, the reaction mixture was concentrated and purified by column chromatography on silica gel (24 g column) using hexanes-ethyl acetate-20% methanol in ethyl acetate as eluents to get compound 29. $^1$H NMR (400 MHz, Chloroform-d) δ 10.32 (s, 1H), 8.38 (s, 1H), 6.80-6.54 (m, 2H), 5.71 (dddd, J=41.1, 10.1, 4.6, 2.2 Hz, 2H), 5.30 (s, 1H), 5.11 (d, J=18.5 Hz, 1H), 4.66 (dd, J=5.7, 3.3 Hz, 2H), 4.48 (dd, J=13.4, 1.3 Hz, 1H), 4.24-4.04 (m, 3H), 3.77-3.64 (m, 1H), 3.66-3.52 (m, 1H), 3.16 (d, J=13.4 Hz, 1H), 2.51-2.34 (m, 1H), 2.25 (qd, J=12.5, 5.4 Hz, 1H), 2.04 (s, 2H), 1.93 (d, J=13.6 Hz, 1H), 1.79 (d, J=17.5 Hz, 1H), 1.26 (t, J=7.1 Hz, 2H). LCMS-ESI$^+$ (m/z): [M+H]$^+$ calculated for $C_{24}H_{23}F_3N_3O_5$: 490.16. found: 490.18.

Step 3

To a solution of compound 29 (18 mg, 0.037 mmol) in acetonitrile (1.4 mL) was added magnesium bromide (17.6 mg, 0.096 mmol) at room temperature and the resulting mixture was stirred at 50° C. bath. After 30 min, the reaction mixture was stirred at 0° C. and 1 N HCl was added to make the mixture a solution. The resulting solution was further diluted with water before the product was extracted with dichloromethane (×3). The combined extracts were dried ($MgSO_4$) and concentrated. The residue was purified by column chromatography on silica gel (12 g column) using dichloromethane-20% methanol in dichloromethane as eluents. The sample was dissolved in dioxane and freeze-dried to get compound 30: $^1$H NMR (400 MHz, Chloroform-d) δ 12.64 (s, 1H), 10.36 (t, J=5.7 Hz, 1H), 8.35 (s, 1H), 6.74-6.52 (m, 2H), 5.87-5.61 (m, 2H), 5.25-5.02 (m, 1H), 4.66 (dd, J=5.8, 2.8 Hz, 2H), 4.50 (d, J=13.5 Hz, 1H), 4.09 (ddt, J=16.4, 11.1, 4.9 Hz, 2H), 3.81-3.50 (m, 2H), 3.21 (d, J=13.6 Hz, 1H), 2.50 (ddd, J=17.6, 4.3, 2.2 Hz, 1H), 2.19 (qd, J=12.4, 5.3 Hz, 1H), 1.97-1.79 (m, 2H). LCMS-ESI$^+$ (m/z): [M+H]$^+$ calculated for $C_{23}H_{21}F_3N_3O_5$: 476.14. found: 476.16.

Example 6

Preparation of Compound 31

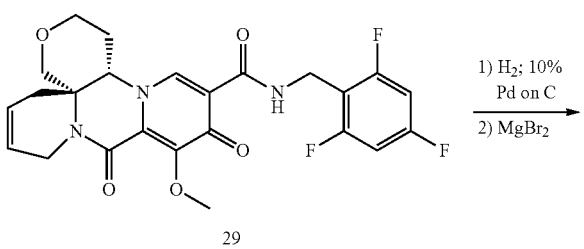

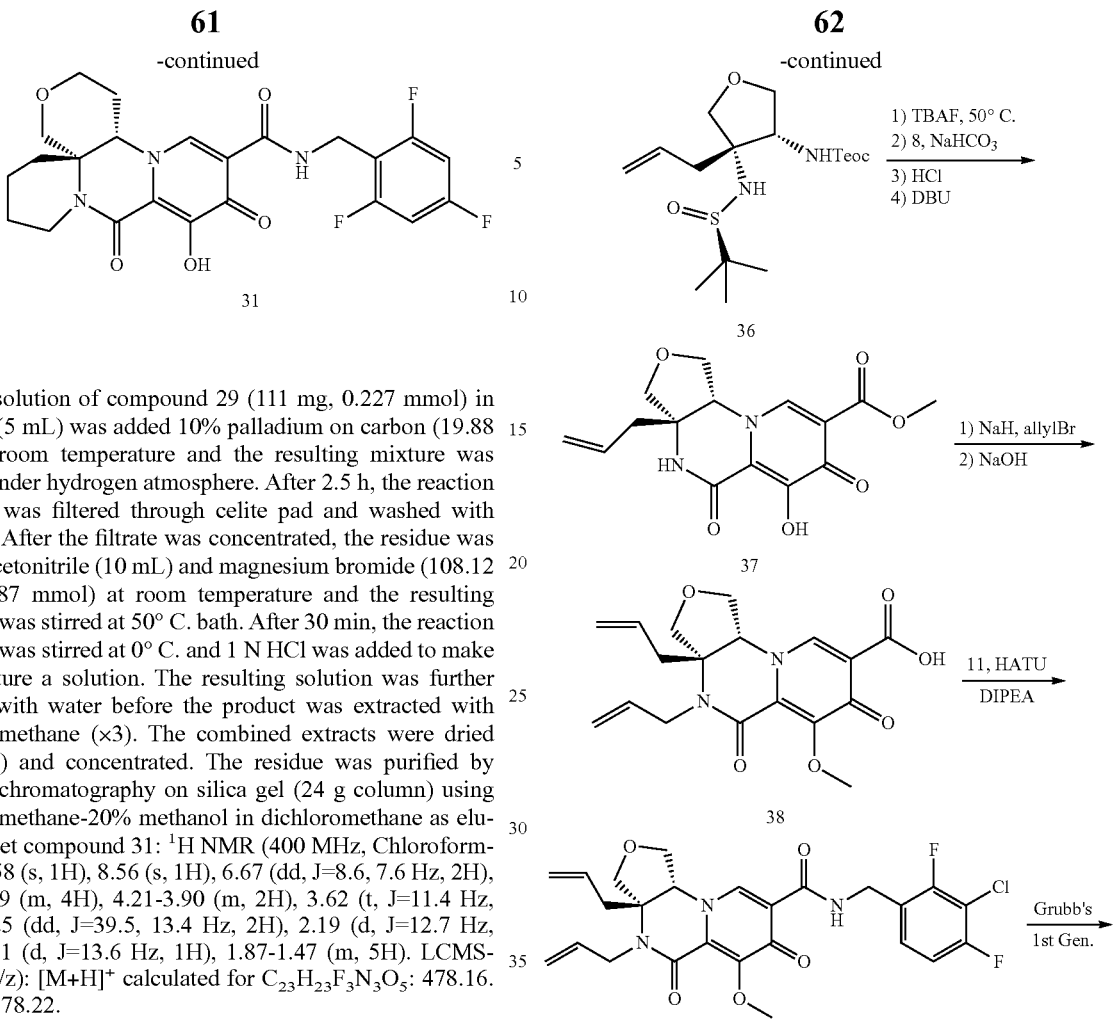

Step 1

To a solution of compound 29 (111 mg, 0.227 mmol) in ethanol (5 mL) was added 10% palladium on carbon (19.88 mg) at room temperature and the resulting mixture was stirred under hydrogen atmosphere. After 2.5 h, the reaction mixture was filtered through celite pad and washed with ethanol. After the filtrate was concentrated, the residue was added acetonitrile (10 mL) and magnesium bromide (108.12 mg, 0.587 mmol) at room temperature and the resulting mixture was stirred at 50° C. bath. After 30 min, the reaction mixture was stirred at 0° C. and 1 N HCl was added to make the mixture a solution. The resulting solution was further diluted with water before the product was extracted with dichloromethane (×3). The combined extracts were dried (MgSO$_4$) and concentrated. The residue was purified by column chromatography on silica gel (24 g column) using dichloromethane-20% methanol in dichloromethane as eluents to get compound 31: $^1$H NMR (400 MHz, Chloroform-d) δ 10.58 (s, 1H), 8.56 (s, 1H), 6.67 (dd, J=8.6, 7.6 Hz, 2H), 4.88-4.49 (m, 4H), 4.21-3.90 (m, 2H), 3.62 (t, J=11.4 Hz, 1H), 3.25 (dd, J=39.5, 13.4 Hz, 2H), 2.19 (d, J=12.7 Hz, 1H), 1.91 (d, J=13.6 Hz, 1H), 1.87-1.47 (m, 5H). LCMS-ESI$^+$ (m/z): [M+H]$^+$ calculated for C$_{23}$H$_{23}$F$_3$N$_3$O$_5$: 478.16. found: 478.22.

Example 7

Preparation of Compound 41

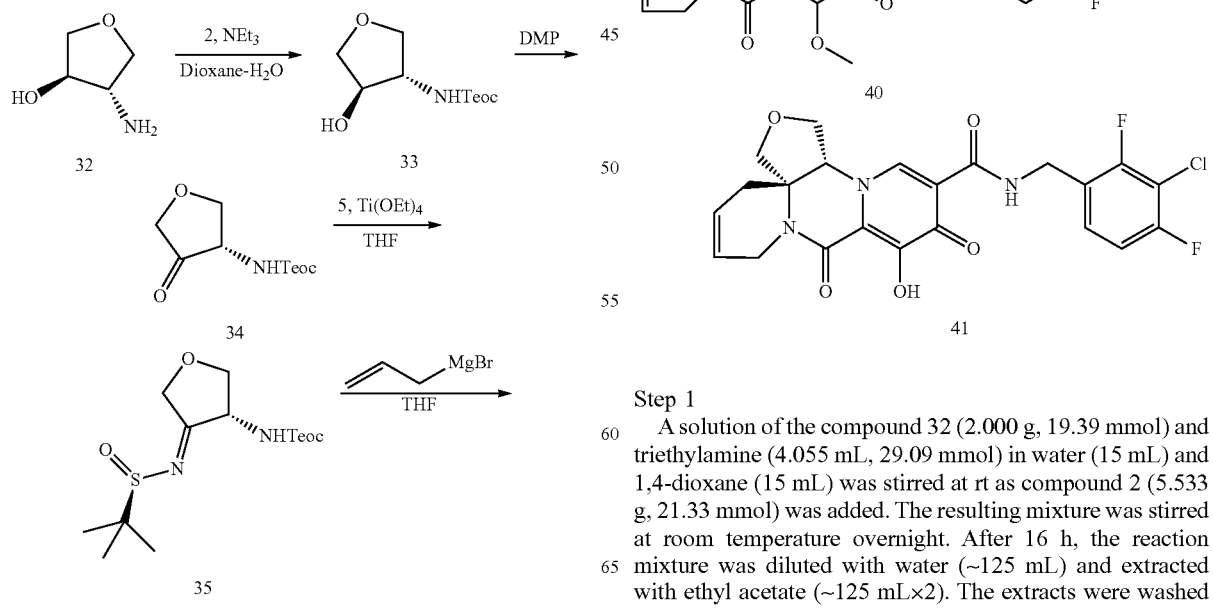

Step 1

A solution of the compound 32 (2.000 g, 19.39 mmol) and triethylamine (4.055 mL, 29.09 mmol) in water (15 mL) and 1,4-dioxane (15 mL) was stirred at rt as compound 2 (5.533 g, 21.33 mmol) was added. The resulting mixture was stirred at room temperature overnight. After 16 h, the reaction mixture was diluted with water (~125 mL) and extracted with ethyl acetate (~125 mL×2). The extracts were washed with water (125 mL×1), combined, dried (Na$_2$SO$_4$), and concentrated. The residue was purified by column chromatography on silica gel (120 g column) using hexanes-ethyl acetate as eluents to get compound 33: $^1$H NMR (400 MHz, Chloroform-d) δ 4.86 (d, J=6.3 Hz, 1H), 4.30 (dt, J=5.1, 2.5 Hz, 1H), 4.16 (dd, J=12.3, 4.9 Hz, 2H), 4.07-4.03 (m, 2H), 3.99 (tt, J=5.3, 2.2 Hz, 1H), 3.67 (ddd, J=20.4, 9.7, 2.9 Hz, 2H), 2.71 (s, 1H), 1.05-0.91 (m, 2H), 0.04 (s, 9H).

Step 2

A solution of compound 33 (4.191 g, 16.94 mmol) in dichloromethane (80 mL) was stirred at 0° C. (some reactant precipitated) as Dess-Martin periodinane (8.623 g, 20.33 mmol) was added in portion. After 15 min, the mixture (almost a solution) was stirred at room temperature. After 7.5 h, the reaction mixture was filtered to remove the precipitate, and the solids were washed with dichloromethane. The filtrate and washing layers were concentrated and purified by column chromatography on silica gel (120 g column) using ethyl acetate-20% methanol in ethyl acetate as eluents to get the ketone 34: $^1$H NMR (400 MHz, Chloroform-d) δ 5.07 (s, 1H), 4.67 (t, J=8.9 Hz, 1H), 4.22-4.13 (m, 4H), 3.93 (d, J=17.5 Hz, 1H), 3.80 (t, J=9.7 Hz, 1H), 1.07-0.91 (m, 2H), 0.04 (s, 9H).

Step 3

To a solution of compound 34 (1.812 g, 7.385 mmol) and compound 5 (1.074 g, 8.863 mmol) in THF (15 mL) was added titanium tetraethoxide (3.132 mL, 14.94 mmol) at room temperature. The resulting solution was stirred at room temperature overnight. The reaction mixture was poured into a stirred mixture of ethyl acetate (~20 mL) and saturated NaHCO$_3$ (~15 mL). After some celite was added to the mixture, it was filtered through celite pad, and the celite pad was washed with ethyl acetate. After the combined filtrate and washing was dried (MgSO$_4$) and concentrated, the residue was purified by column chromatography on silica gel (80 g column) using dichloromethane-ethyl acetate as eluents to obtain compound 35: $^1$H NMR (400 MHz, Chloroform-d) δ 5.07 (s, 1H), 5.01 (d, J=18.2 Hz, 1H), 4.54 (s, 1H), 4.46 (d, J=18.1 Hz, 1H), 4.22-4.14 (m, 2H), 3.44-3.29 (m, 1H), 1.30-1.23 (m, 9H), 1.06-0.94 (m, 2H), 0.04 (s, 9H). LCMS-ESI$^+$ (m/z): [M+H—C$_2$H$_4$]$^+$ calculated for C$_{12}$H$_{25}$N$_2$O$_4$SSi: 321.13. found: 320.82.

Step 4

A solution of compound 35 (1.604 g, 4.602 mmol) in THF (15 mL) was stirred in an acetone-dry ice bath as allylmagnesium bromide (1 M in ether, 13.81 mL) was added over ~4 min. After 40 min, the temperature of the bath became ~−55° C. and the reaction mixture was removed from the bath. After 30 min, saturated NH$_4$Cl was added to the reaction mixture with some water. The mixture was extracted with ethyl acetate (~25 mL×2) and the extracts were washed with water (×2). The combined extracts were dried (Na$_2$SO$_4$) and concentrated. The residue was purified by column chromatography on silica gel (80 g column) using hexanes-ethyl acetate as eluents to get compound 36: $^1$H NMR (400 MHz, Chloroform-d) δ 6.36 (s, 1H), 5.92-5.68 (m, 1H), 5.26-5.11 (m, 2H), 4.31 (t, J=8.7 Hz, 1H), 4.22-4.12 (m, 3H), 3.85 (d, J=9.5 Hz, 1H), 3.82-3.74 (m, 2H), 3.53 (t, J=8.6 Hz, 1H), 2.70 (dd, J=14.8, 7.2 Hz, 1H), 2.56-2.38 (m, 1H), 1.49-1.33 (m, 1H), 1.25 (s, 9H), 0.03 (s, 9H). LCMS-ESI$^+$ (m/z): [M+H—C$_2$H$_4$]$^+$ calculated for C$_{16}$H$_{31}$N$_2$O$_4$SSi: 363.18. found: 362.95.

Step 5

To a mixture of compound 36 (906 mg, 2.319 mmol) and tetrabutylammonium fluoride hydrate (2592.9 mg, 9.278 mmol) was added acetonitrile (10 mL) and stirred overnight at 50° C. The reaction mixture was acidified with 2 N HCl and neutralized with ~1 mL saturated NaHCO$_3$. The resulting solution was concentrated and dried in vacuum. A mixture of the crude residue, compound 8 (540 mg, 2.231 mmol), and NaHCO$_3$ (389.7 mg, 4.639 mmol) in water (5 mL) and MeOH (8 mL) was stirred at room temperature for 1 h. The reaction mixture was concentrated to remove most of the solvent. After the residue was dissolved in dichloromethane (~50 mL) and dried (MgSO$_4$), the insoluble material was filtered off and the filtrate was concentrated. The residue was dissolved in dichloromethane (12 mL) and treated 4 N HCl in dioxane (12 mL) at room temperature for 2 h. After the reaction mixture was concentrated, the residue was dissolved in methanol (20 mL) and DBU (1.734 mL, 11.6 mmol) was added to the solution. After the resulting mixture was stirred at 50° C. for 15 min, the reaction mixture was concentrated and solvent was co-evaporated with toluene. The residue was purified by column chromatography on silica gel (80 g column) using ethyl acetate-methanol in ethyl acetate as eluents to obtain compound 37: $^1$H NMR (400 MHz, Chloroform-d) δ 8.09 (s, 1H), 5.99 (s, 1H), 5.28-5.15 (m, 2H), 4.56-4.32 (m, 2H), 4.11 (s, 3H), 4.06-3.95 (m, 4H), 3.93 (s, 3H), 2.48 (dd, J=15.3, 7.4 Hz, 2H). LCMS-ESI$^+$ (m/z): [M+H]$^+$ calculated for C$_{16}$H$_{19}$N$_2$O$_6$: 335.12. found: 335.06.

Step 6

A mixture of compound 37 (488 mg, 1.46 mmol) and 60% NaH (58.38 mg, 1.46 mmol) was placed in 0° C. bath and DMF (5 mL) was added to the mixture. After 5 min, allyl bromide (0.126 mL, 1.46 mmol) was added. After 45 min, 2 N NaOH (2.6 mL) was added and stirred at 0° C. for 2 h. The reaction mixture was then acidified with 2 N HCl (~4 mL) and the acidified reaction mixture was concentrated to remove solvents. The residue was dissolved in water and purified by HPLC to obtain compound 38. LCMS-ESI$^+$ (m/z): [M+H]$^+$ calculated for C$_{18}$H$_{21}$N$_2$O$_6$: 361.14. found: 361.11.

Step 7

A mixture of compound 38 (223 mg, 0.619 mmol), compound 11 (145.7 mg, 0.681 mmol), and HATU (470.55 mg, 1.238 mmol) in dichloromethane (8 mL) was stirred at room temperature as N,N-diisopropylethylamine (1.148 mL, 6.59 mmol) was added. After 30 min, the reaction mixture was diluted with ethyl acetate and washed with saturated NH$_4$Cl (×2), saturated NaHCO$_3$ (×2), and brine (×1). After the aqueous fractions were extracted with ethyl acetate (×1), the organic fractions were combined, dried (Na$_2$SO$_4$) and concentrated. The residue was purified by column chromatography on silica gel (24 g column) using hexanes-ethyl acetate-20% methanol in ethyl acetate as eluents to get compound 39: $^1$H NMR (400 MHz, Chloroform-d) δ 8.36 (s, 1H), 7.37-7.26 (m, 1H), 6.94 (td, J=8.5, 1.9 Hz, 1H), 6.11-5.85 (m, 1H), 5.48 (dt, J=17.1, 8.6 Hz, 1H), 5.41-5.22 (m, 2H), 5.20-4.99 (m, 2H), 4.65 (t, J=6.1 Hz, 2H), 4.56-4.32 (m, 3H), 4.06 (s, 3H), 4.04-3.76 (m, 3H), 2.81 (s, 1H), 2.57 (dd, J=14.5, 7.6 Hz, 1H), 2.41 (dd, J=14.4, 7.5 Hz, 1H). LCMS-ESI$^+$ (m/z): [M+H]$^+$ calculated for C$_{25}$H$_{25}$ClF$_2$N$_3$O$_5$: 520.15. found: 520.11.

Step 8

A solution of compound 39 (220 mg, 0.423 mmol) in dichloromethane (42 mL) was stirred in a 0° C. bath while Ar gas was bubbled through. After 20 min, Grubbs Catalyst 1$^{st}$ generation (31.82 mg, 42.31 μmol) was added and the Ar bubbling continued for 15 min. Then, the reaction mixture was refluxed at 50° C. After 2 h, the reaction mixture was concentrated and purified by column chromatography on silica gel (24 g column) using hexanes-ethyl acetate-20% methanol in ethyl acetate as eluents to get compound 40: $^1$H NMR (400 MHz, Chloroform-d) δ 10.40 (s, 1H), 8.37 (s, 1H), 7.35-7.27 (m, 1H), 6.93 (td, J=8.6, 1.8 Hz, 1H), 5.81 (dd, J=23.9, 8.4 Hz, 2H), 5.01 (d, J=19.2 Hz, 1H), 4.65 (d, J=6.1 Hz, 2H), 4.52 (s, 1H), 4.39 (dd, J=22.2, 9.6 Hz, 2H), 4.06 (s, 3H), 3.92-3.74 (m, 3H), 2.67 (d, J=16.8 Hz, 1H), 2.16 (d, J=17.3 Hz, 1H). LCMS-ESI⁺ (m/z): [M+H]⁺ calculated for $C_{23}H_{21}ClF_2N_3O_5$: 492.11. found: 492.15.

Step 9

To a solution of compound 40 (16 mg, 0.033 mmol) in acetonitrile (1.4 mL) was added magnesium bromide (15.57 mg, 0.085 mmol) at room temperature and the resulting mixture was stirred at 50° C. After 30 min, the reaction mixture was stirred at 0° C. and 1 N HCl was added to make the mixture a solution. The resulting solution was further diluted with water before extraction with dichloromethane (×3). The combined extracts were dried (MgSO₄) and concentrated. The residue was purified by column chromatography on silica gel (12 g column) using dichloromethane-20% methanol in dichloromethane as eluents to get compound 41: ¹H NMR (400 MHz, Chloroform-d) δ 12.72 (s, 1H), 10.43 (t, J=6.0 Hz, 1H), 8.36 (s, 1H), 7.33-7.19 (m, 1H), 6.91 (td, J=8.5, 1.8 Hz, 1H), 5.88 (ddt, J=9.8, 5.9, 1.9 Hz, 1H), 5.84-5.76 (m, 1H), 5.12 (dq, J=20.4, 3.1, 2.6 Hz, 1H), 4.64 (dd, J=10.9, 7.0 Hz, 3H), 4.40-4.34 (m, 2H), 3.86-3.74 (m, 3H), 2.75 (dd, J=16.9, 4.0 Hz, 1H), 2.22 (ddd, J=17.5, 6.2, 2.1 Hz, 1H). LCMS-ESI⁺ (m/z): [M+H]⁺ calculated for $C_{22}H_{19}ClF_2N_3O_5$: 478.10. found: 478.12.

Example 8

Preparation of Compound 42

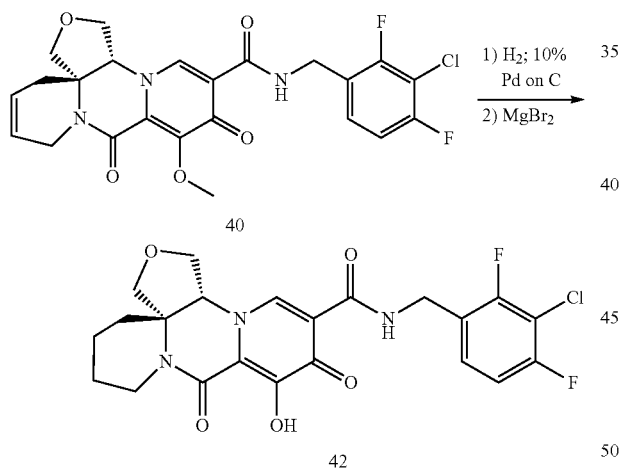

Step 1

To a solution of compound 40 (171 mg, 0.348 mmol) in ethanol (8 mL) was added 10% palladium on carbon (30.48 mg) and the resulting mixture was stirred under hydrogen atmosphere. After 2.5 h, the reaction mixture was filtered through celite pad and washed with ethanol. After the filtrate was concentrated, the residue was dissolved in acetonitrile (15 mL) and magnesium bromide (166.42 mg, 0.904 mmol) was added at room temperature before the resulting mixture was stirred at 50° C. bath for 30 min. After the reaction mixture was stirred at 0° C., 1 N HCl was added to make the mixture a solution. The resulting solution was further diluted with water before the product was extracted with dichloromethane (×3). The combined extracts were dried (MgSO₄) and concentrated. The residue was purified by column chromatography on silica gel (24 g column) using dichloromethane-20% methanol in dichloromethane as eluents to get compound 42: ¹H NMR (400 MHz, Chloroform-d) δ 12.97 (s, 1H), 10.45 (s, 1H), 8.27 (s, 1H), 7.27 (s, 3H), 7.00-6.85 (m, 1H), 4.83 (d, J=14.1 Hz, 1H), 4.67 (d, J=5.6 Hz, 2H), 4.52-4.40 (m, 1H), 4.38 (s, 2H), 4.03 (d, J=10.3 Hz, 1H), 3.80 (s, 1H), 2.96 (d, J=13.3 Hz, 1H), 1.93 (d, J=35.7 Hz, 3H). LCMS-ESI⁺ (m/z): [M+H]⁺ calculated for $C_{22}H_{21}ClF_2N_3O_5$: 480.11. found: 480.15.

Example 9

Preparation of Compound 48

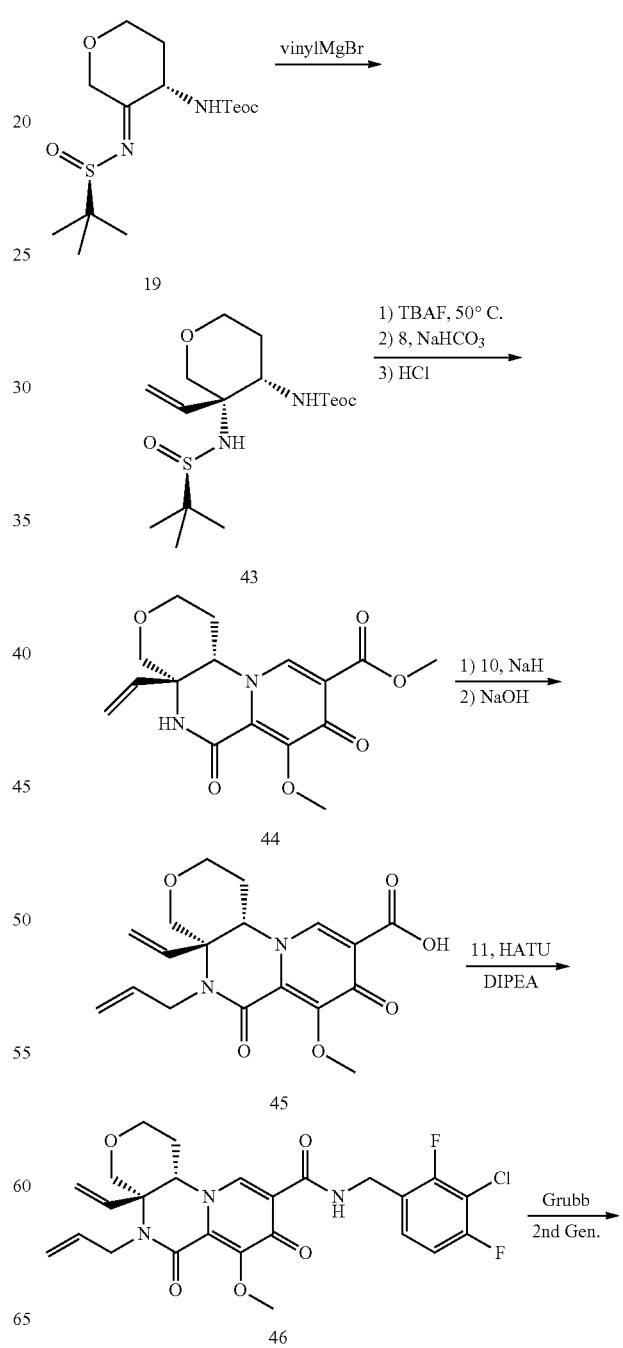

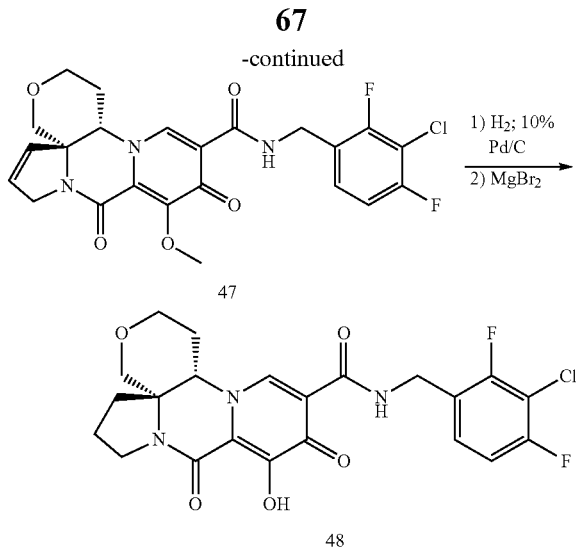

Step 1

To a solution of compound 19 (1192 mg, 3.288 mmol) in THF (15 mL) was stirred in −78° C. bath as vinylmagnesium bromide (1 M in THF, 13.5 mL) was added over ~2 min. The reaction mixture was slowly warmed up to −10° C. over 1.25 h and saturated NH₄Cl was added to the reaction mixture with some water. The mixture was extracted with ethyl acetate (×2) and the extracts were washed with water (×1). The combined extracts were dried (Na₂SO₄) and concentrated. The residue was purified by column chromatography on silica gel (120 g column) using hexanes-ethyl acetate as eluents to get compound 43: ¹H NMR (400 MHz, Chloroform-d) δ 6.00-5.88 (m, 1H), 5.61-5.49 (m, 2H), 4.59 (d, J=9.6 Hz, 1H), 4.39-4.28 (m, 1H), 4.23-4.06 (m, 3H), 4.04-3.93 (m, 1H), 3.82 (q, J=9.1 Hz, 1H), 3.56-3.43 (m, 2H), 1.66 (tt, J=12.9, 5.7 Hz, 2H), 1.20 (s, 9H), 1.04-0.88 (m, 2H), 0.04 (s, 9H). LCMS-ESI⁺ (m/z): [M+H]⁺ calculated for C₁₇H₃₅N₂O₄SSi: 391.21. found: 390.88.

Step 2

To a mixture of compound 43 (791 mg, 2.025 mmol) and tetrabutylammonium fluoride hydrate (2282 mg, 8.165 mmol) was added acetonitrile (10 mL) and stirred for 17 h at 50° C. The reaction mixture was acidified with 2 N HCl and neutralized with ~1 mL saturated NaHCO₃. The resulting solution was concentrated and dried in vacuum. A mixture of the residue, compound 8 (490.42 mg, 2.025 mmol), and NaHCO₃ (340.23 mg, 4.050 mmol) in water (2 mL) and MeOH (8 mL) was stirred at room temperature for 1 h. The reaction mixture was concentrate to remove most of the solvent. After the residue was dissolved in dichloromethane (12 mL) and treated 4 N HCl in dioxane (12 mL) at room temperature for 2 h. After the reaction mixture was concentrated, the residue was dissolved in methanol (20 mL) and DBU (1.591 mL, 10.64 mmol) was added to the solution. After the resulting mixture was stirred at 50° C. for 15 min, the reaction mixture was concentrated and solvent was co-evaporated with toluene. The residue was purified by column chromatography on silica gel (80 g column) using ethyl acetate-methanol in ethyl acetate as eluents to obtain compound 44: ¹H NMR (400 MHz, Chloroform-d) δ 8.10 (s, 1H), 6.61 (s, 1H), 6.11 (dd, J=17.2, 10.7 Hz, 1H), 5.37 (d, J=5.3 Hz, 1H), 5.34 (d, J=1.2 Hz, 1H), 4.41 (dt, J=12.1, 3.1 Hz, 1H), 4.29 (dd, J=12.2, 4.3 Hz, 1H), 4.08 (s, 3H), 3.91 (s, 4H), 3.74 (td, J=12.0, 2.4 Hz, 1H), 3.63-3.52 (m, 1H), 2.33 (d, J=12.4 Hz, 1H), 2.17 (qd, J=12.2, 5.1 Hz, 1H). LCMS-ESI⁺ (m/z): [M+H]⁺ calculated for C₁₆H₁₈N₂O₆: 335.12. found: 335.09.

Step 3

A mixture of compound 44 (360 mg, 1.077 mmol) and 60% NaH (172.27 mg, 4.307 mmol) was cooled at 0° C. as DMF (5 mL) was added to the mixture. After 5 min, compound 10 (0.051 mL, 0.589 mmol) was added. After 20 min, 2 N NaOH (0.6 mL) was added and stirred at 0° C. for 10 min. The reaction mixture was then acidified with 2 N HCl (~2.5 mL) and the acidified reaction mixture was concentrated to remove solvents. The residue was dissolved in water and purified by preparative HPLC (acetonitrile/H₂O with 0.1% TFA modifier). The product containing fractions were pooled and freeze-dried to obtain compound 45: ¹H NMR (400 MHz, Chloroform-d) δ 8.31 (s, 1H), 6.00 (dd, J=17.3, 10.7 Hz, 1H), 5.90 (dddd, J=15.1, 11.6, 6.1, 3.4 Hz, 1H), 5.36 (d, J=10.7 Hz, 1H), 5.32-5.18 (m, 2H), 5.10 (d, J=17.2 Hz, 1H), 4.51-4.34 (m, 3H), 4.18 (d, J=11.1 Hz, 1H), 4.06 (s, 3H), 3.76-3.62 (m, 3H), 2.52-2.36 (m, 1H), 2.16 (dd, J=12.2, 5.1 Hz, 1H). LCMS-ESI⁺ (m/z): [M+H]⁺ calculated for C₁₈H₂₀N₂O₆: 361.14. found: 361.14.

Step 4

A mixture of compound 45 (360.36 mg, 0.658 mmol), compound 11 (154.85 mg, 0.723 mmol), and HATU (500.09 mg, 1.315 mmol) in dichloromethane (15 mL) was stirred at room temperature as N,N-diisopropylethylamine (1.220 mL, 7.004 mmol) was added. After 30 min, the reaction mixture was diluted with ethyl acetate and washed with saturated NH₄Cl (×2), saturated NaHCO₃ (×2), and brine (×1). After the aqueous fractions were extracted with ethyl acetate (×1), the organic fractions were combined, dried (Na₂SO₄) and concentrated. The residue was purified by column chromatography on silica gel (24 g column) using hexanes-ethyl acetate-20% methanol in ethyl acetate as eluents to get compound 46: ¹H NMR (400 MHz, DMSO-d₆) δ 10.42 (t, J=6.0 Hz, 1H), 8.24 (s, 1H), 7.40 (td, J=8.5, 6.3 Hz, 1H), 7.29 (td, J=8.8, 1.6 Hz, 1H), 6.05 (dd, J=17.2, 10.7 Hz, 1H), 5.87 (dddd, J=16.8, 10.6, 6.2, 4.6 Hz, 1H), 5.40-5.18 (m, 2H), 5.21-5.09 (m, 1H), 5.04-4.89 (m, 1H), 4.67 (dd, J=11.8, 4.4 Hz, 1H), 4.56 (qd, J=15.1, 6.0 Hz, 2H), 4.33-4.13 (m, 3H), 3.82 (s, 3H), 3.70-3.51 (m, 2H), 3.35 (s, 2H), 2.69 (s, 1H), 2.40 (dd, J=12.1, 4.4 Hz, 1H), 2.09 (tt, J=12.2, 6.1 Hz, 1H). LCMS-ESI⁺ (m/z): [M+H]⁺ calculated for C₂₅H₂₄ClF₂N₃O₅: 520.14. found: 520.18.

Step 5

A solution of compound 46 (29 mg, 0.056 mmol) in dichloromethane (6 mL) was stirred in an ice bath while Ar gas was bubbled. After 30 min, Grubbs Catalyst 2ⁿᵈ generation (4.735 mg, 0.006 mmol) was added and the Ar bubbling continued for 15 min. Then, the reaction mixture was refluxed at 80° C. After 24 h, the reaction mixture was concentrated and purified by column chromatography on silica gel (12 g column) using hexanes-ethyl acetate-20% methanol in ethyl acetate as eluents to get compound 47: ¹H NMR (400 MHz, Chloroform-d) δ 10.59 (t, J=5.9 Hz, 1H), 8.49 (s, 1H), 7.26 (m, 1H), 6.93 (td, J=8.5, 1.9 Hz, 1H), 6.42-6.21 (m, 2H), 4.79-4.55 (m, 3H), 4.40 (ddd, J=21.5, 12.0, 4.6 Hz, 2H), 4.15-4.03 (m, 1H), 4.02 (s, 3H), 3.87 (dd, J=10.8, 1.1 Hz, 1H), 3.72 (td, J=11.8, 3.0 Hz, 1H), 3.45 (d, J=10.7 Hz, 1H), 2.62-2.35 (m, 2H). LCMS-ESI⁺ (m/z): [M+H]⁺ calculated for C₂₃H₂₀ClF₂N₃O₅: 492.11. found: 492.09.

Step 6

To a solution of compound 47 (3.8 mg) in ethanol (1 mL) was added 10% palladium on carbon (1.6 mg) at room temperature and the resulting mixture was stirred under hydrogen atmosphere. After 40 min, the mixture was filtered through celite and the celite pad was washed with ethanol. The combined filtrate and washing were concentrated and the residue was used for the next reaction.

The above residue in acetonitrile (1 mL) was added magnesium bromide (4.7 mg, 0.026 mmol) at room temperature and the resulting mixture was stirred at 50° C. After 30 min, the reaction mixture was stirred at 0° C. and 1 N HCl was add to make the mixture a solution, and diluted with water before extraction with $CH_2Cl_2$ (×3). The combined extracts were dried ($MgSO_4$) and concentrated. The residue was purified by column chromatography on silica gel (12 g column) using dichloromethane-20% methanol in dichloromethane as eluents. The sample was dissolved in dioxane and freeze-dried to get compound 48: $^1$H NMR (400 MHz, Chloroform-d) δ 12.85 (s, 1H), 10.48 (t, J=6.1 Hz, 1H), 8.39 (s, 1H), 7.40-7.14 (m, 1H), 6.91 (td, J=8.5, 1.8 Hz, 1H), 4.64 (dd, J=17.4, 5.7 Hz, 3H), 4.08-3.98 (m, 1H), 3.87 (ddd, J=16.9, 11.7, 6.9 Hz, 2H), 3.65 (t, J=11.2 Hz, 1H), 3.61-3.52 (m, 1H), 3.03 (td, J=13.4, 3.1 Hz, 1H), 2.70 (d, J=15.7 Hz, 1H), 1.92 (ddd, J=19.2, 9.3, 4.7 Hz, 1H), 1.83-1.67 (m, 4H), 1.58 (m, 2H). $^{19}$F NMR (376 MHz, Chloroform-d) δ −115.18 (q, J=6.5, 5.4 Hz, 1F), −117.36 (dd, J=8.0, 3.3 Hz, 1F). LCMS-ESI$^+$ (m/z): [M+H]$^+$ calculated for $C_{23}H_{21}ClF_2N_3O_5$: 492.11. found: 492.15.

Example 10

Preparation of Compound 56 and 57

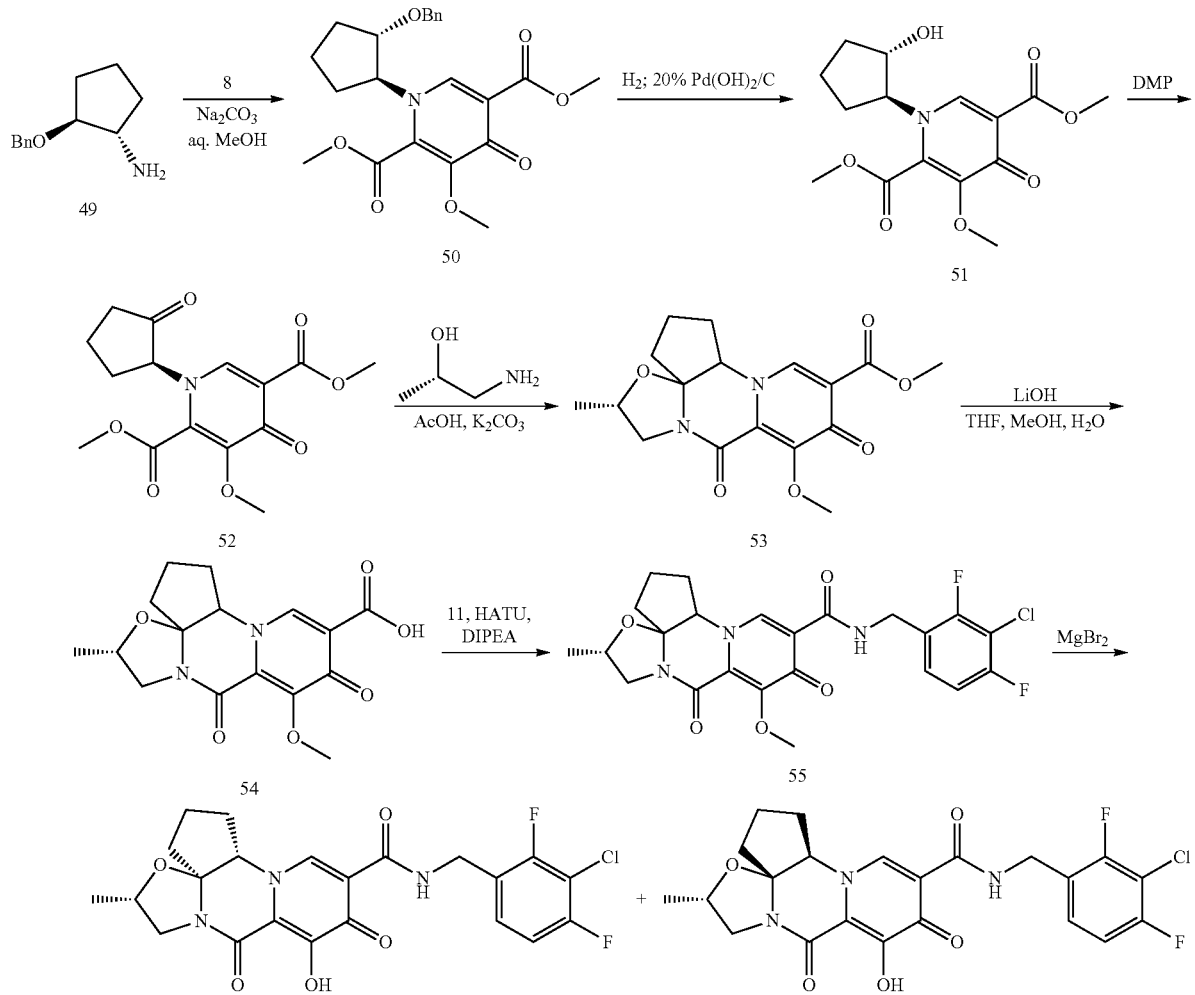

Step 1

A mixture of compound 8 (6.4 g, 26.4 mmol), compound 49 (4.9 g, 25.7 mmol), and sodium bicarbonate (8.64 g, 103 mmol) in a 7:2 mixture of MeOH:water (90 mL) was stirred at room temperature for 24 h. After the solution was concentrated, the residue was taken up in methanol (80 mL) and stirred at 50° C. for an additional 2 h. After the solution was concentrated, the residue was partitioned between water and ethyl acetate. The separated aqueous phase was extracted to ethyl acetate (×3), and all organic fractions were combined, dried ($MgSO_4$), and concentrated to yield crude compound 50 which was carried on to the next step as crude: LCMS-ESI$^+$ (m/z): [M+H]$^+$ calculated for $C_{22}H_{26}NO_7$: 416.17. found: 416.2.

Step 2

Crude compound 50 and 20% palladium hydroxide on carbon (4.37 g, 3.11 mmol) were suspended in ethanol (100 mL) and stirred at 40° C. under hydrogen atmosphere for 2 h. After the suspension was filtered through celite pad with ethanol rinses, the filtrate was concentrated to afford compound 51 which was carried on to the next step as crude: $^1$H NMR (400 MHz, DMSO-$d_6$) δ 8.30 (s, 1H), 5.31 (d, J=5.4 Hz, 1H), 4.35-4.19 (m, 1H), 3.93 (s, 3H), 3.81 (q, J=8.1 Hz, 1H), 3.75 (s, 3H), 3.74 (s, 3H), 2.16-2.03 (m, 1H), 1.99-1.85 (m, 1H), 1.84-1.63 (m, 3H), 1.56-1.44 (m, 1H).

Step 3

The solution of crude compound 51 in dichloromethane (100 mL) was treated with Dess-Martin periodinane (5.75 g, 13.6 mmol) at room temperature for 1 h. After the reaction mixture was quenched with a saturated NaHCO$_3$ (50 mL) and some solid Na$_2$SO$_3$, the separated aqueous fraction was extracted to dichloromethane (×1) and the combined organic fractions were dried (MgSO$_4$), and concentrated. The resulting residue was purified by column chromatography on silica gel using dichloromethane-10% methanol in dichloromethane as eluents to afford compound 52: LCMS-ESI$^+$ (m/z): [M+H]$^+$ calculated for $C_{15}H_{18}NO_7$: 324.11. found: 324.1.

Step 4

To a solution of compound 52 (740 mg, 2.3 mmol) in acetonitrile (13.5 mL) were added acetic acid (1.5 mL, 26.2 mmol), potassium carbonate (1.27 g, 9.2 mmol), and (S)-1-aminopropan-2-ol (0.75 mL, 9.6 mmol) and the mixture was stirred at 70° C. for 4 h. After the reaction mixture was concentrated with silica gel, the resulting adsorbed mixture was purified by flash column chromatography on silica gel using dichloromethane-6% methanol in dichloromethane as eluents to afford compound 53 as a mixture of diastereomers.

Step 5

A solution of compound 53 (242 mg, 0.69 mmol) in a 2:1 mixture of THF:MeOH (5 mL) was treated with an 2.0 M lithium hydroxide (0.7 mL, 1.4 mmol). After 3 h, the reaction mixture was acidified with 0.5 M HCl and the product was extracted with ethyl acetate (×3). The combined extracts were dried (MgSO$_4$), and concentrated. The residue was purified by column chromatography on silica gel using dichloromethane-4% methanol in dichloromethane as eluents to afford compound 54 as a mixture of diastereomers.

Steps 6-7

To a solution of compound 54 (40 mg, 0.12 mmol), HATU (58 mg, 0.15 mmol), and compound 11 (40 mg, 0.18 mmol) in dichloromethane (2 mL) was added N,N-diisopropylethylamine (0.11 mL, 0.62 mmol). After 1.5 h, the reaction mixture was diluted with ethyl acetate, washed with 5% aqueous NaHCO$_3$ (×2), dried (MgSO$_4$), and concentrated under reduced pressure to afford compound 55 which was carried forward as crude.

To a solution of compound 55 in acetonitrile (2 mL) was added magnesium bromide (48 mg, 0.26 mmol) and the resulting mixture was stirred at 50° C. for 2 h. After the mixture was cooled and dissolved by addition of 0.5 M HCl, the product was extracted by dichloromethane (×3) and the combined extracts were dried (MgSO$_4$), and concentrated. The residue was purified by preparative HPLC (acetonitrile/H$_2$O with 0.1% TFA modifier) to afford compound 56 and compound 57 as distinct diastereomers.

Compound 56 (earlier eluting diasteromer): $^1$H NMR (400 MHz, Chloroform-d) δ 10.49 (s, 1H), 8.57 (s, 1H), 7.33-7.23 (m, 1H), 6.92 (td, J=8.5, 1.6 Hz, 1H), 4.66 (d, J=5.6 Hz, 2H), 4.51 (dt, J=12.7, 6.4 Hz, 1H), 4.15 (d, J=4.8 Hz, 1H), 3.87 (dd, J=11.5, 6.8 Hz, 1H), 3.51 (dd, J=11.4, 8.1 Hz, 1H), 2.67-2.46 (m, 2H), 2.18 (ddd, J=13.1, 8.8, 3.7 Hz, 1H), 2.06-1.63 (m, 3H), 1.44 (d, J=6.1 Hz, 3H). LCMS-ESI$^+$ (m/z): [M+H]$^+$ calculated for $C_{22}H_{21}ClF_2N_3O_5$: 480.10. found: 480.2.

Compound 57 (late eluting diasteromer): $^1$H NMR (400 MHz, Chloroform-d) δ 10.52 (s, 1H), 8.60 (s, 1H), 7.33-7.22 (m, 1H), 6.93 (t, J=8.3 Hz, 1H), 4.66 (s, 2H), 4.47 (dd, J=11.5, 5.5 Hz, 1H), 4.25 (dt, J=9.7, 5.8 Hz, 1H), 4.07 (d, J=4.3 Hz, 1H), 3.18 (t, J=10.4 Hz, 1H), 2.72-2.41 (m, 2H), 2.16 (t, J=10.1 Hz, 1H), 2.08-1.91 (m, 1H), 1.91-1.72 (m, 1H), 1.45 (d, J=6.0 Hz, 3H). LCMS-ESI$^+$ (m/z): [M+H]$^+$ calculated for $C_{22}H_{21}ClF_2N_3O_5$: 480.10. found: 480.2.

Example 11

Preparation of Compound 60 and 61

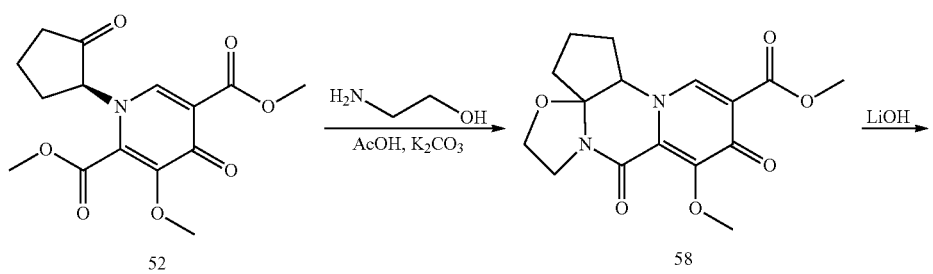

52

58

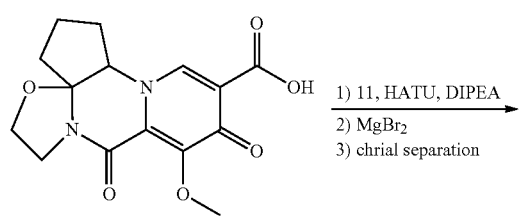

59

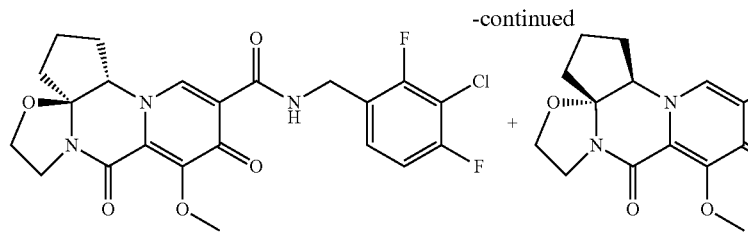

60 and 61

Step 1

A mixture of compound 52 (1.33 g, 4.12 mmol), acetic acid (3 mL, 52.40 mmol), potassium carbonate (2.31 g, 16.5 mmol), and 2-aminoethanol (0.99 mL, 16.5 mmol) in acetonitrile (27 mL) was stirred in 60° C. bath for 2.5 h. The reaction mixture was cooled, treated with methanol, and concentrated with silica gel. The resulting adsorbed mixture was purified by column chromatography on silica gel using ethyl acetate-ethanol as eluents to afford compound 58 as a racemic mixture: LCMS-ESI+ (m/z): [M+H]+ calculated for $C_{15}H_{18}NO_7$: 335.12. found: 335.1.

Step 2

Compound 58 (0.415 g, 1.24 mmol) in THF (4 mL) and methanol (2 mL) was treated with 2 M lithium hydroxide (1.24 mL) and stirred at room temperature for 20 min. After the reaction mixture was acidified with 0.5 M HCl (5-10 mL) and diluted with water, the product was extracted with ethyl acetate (×2), and the combined organic extracts were dried ($Na_2SO_4$) and concentrated to afford compound 59: $^1$H NMR (400 MHz, DMSO-$d_6$) 8.62 (s, 1H), 4.52 (d, J=5.0 Hz, 1H), 4.20-4.02 (m, 2H), 3.90 (m, 4H), 3.57 (ddd, J=11.1, 6.7, 5.0 Hz, 1H), 2.60-2.51 (m, 1H), 2.41-2.27 (m, 1H), 2.09-1.95 (m, 1H), 1.82-1.56 (m, 3H).

Step 3

A solution of compound 59 (0.085 g, 0.27 mmol), compound 11 (0.098 g, 0.552 mmol), and HATU (0.111 g, 0.29 mmol) in acetonitrile (3 mL) was treated with N,N-diisopropylethylamine (0.094 mL, 0.53 mmol). The reaction mixture was stirred for 2 h and additional compound 11 (0.050 g, 0.28 mmol) and HATU (0.050 g, 0.13 mmol) were added. After 10 min, the reaction mixture was diluted with ethyl acetate, washed with 0.5 M HCl (×1) and 5% aqueous $NaHCO_3$ (×1), dried ($Na_2SO_4$), and concentrated to afford crude amide, which was taken on to the next step: LCMS-ESI+ (m/z): [M+H]+ calculated for $C_{20}H_{20}F_3N_2O_7$: 457.12. found: 457.1.

The crude amide (0.127 g, 0.265 mmol) was suspended in acetonitrile and treated with magnesium bromide (0.146 g, 0.795 mmol). The mixture was placed in a 50° C. bath and stirred for 10 min. After cooling, the reaction mixture was acidified with 0.5 M HCl and the product was extracted with ethyl acetate. The organic extract was dried ($Na_2SO_4$), concentrated, and purified by column chromatography on silica gel using dichloromethane-ethanol as eluents to afford the racemic product. This material was separated into its enantiomers by HPLC using a ChiralPak AD-H column (eluents: methanol-acetonitrile) to giving desired two enantiomers 60 and 61.

Compound 60 (earlier eluting enantiomer): $^1$H NMR (400 MHz, DMSO-$d_6$) δ 12.34 (s, 1H), 10.41 (t, J=5.8 Hz, 1H), 8.43 (s, 1H), 7.40 (td, J=8.7, 6.6 Hz, 1H), 7.35-7.21 (m, 1H), 4.65-4.52 (m, 2H), 4.42 (d, J=4.9 Hz, 1H), 4.22-4.07 (m, 2H), 3.98-3.87 (m, 1H), 3.75-3.62 (m, 1H), 2.47-2.41 (m, 1H), 2.42-2.29 (m, 1H), 2.13-1.99 (m, 1H), 1.81-1.66 (m, 3H). LCMS-ESI+ (m/z): [M+H]+ calculated for $C_{11}H_{19}ClF_2N_3O_5$: 466.10. found: 466.2.

Compound for 61 (late eluting enantiomer): $^1$H NMR (400 MHz, DMSO-$d_6$) δ 12.34 (s, 1H), 10.41 (t, J=6.2 Hz, 1H), 8.43 (s, 1H), 7.40 (td, J=8.5, 6.8 Hz, 1H), 7.35-7.25 (m, 1H), 4.64-4.54 (m, 2H), 4.43 (d, J=5.2 Hz, 1H), 4.24-4.07 (m, 2H), 4.00-3.88 (m, 1H), 3.73-3.62 (m, 1H), 2.45 (m, 1H), 2.42-2.29 (m, 1H), 2.06 (m, 1H), 1.80-1.64 (m, 3H). LCMS-ESI+ (m/z): [M+H]+ calculated for $C_{11}H_{19}ClF_2N_3O_5$: 466.10. found: 466.2.

Example 12

Preparation of Compound 65

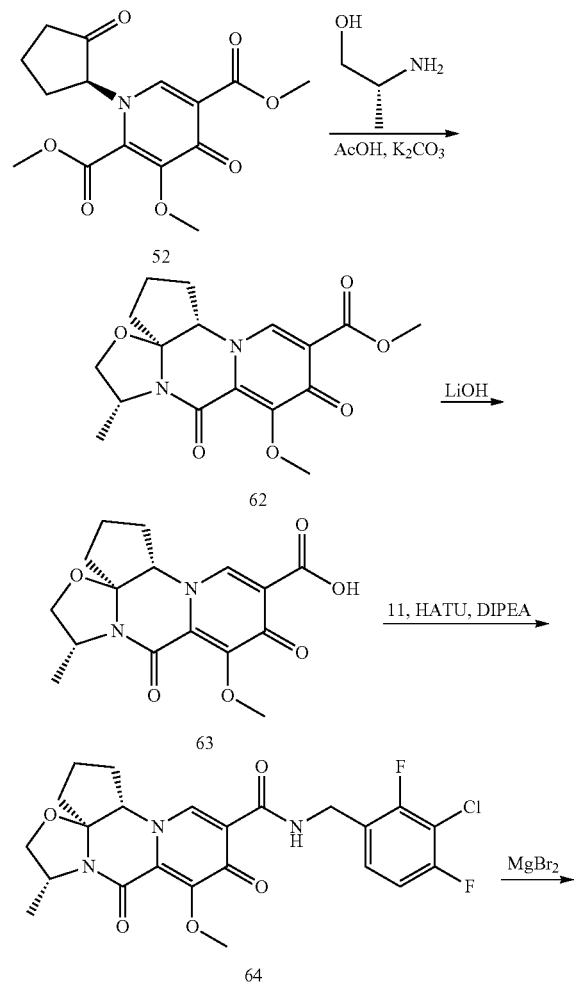

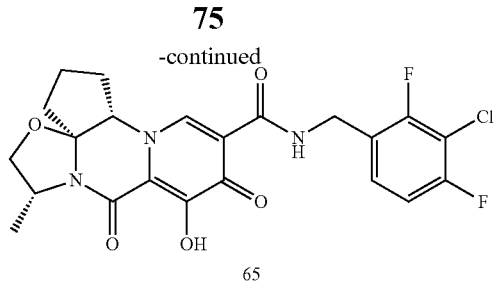

65

Step 1

A mixture of compound 52 (430 mg, 1.3 mmol), acetic acid (1 mL, 17.47 mmol), potassium carbonate (0.78 g, 5.6 mmo), and (R)-2-aminopropan-1-ol (0.43 mL, 5.5 mmol) in acetonitrile (9 mL) was stirred at 70° C. for 5 h. The reaction mixture was diluted with methanol and then concentrated with silica gel. The resulting adsorbed mixture was purified by column chromatography on silica gel using ethyl acetate-15% ethanol in dichloromethane as eluents to afford compound 62 as a single diastereomer.

Step 2

A mixture of compound 62 (161 mg, 0.43 mmol) in a 2:1 mixture of THF:MeOH (3 mL) was treated with 2.0 M lithium hydroxide (0.5 mL) and stirred at room temperature for 1 h. After the reaction mixture was acidified with 0.5 M HCl and diluted with water, the product was extracted with ethyl acetate (×3), and the combined organic extracts were dried ($Na_2SO_4$) and concentrated. The residue was purified by column chromatography on silica gel using dichloromethane-10% ethanol in dichloromethane as eluents to afford compound 63.

Step 3

To a solution of compound 63 (32 mg, 0.1 mmol), HATU (54 mg, 0.14 mmol), and compound 11 (32 mg, 0.15 mmol) in dichloromethane (2 mL) was added N,N-diisopropylethylamine (0.1 mL, 0.56 mmol). The reaction mixture was stirred for 1.5 h, diluted with ethyl acetate, washed with a 5% aqueous $NaHCO_3$ (×2), dried ($MgSO_4$), and concentrated to afford compound 64 which was carried forward as crude.

Step 4

To a solution of the above compound 64 in acetonitrile (2 mL) was added magnesium bromide (41 mg, 0.22 mmol) and the resulting mixture was stirred at 50° C. for 30 minutes. After the mixture was cooled, it was acidified with 0.5 M HCl, extracted to dichloromethane (×3), dried ($MgSO_4$), and concentrated. The resulting residue was purified by column chromatography on silica gel using dichloromethane-10% ethanol in dichloromethane as eluents to afford compound 65. $^1$H NMR (400 MHz, Chloroform-d) δ 10.50-10.37 (m, 1H), 8.53 (s, 1H), 7.33-7.23 (m, 1H), 6.91 (t, J=9.3 Hz, 1H), 4.64 (d, J=6.0 Hz, 2H), 4.47 (q, J=6.6 Hz, 1H), 4.33 (dd, J=8.9, 7.3 Hz, 1H), 4.06 (d, J=4.8 Hz, 1H), 3.75 (dd, J=8.9, 6.6 Hz, 1H), 2.66-2.57 (m, 1H), 2.52-2.39 (m, 1H), 2.22-2.08 (m, 1H), 2.03-1.69 (m, 3H), 1.46 (d, J=6.4 Hz, 3H). LCMS-ESI$^+$ (m/z): [M+H]$^+$ calculated for $C_{22}H_{21}ClF_2N_3O_5$: 480.10. found: 480.2.

Example 13

Preparation of Compound 66

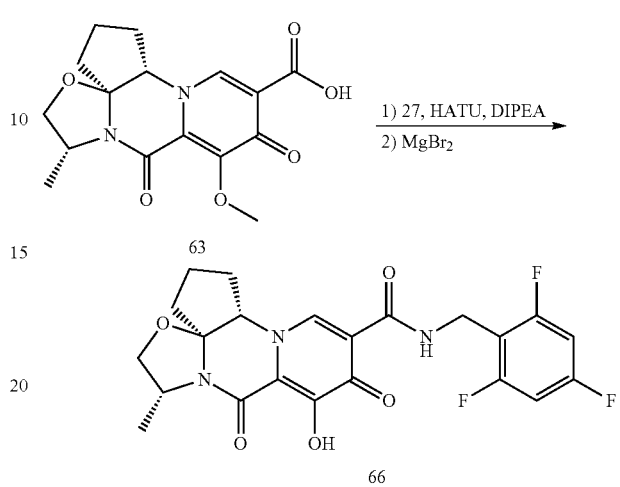

Step 1

To a solution of compound 63 (32 mg, 0.1 mmol), HATU (46 mg, 0.12 mmol), and compound 27 (0.02 mL, 0.17 mmol) in dichloromethane (2 mL) was added N,N-diisopropylethylamine (0.07 mL, 0.39 mmol). The reaction mixture was stirred for 1.5 h, diluted with ethyl acetate, washed with a 5% aqueous $NaHCO_3$ (×2), dried ($MgSO_4$), and concentrated under reduced pressure to afford the crude amide which was carried forward as crude.

To a solution of the above crude amide in acertonitrile (2 mL) was added magnesium bromide (39 mg, 0.21 mmol) and the resulting mixture was stirred at 50° C. for 30 minutes. After the mixture was cooled and acidified with 0.5 M HCl, the product was extracted with dichloromethane (×3), and the combined extracts were dried ($MgSO_4$) and concentrated. The residue was purified by column chromatography on silica gel using dichloromethane-10% ethanol in dichloromethane as eluents to afford compound 66. $^1$H NMR (400 MHz, Chloroform-d) δ 10.35 (t, J=5.5 Hz, 1H), 8.53 (s, 1H), 6.69-6.58 (m, 2H), 4.69-4.58 (m, 2H), 4.46 (q, J=6.6 Hz, 1H), 4.35-4.29 (m, 1H), 4.06-4.01 (m, 1H), 3.77-3.72 (m, 1H), 2.66-2.56 (m, 1H), 2.50-2.37 (m, 1H), 2.19-2.09 (m, 1H), 2.00-1.68 (m, 3H), 1.45 (d, J=6.4 Hz, 3H). LCMS-ESI$^+$ (m/z): [M+H]$^+$ calculated for $C_{22}H_{21}F_3N_3O_5$: 464.14. found: 464.3.

Example 14

Preparation of Compound 69

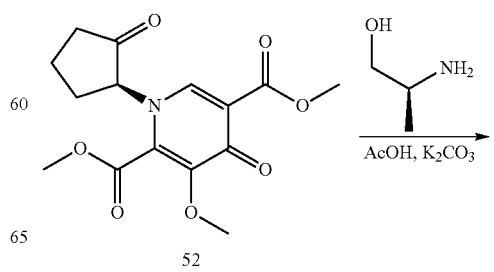

52

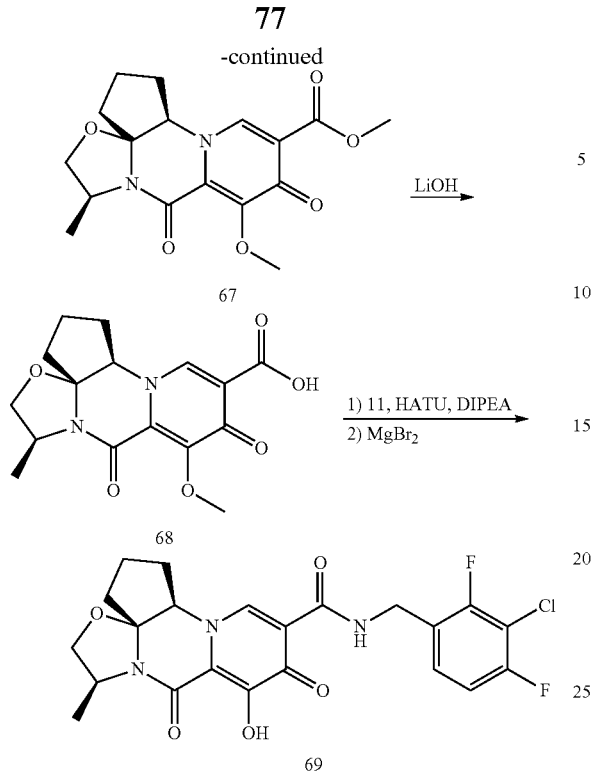

Step 1

A mixture of compound 52 (481 mg, 1.5 mmol), acetic acid (1 mL, 17.5 mmol), potassium carbonate (0.82 g, 5.9 mmo), and (S)-2-aminopropan-1-ol (0.5 mL, 6.4 mmol) in acetonitrile (9 mL) was stirred at 70° C. for 6 h and then diluted with methanol before concentration with silica gel. The resulting adsorbed mixture was purified by column chromatography on silica gel using dichloromethane-15% ethanol in dichloromethane as eluents to afford compound 67 as a single diastereomer.

Step 2

To a mixture of compound 67 (142 mg, 0.41 mmol) in a 2:1 mixture of THF:MeOH (3 mL) was added 2.0 M lithium hydroxide (0.5 mL, 1.0 mmol) and the reaction mixture was stirred at room temperature for 1 h. After the mixture was acidified with 0.5 M HCl, the product was extracted with ethyl acetate (×3) and the combined organic extracts were dried (MgSO$_4$), and concentrated. The residue was purified by column chromatography on silica gel using dichloromethane-10% methanol in dichloromethane as eluents to afford compound 68.

Steps 3

To a solution of compound 68 (25 mg, 0.07 mmol), HATU (40 mg, 0.11 mmol), and compound 11 (20 mg, 0.09 mmol) in dichloromethane (2 mL) was added N,N-diisopropylethylamine (0.06 mL, 0.34 mmol). The reaction mixture was stirred for 1.5 h, diluted with ethyl acetate, washed with a 5% aqueous NaHCO$_3$ (×2), dried (MgSO$_4$) and concentrated to afford the crude amide which was carried forward as crude.

To a solution of the crude amide in acetonitrile (2 mL) was added magnesium bromide (32 mg, 0.17 mmol) and the reaction mixture was stirred at 50° C. for 30 minutes. After the mixture was acidified with 0.5 M HCl, the product was extracted to dichloromethane (×3), and the combined extracts were dried (MgSO$_4$), and concentrated. The residue was purified by column chromatography on silica gel using dichloromethane-10% methanol in dichloromethane as eluents to afford compound 69. $^1$H NMR (400 MHz, Chloroform-d) δ 10.43 (t, J=5.9 Hz, 1H), 8.52 (s, 1H), 7.27 (q, J=7.0, 5.9 Hz, 1H), 6.91 (tt, J=8.5, 2.3 Hz, 1H), 4.64 (d, J=6.0 Hz, 1H), 4.51-4.29 (m, 2H), 4.06 (d, J=4.8 Hz, 1H), 3.75 (dd, J=8.9, 6.6 Hz, 1H), 3.46 (s, 1H), 2.71-2.39 (m, 2H), 2.23-2.08 (m, 1H), 2.06-1.68 (m, 3H), 1.47 (d, J=6.4 Hz, 3H). LCMS-ESI$^+$ (m/z): [M+H]$^+$ calculated for C$_{22}$H$_{21}$ClF$_2$N$_3$O$_5$: 480.10. found: 480.3.

Example 15

Preparation of Compound 70

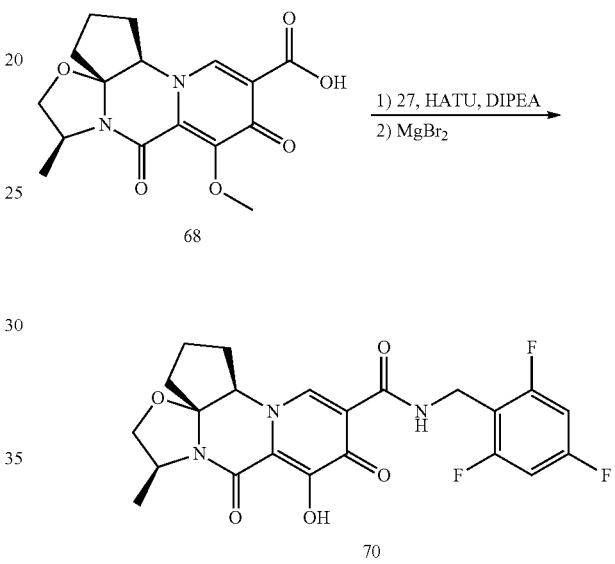

Step 1

To a solution of compound 68 (25 mg, 0.07 mmol), HATU (38 mg, 0.1 mmol), and compound 27 (0.03 mL, 0.25 mmol) in dichloromethane (2 mL) was added N,N-diisopropylethylamine (0.06 mL, 0.34 mmol). The reaction mixture was stirred for 1.5 h, diluted with ethyl acetate, washed with a 5% aqueous NaHCO$_3$ (×2), dried (MgSO$_4$), and concentrated to afford the crude amide which was carried forward as crude.

To a solution of the crude amide in acetonitrile (2 mL) was added magnesium bromide (36 mg, 0.2 mmol) and the reaction mixture was stirred at 50° C. for 30 minutes. After the mixture was acidified with 0.5 M HCl, the product was extracted to dichloromethane (×3), and the combined extracts were dried (MgSO$_4$) and concentrated. The residue was purified by column chromatography on silica gel using dichloromethane-10% methanol in dichloromethane as eluents to afford compound 70. $^1$H NMR (400 MHz, Chloroform-d) δ 10.34 (t, J=5.5 Hz, 1H), 8.53 (s, 1H), 6.68-6.59 (m, 2H), 4.72-4.59 (m, 2H), 4.47 (q, J=6.7 Hz, 1H), 4.33 (dd, J=8.9, 7.2 Hz, 1H), 4.04 (d, J=4.9 Hz, 1H), 3.75 (dd, J=9.0, 6.6 Hz, 1H), 2.67-2.57 (m, 1H), 2.52-2.39 (m, 1H), 2.21-2.10 (m, 1H), 1.95-1.67 (m, 3H), 1.47 (d, J=6.4 Hz, 3H). LCMS-ESI$^+$ (m/z): [M+H]$^+$ calculated for C$_{22}$H$_{21}$F$_3$N$_3$O$_5$: 464.14. found: 464.2.

Example 16

Preparation of Compounds 73 and 74

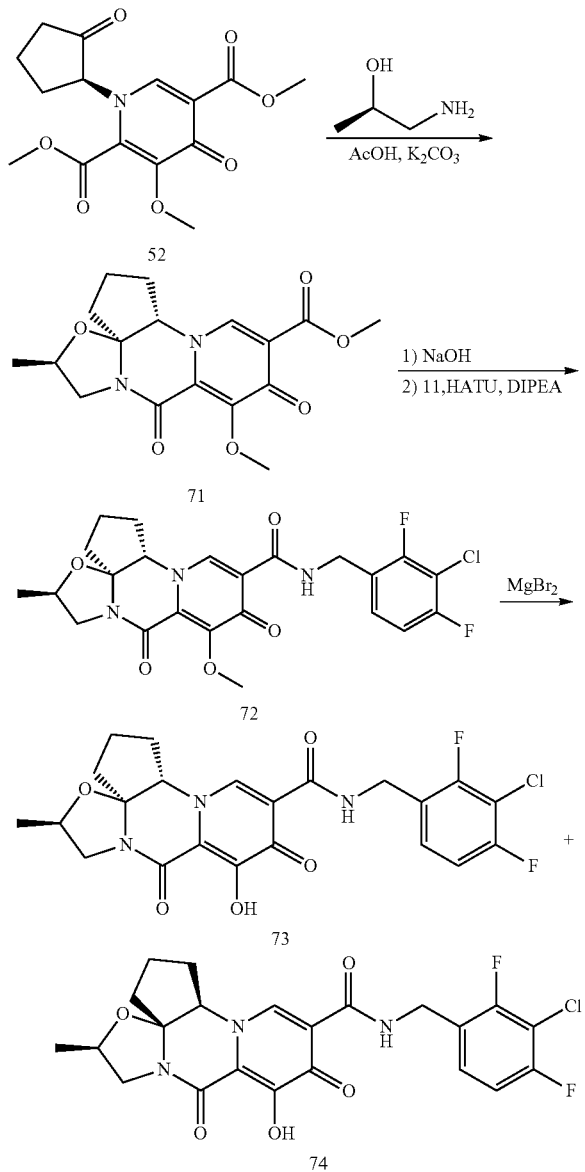

Step 1

To compound 52 (950 mg, 2.94 mmol) in acetonitrile (20 mL) were added acetic acid (1.5 mL, 26.20 mmol), potassium carbonate (1.624 g, 11.75 mmol), and (R)-1-aminopropan-2-ol (0.92 ml, 11.75 mmol). After stirring at 70° C. for 16 h, the mixture was dissolved by MeOH and concentrated with silica gel. The resulting adsorbed mixture was purified by column chromatography on silica gel using dichloromethane-20% methanol in dichloromethane as eluents to obtain 71 as a mixture of two diastereomers. LCMS-ESI$^+$ (m/z): [M+H]$^+$ calculated for $C_{17}H_{2i}N_2O_6$: 349.14. found: 349.12.

Step 2

A solution of 71 (423 mg, 1.214 mmol) in THF (20 mL), MeOH (2 mL), and 1 N NaOH (5 mL) was stirred at room temperature for 1 h. After the mixture was acidified with 3 N HCl, it was concentrated to dryness and the residue was purified by column chromatography on silica gel using dichloromethane-10% ethanol in dichloromethane as eluents to afford the acid. LCMS-ESI$^+$ (m/z): [M+H]$^+$ calculated for $C_{16}H_{19}N_2O_6$: 335.12. found: 335.11.

To a mixture of the crude acid (94 mg, 0.281 mmol), compound 11 (120 mg, 0.562 mmol), and HATU (160 mg, 0.422 mmol) in DMF (3 mL) was added N,N-diisopropylethylamine (0.3 mL, 1.7 mmol) at room temperature. After 0.5 h, the reaction mixture was diluted with dichloromethane, washed with 3% LiCl, saturated NH$_4$Cl and 0.5 N HCl. The organic fraction was dried (Na$_2$SO$_4$) and concentrated. The residue was purified by silica gel column chromatography using dichloromethane-20% methanol in dichloromethane as eluents to get a mixture of two isomers 72. LCMS-ESI$^+$ (m/z): [M+H]$^+$ calculated for $C_{23}H_{23}ClF_2N_3O_5$: 494.13. found: 494.15.

Step 3

To a solution of compound 72 (138 mg, 0.281 mmol) in acetonitrile (5 mL) was added magnesium bromide (155 mg, 0.843 mmol) and the mixture was stirred at 50° C. for 30 min. After the mixture was cooled and acidified with 10% HCl, the product was extracted with ethyl acetate (×2). The combined organic extracts were dried (MgSO$_4$), concentrated, and purified by preparative HPLC (acetonitrile/H$_2$O with 0.1% TFA modifier) to afford compounds 73 and 74.

Compound 73 (earlier eluting diastereomer): 35 mg (26%), $^1$H NMR (400 MHz, Chloroform-d) δ 10.52 (t, J=6.1 Hz, 1H), 8.58 (s, 1H), 7.32-7.23 (m, 1H), 6.93 (td, J=8.5, 1.8 Hz, 1H), 4.67 (d, J=6.0 Hz, 2H), 4.52 (dt, J=8.0, 6.3 Hz, 1H), 4.15 (d, J=4.9 Hz, 1H), 3.87 (dd, J=11.5, 6.8 Hz, 1H), 3.52 (dd, J=11.4, 8.1 Hz, 1H), 2.68-2.40 (m, 2H), 2.19 (ddd, J=14.8, 8.6, 3.9 Hz, 1H), 2.07-1.77 (m, 2H), 1.69 (ddd, J=13.9, 10.5, 7.5 Hz, 1H), 1.44 (d, J=6.1 Hz, 3H). $^{19}$F NMR (377 MHz, Chloroform-d) δ −76.42, −114.87 (p, J=4.1 Hz), −117.24 (dd, J=8.3, 3.3 Hz). LCMS-ESI$^+$ (m/z): [M+H]$^+$ calculated for $C_{22}H_{21}ClF_2N_3O_5$: 480.11. found: 480.16.

Compound 74 (late eluting diastereomer): 9 mg (7%), $^1$H NMR (400 MHz, Chloroform-d) δ 10.48 (t, J=5.9 Hz, 1H), 8.56 (s, 1H), 7.43-7.15 (m, 1H), 6.92 (td, J=8.7, 1.6 Hz, 1H), 4.66 (d, J=4.5 Hz, 2H), 4.48 (dd, J=11.5, 5.5 Hz, 1H), 4.24 (dt, J=9.4, 5.8 Hz, 1H), 4.02 (d, J=4.5 Hz, 1H), 3.17 (dd, J=11.5, 9.5 Hz, 1H), 2.67-2.40 (m, 2H), 2.25-2.09 (m, 1H), 2.00 (s, 2H), 1.92-1.73 (m, 2H), 1.45 (d, J=6.0 Hz, 3H). $^{19}$F NMR (377 MHz, Chloroform-d) δ −76.46, −115.00 (dq, J=8.4, 3.8 Hz), −117.32 (d, J=7.6 Hz). LCMS-ESI$^+$ (m/z): [M+H]$^+$ calculated for $C_{22}H_{21}ClF_2N_3O_5$: 480.11. found: 480.11.

Example 17

Preparation of Compound 77

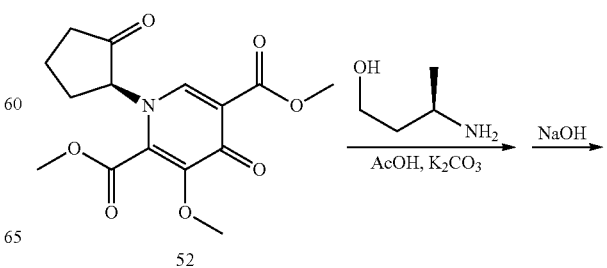

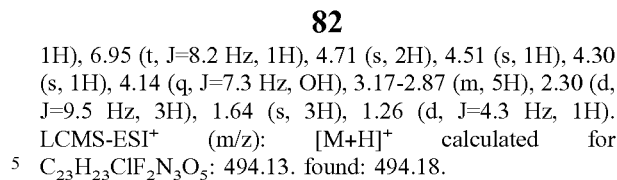

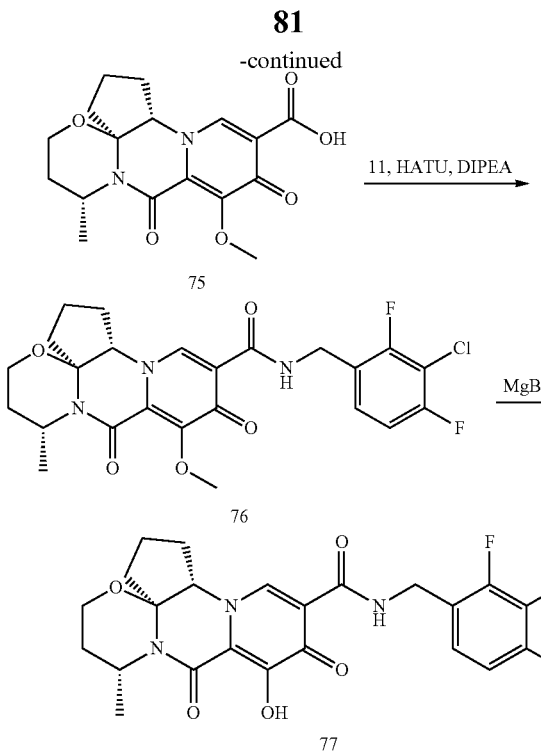

Step 1

To a solution of compound 52 (460 mg, 1.42 mmol) in acetonitrile (20 mL) were added acetic acid (1.0 mL, 17.47 mmol), potassium carbonate (0.8 g, 5.7 mmol), and (R)-3-aminobutan-1-ol (0.39 mL, 4.27 mmol). After the mixture was stirred to 70° C. for 24 h, it was concentrated and the residue was used for the next reaction.

The solution of the above residue in THF (2 mL), methanol (2 mL), and 1 N NaOH (5 mL) was stirred at room temperature for 1 h. The resulting mixture was acidified with 3 N HCl and concentrated to dryness. The residue was purified by column chromatography on silica gel using dichloromethane-20% methanol in dichloromethane as eluents to get compound 75. LCMS-ESI$^+$ (m/z): [M+H]$^+$ calculated for $C_{17}H_{21}N_2O_6$: 349.14. found: 349.13.

Step 2

To a mixture of compound 75 (62 mg, 0.178 mmol), compound 11 (95 mg, 0.445 mmol), and HATU (135 mg, 0.356 mmol) in dichloromethane (3 mL) was added N,N-diisopropylethylamine (0.186 mL, 1.07 mmol) at room temperature. After 0.5 h, the reaction mixture was diluted with dichloromethane, washed with 3% LiCl, saturated NH$_4$Cl, and 0.5 N HCl. The organic fraction was dried (Na$_2$SO$_4$) and concentrated. The residue was purified by column chromatography on silica gel using dichloromethane-20% methanol in dichloromethane as eluents to get compound 76. LCMS-ESI$^+$ (m/z): [M+H]$^+$ calculated for $C_{24}H_{25}ClF_2N_3O_5$: 508.15. found: 508.17.

Step 3

To a solution of compound 76 (60 mg, 0.118 mmol) in acetonitrile (5 mL) was added magnesium bromide (65 mg, 0.354 mmol) and the mixture was stirred at 50° C. for 30 min. After the mixture was cooled and acidified with 10% HCl, the product was extracted with ethyl acetate (×2). The combined organic extracts were dried (MgSO$_4$), concentrated, and purified by preparative HPLC (Acetonitrile/H$_2$O with 0.1% TFA modifier) to afford compound 77: $^1$H NMR (400 MHz, Chloroform-d) δ 8.45 (s, 1H), 7.29 (d, J=7.6 Hz, 1H), 6.95 (t, J=8.2 Hz, 1H), 4.71 (s, 2H), 4.51 (s, 1H), 4.30 (s, 1H), 4.14 (q, J=7.3 Hz, OH), 3.17-2.87 (m, 5H), 2.30 (d, J=9.5 Hz, 3H), 1.64 (s, 3H), 1.26 (d, J=4.3 Hz, 1H). LCMS-ESI$^+$ (m/z): [M+H]$^+$ calculated for $C_{23}H_{23}ClF_2N_3O_5$: 494.13. found: 494.18.

Example 18

Preparation of Compound 80

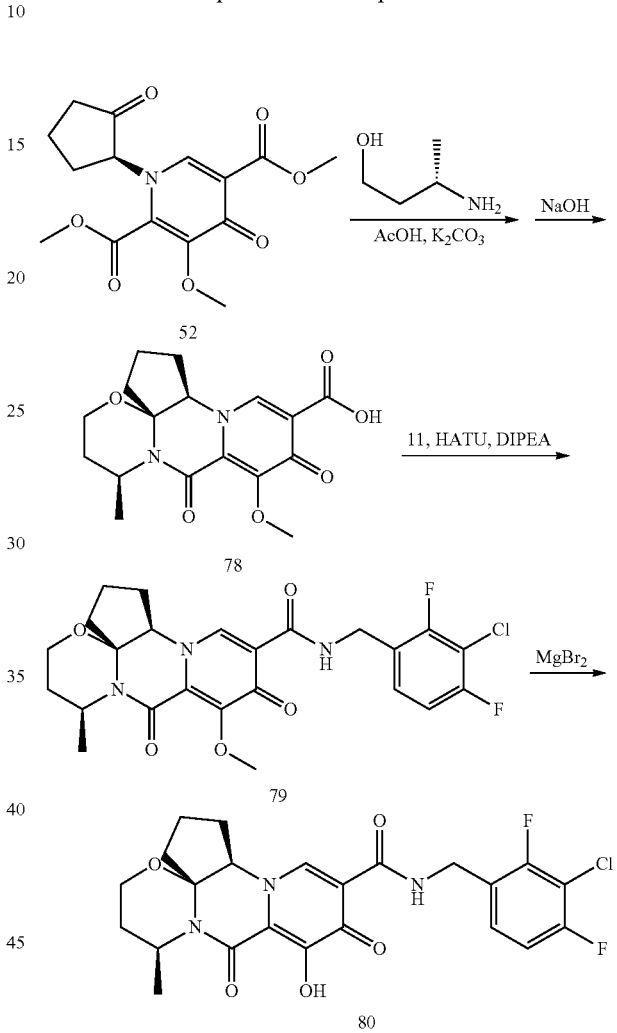

Step 1

To compound 52 (460 mg, 1.42 mmol) in acetonitrile (20 mL) were added acetic acid (1.0 mL, 17.47 mmol), potassium carbonate (0.8 g, 5.7 mmol) (S)-3-aminobutan-1-ol (0.39 mL, 4.27 mmol). After stirring at 70° C. for 24 h, it was concentrated and the residue was used for the next reaction.

The solution of the above residue in THF (20 mL), MeOH (2 mL), and 1 N NaOH (5 mL) was stirred at room temperature for 1 h. The resulting mixture was acidified with 3 N HCl and concentrated to dryness. The residue was purified by column chromatography on silica gel using dichloromethane-20% methanol in dichloromethane as eluents to get compound 78. LCMS-ESI$^+$ (m/z): [M+H]$^+$ calculated for $C_{17}H_{21}N_2O_6$: 349.14. found: 349.15.

Step 2

To a mixture of compound 78 (63 mg, 0.18 mmol), compound 11 (95 mg, 0.445 mmol), and HATU (135 mg, 0.356 mmol) in dichloromethane (3 mL) was added N,N-diisopropylethylamine (0.186 mL, 1.07 mmol) at room temperature. After 0.5 h, the reaction mixture was diluted with dichloromethane, washed with 3% LiCl, saturated NH$_4$Cl, and 0.5 N HCl. The organic fraction was dried (Na$_2$SO$_4$) and concentrated. The residue was purified by column chromatography on silica gel using dichloromethane-20% methanol in dichloromethane as eluents to get compound 79. LCMS-ESI$^+$ (m/z): [M+H]$^+$ calculated for C$_{24}$H$_{25}$ClF$_2$N$_3$O$_5$: 508.15. found: 508.18.

Step 3

To a solution of compound 76 (78 mg, 0.154 mmol) in acetonitrile (5 mL) was added magnesium bromide (85 mg, 0.461 mmol) and the mixture was stirred at 50° C. for 30 min. After the mixture was cooled and acidified with 10% HCl, the product was extracted with ethyl acetate (×2). The combined organic extracts were dried (MgSO$_4$), concentrated, and purified by preparative HPLC (acetonitrile/H$_2$O with 0.1% TFA modifier) to afford compound 80: $^1$H NMR (400 MHz, Acetonitrile-d$_3$) δ 8.26 (s, 1H), 7.39 (td, J=8.4, 6.1 Hz, 1H), 7.09 (td, J=8.8, 1.9 Hz, 1H), 4.65 (d, J=6.1 Hz, 2H), 3.68-3.38 (m, 2H), 3.21-2.58 (m, 5H), 1.96 (p, J=2.5 Hz, 12H), 1.55 (d, J=6.8 Hz, 3H), 1.29 (s, 1H). $^{19}$F NMR (377 MHz, Acetonitrile-d$_3$) δ −117.55 (d, J=7.3 Hz), −119.63 (d, J=8.1 Hz). LCMS-ESI$^+$ (m/z): [M+H]$^+$ calculated for C$_{23}$H$_{23}$ClF$_2$N$_3$O$_5$: 494.13. found: 494.19.

Example 19

Preparation of Compounds (88a and 88b)

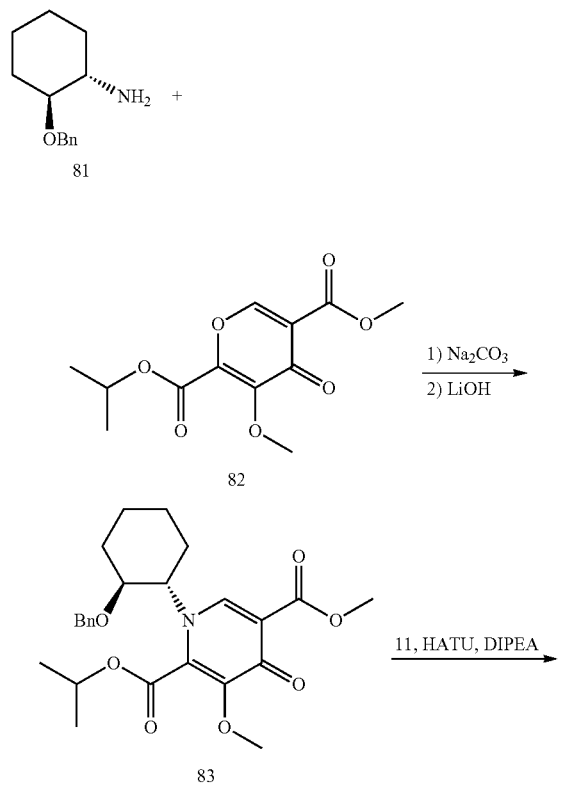

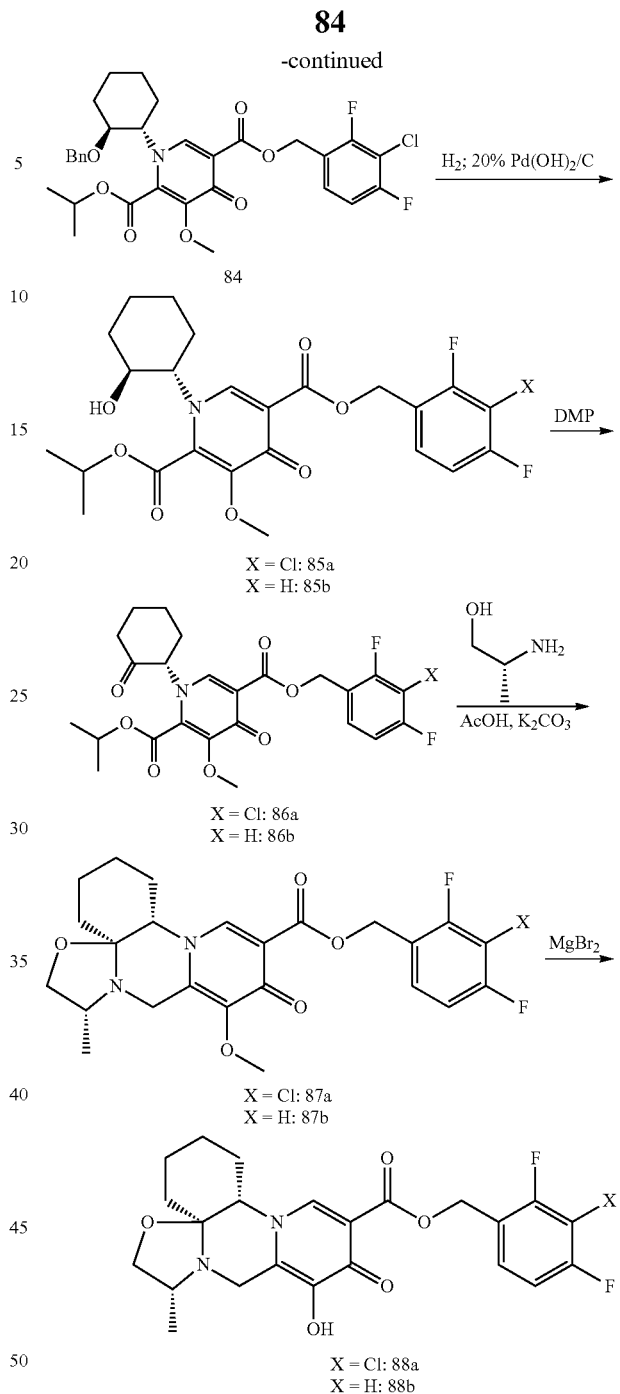

Step 1

To (1R,2R)-2-(benzyloxy)cyclohexanamine (81, 760 mg, 3.70 mmol), pyrone 82 (1.00 g, 3.7 mmol), and sodium bicarbonate (1.24 g, 15 mmol) in methanol (30 mL) and water (10 mL) was stirred at room temperature for 16 h. The mixture was evaporated to remove most of the methanol, diluted with water and the product was extracted with ethyl acetate. The organic extract was dried (Na$_2$SO$_4$) and concentrated. The residue was used as is for the next reaction. LCMS-ESI$^+$ (m/z): [M+H calculated for C$_{25}$H$_{31}$NO$_7$: 457.52. found: 458.16.

The solution of the above residue in THF (20 mL), MeOH (2 mL), and 1 M LiOH (3.28 mL) was stirred at room temperature for 1.5 h. The resulting mixture was acidified with 3 N HCl and concentrated to dryness. The residue was purified by preparative HPLC (acetonitrile/H$_2$O with 0.1% TFA modifier) to give compound 83. LCMS-ESI$^+$ (m/z): [M+H]$^+$ calculated for C$_{24}$H$_{29}$NO$_7$: 443.49. found: 444.16.

Step 2

To a mixture of compound 83 (406 mg, 0.92 mmol), compound 11 (587.84 mg, 2.75 mmol), and HATU (696 mg, 1.83 mmol) in dichloromethane (3 mL) was added N,N-Diisopropylethylamine (0.96 mL, 5.49 mmol) at room temperature. After 0.5 h, the reaction mixture was diluted with dichloromethane, washed with 3% LiCl, saturated NH$_4$Cl and 0.5 N HCl. The organic fraction was dried (Na$_2$SO$_4$) and concentrated. The residue was purified by column chromatography on silica gel using dichloromethane-20% methanol in dichloromethane as eluents to get compound 84. LCMS-ESI$^+$ (m/z): [M+H]$^+$ calculated for C$_{31}$H$_{33}$ClF$_2$N$_2$O$_6$: 603.05. found: 603.19.

Step 3

A mixture of compound 84 (34 mg, 0.056 mmol) and 20% palladium hydroxide on carbon (15 mg) in ethanol (4 mL) was stirred under hydrogen atmosphere for 0.5 h at room temperature. After the mixture was filtered through celite pad, the filtrate was concentrated to dryness and then co-evaporated with dichloromethane (×2) to get a mixture of compounds 85a and 85b. LCMS-ESI$^+$ (m/z): [M+H]$^+$ calculated for C$_{24}$H$_{28}$ClF$_2$N$_2$O$_6$: 513.16 and C$_{24}$H$_{29}$F$_2$N$_2$O$_6$: 479.20. found: 513.13 and 479.16.

Step 4

To a solution of the crude mixture of 85a and 85b in dichloromethane (5 mL) was added Dess-Martin periodinane (92.6 mg, 0.218 mmol). The mixture was stirred at room temperature for 20 min. After the reaction mixture was diluted with the mixture of saturated Na$_2$S$_2$O$_3$/saturated NaHCO$_3$ (7:1) and stirred for 10 min, the product was extracted with dichloromethane. After the organic extract was dried (Na$_2$SO$_4$) and concentrated, the residue was purified by column chromatography on silica gel using hexanes-ethyl acetate to afford the mixture of ketones 86a and 87b. LCMS-ESI$^+$ (m/z): [M+H]$^+$ calculated for C$_{24}$H$_{26}$ClF$_2$N$_2$O$_6$: 511.14, and C$_{24}$H$_{27}$F$_2$N$_2$O$_6$: 477.18. found: 511.12 and 477.16.

Step 5

To above ketones 86a and 86b mixture (46 mg) in acetonitrile (20 mL) were added acetic acid (0.1 mL, 1.75 mmol), potassium carbonate (50 mg, 0.36 mmol), and (R)-2-aminopropan-1-ol (27 mg, 0.36 mmol). After the reaction mixture was stirred at 70° C. for 27 h and concentrated, the residue was dissolved in methanol and concentrated with silica gel. The resulting adsorbed mixture was purified by column chromatography on silica gel using dichloromethane-20% methanol in dichloromethane as eluents to get the mixture of compounds 87a and 87b. LCMS-ESI$^+$ (m/z): [M+H]$^+$ calculated for C$_{24}$H$_{24}$ClF$_2$N$_3$O$_5$ and C$_{24}$H$_{25}$F$_2$N$_3$O$_5$:508.15 and 474.18. found: 508.17 and 474.27.

Step 6

To a solution of the mixture compounds 87a and 87b (30 mg) in acetonitrile (5 mL) was added magnesium bromide (33 mg, 0.177 mmol) and the mixture was stirred at 50° C. for 30 min. After the mixture was cooled and acidified with 10% HCl, the product was extracted with ethyl acetate (×2). The combined organic extracts were dried (MgSO$_4$), concentrated, and purified by preparative HPLC (acetonitrile/H$_2$O with 0.1% TFA modifier) to afford compounds 88a and 88b.

Compound 88a: 5 mg (17%), $^1$H NMR (400 MHz, Chloroform-d) δ 8.50 (s, 1H), 7.36-7.27 (m, 1H), 6.95 (t, J=8.3 Hz, 1H), 4.66 (d, J=47.2 Hz, 2H), 4.42 (s, 1H), 4.08 (d, J=13.9 Hz, 1H), 3.72 (dd, J=14.1, 9.8 Hz, 1H), 3.10 (d, J=16.4 Hz, 1H), 2.69 (s, OH), 2.48 (d, J=19.6 Hz, 3H), 1.80 (d, J=43.0 Hz, 4H), 1.33 (d, J=6.2 Hz, 3H), 1.31-1.22 (m, 1H). $^{19}$F NMR (377 MHz, Chloroform-d) δ −76.43, −114.57, −117.38. LCMS-ESI$^+$ (m/z): [M+H]$^+$ calculated for C$_{23}$H$_{23}$ClF$_2$N$_3$O$_5$: 494.13. found: 494.19.

Compound 88b: 5 mg (17%), $^1$H NMR (400 MHz, Chloroform-d) δ 8.54 (s, 1H), 7.39 (d, J=7.0 Hz, 1H), 6.90-6.68 (m, 2H), 4.78-4.26 (m, 4H), 4.12-3.96 (m, 1H), 3.81-3.58 (m, 1H), 2.53 (m, 2H), 1.80 (d, J=39.1 Hz, 5H), 1.32 (d, J=6.3 Hz, 3H), 1.23 (d, J=16.1 Hz, 3H). $^{19}$F NMR (377 MHz, Chloroform-d) δ −76.45, −111.84, −114.77. LCMS-ESI$^+$ (m/z): [M+H]$^+$ calculated for C$_{23}$H$_{24}$F$_2$N$_3$O$_5$: 460.17. found: 460.22.

Example 20

Preparation of Compound 94

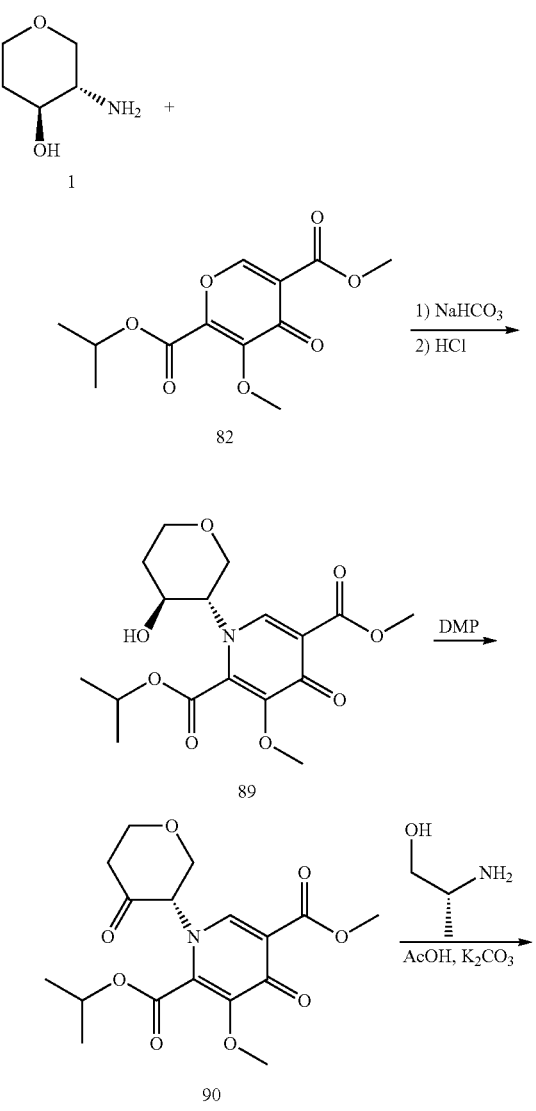

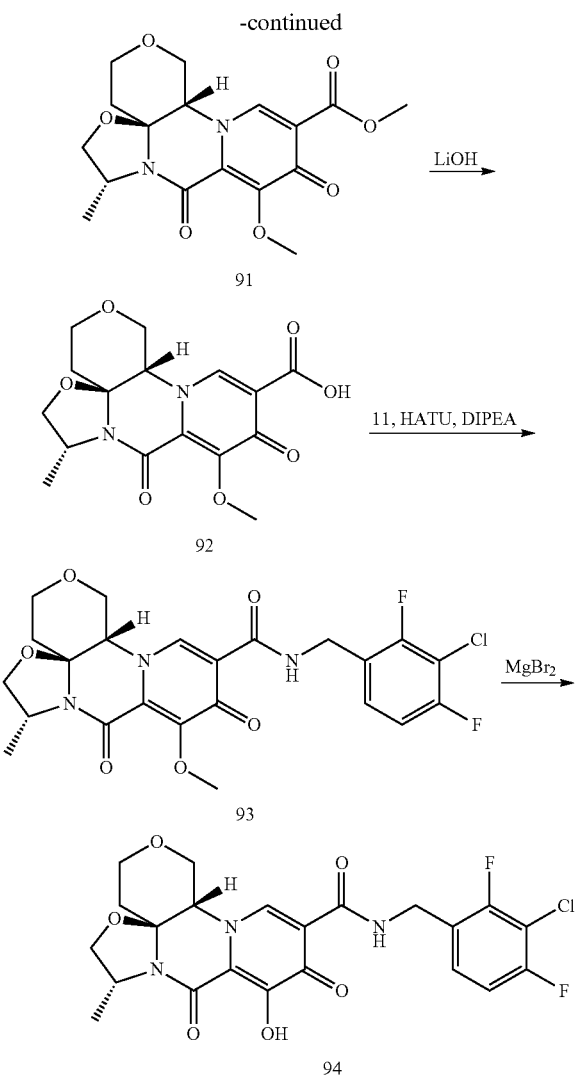

Step 1

To a mixture of compound 1 (43 mg, 0.367 mmol), compound 82 (97 mg, 0.359 mmol), and sodium bicarbonate (65 mg, 0.774 mmol) were added water (0.5 mL) and methanol (1 mL). The resulting mixture was stirred at room temperature for 16 h. The mixture was diluted with water and extracted with dichloromethane (×3). The organic fractions were washed with water (×1), combined, and dried (MgSO$_4$) to get the solution (~40 mL) of crude compound 89. This solution was used for the next reaction. LCMS-ESI$^+$ (m/z): [M+H$_2$O+H]$^+$ calculated C$_{17}$H$_{24}$NO$_8$: 370.15. found: 370.07.

Step 2

The solution of the crude compound 89 in dichloromethane was stirred at 0° C. bath as Dess-Martin periodinane (180 mg, 0.424 mmol) was added. After 5 min at 0° C., the mixture was stirred at room temperature. After 1.25 h, additional Dess-Martin periodinane (185 mg, 0.436 mmol) was added at room temperature. After another 1.75 h at room temperature, additional Dess-Martin periodinane (360 mg, 0.849 mmol) was added at room temperature. After 1.5 h, additional Dess-Martin periodinane (360 mg, 0.849 mmol) was added at room temperature. After 1.5 h, the reaction mixture was filtered through celite pad and the filtrate was concentrated. The residue was purified by column chromatography on silica gel (12 g column) using hexane-ethyl acetate-20% methanol in ethyl acetate as eluents and the product containing fractions were pooled and concentrated. The residue was further purified by preparative HPLC (acetonitrile/H$_2$O with 0.1% TFA modifier) to get compound 90. $^1$H NMR (400 MHz, Chloroform-d) δ 7.97 (s, 1H), 5.40 (s, 1H), 5.28 (p, J=6.3 Hz, 1H), 4.69 (dd, J=10.5, 6.8 Hz, 1H), 4.61-4.47 (m, 1H), 4.43-4.28 (m, 1H), 4.00 (d, J=10.6 Hz, 1H), 3.96 (s, 3H), 3.88 (s, 3H), 2.81 (ddd, J=15.2, 12.2, 7.4 Hz, 1H), 2.66 (ddd, J=15.1, 2.9, 1.4 Hz, 1H), 1.38 (dd, J=10.8, 6.3 Hz, 6H). LCMS-ESI$^+$ (m/z): [M+H]$^+$ calculated C$_{17}$H$_{22}$NO$_8$: 368.13. found: 368.03.

Step 3

A mixture of compound 90 (15 mg, 0.041 mmol), (−)-(R)-2-aminopropanol (17 mg, 0.226 mmol), and potassium carbonate (26 mg, 0.188 mmol) in acetonitrile (1 mL) was stirred at room temperature as acetic acid (0.1 mL, 0.175 mmol) was added. The flask was closed tightly and stirred at 60° C. for 2 h and 70° C. bath for 19 h. The reaction mixture was concentrated and the residue was dissolved in DMF, filtered, and the filtrate was purified by preparative HPLC (acetonitrile/H$_2$O with 0.1% TFA modifier) to get compound 91. $^1$H NMR (400 MHz, Chloroform-d) δ 8.48 (s, 1H), 4.66 (d, J=14.5 Hz, 1H), 4.54 (h, J=6.7 Hz, 1H), 4.36 (dd, J=9.0, 7.0 Hz, 1H), 4.19 (dd, J=14.5, 1.6 Hz, 1H), 4.06 (s, 3H), 3.89 (s, 4H), 3.81 (dd, J=9.0, 6.9 Hz, 1H), 3.79-3.70 (m, 2H), 1.94-1.66 (m, 2H), 1.43 (d, J=6.4 Hz, 3H). LCMS-ESI$^+$ (m/z): [M+H]$^+$ calculated C$_{17}$H$_{21}$N$_2$O$_7$: 365.13. found: 365.11.

Step 4

To a mixture of compound 91 (8 mg, 0.022 mmol) in methanol (1 mL) and THF (1 mL) was added 1 N LiOH (0.1 mL) at room temperature and the resulting mixture was stirred at rt for 16.5 h. The resulting solution was concentrated to remove methanol and THF and the residue was dissolved in water, acidified with 1 N HCl, and further diluted with DMF. The solution was purified by preparative HPLC (acetonitrile/H$_2$O with 0.1% TFA modifier) and the fraction containing the acid was concentrated to dryness, co-evaporated with toluene (×2), and dried in vacuum for ~30 min to get compound 92. LCMS-ESI$^+$ (m/z): [M+H]$^+$ calculated C$_{16}$H$_{19}$N$_2$O$_7$: 351.12. found: 351.08.

Step 5

To a solution of compound 92 (7 mg, 0.020 mmol), compound 11 (12 mg, 0.056 mmol), and HATU (27 mg, 0.071 mmol) in dichloromethane (2 mL) was added N,N-diisopropylethylamine (0.07 mL, 0.402 mmol) at rt. After 30 min, the mixture was diluted with ethyl acetate (~15 mL), washed with saturated NH$_4$Cl (×2), saturated NaHCO$_3$ (×2), and brine (×1). After the aqueous fractions were extracted with ethyl acetate (×1), the organic fractions were combined, dried (MgSO$_4$), and concentrated. The residue was purified by column chromatography on silica gel (12 g column) using hexanes-ethyl acetate-20% methanol in ethyl acetate as eluents to get compound 93. $^1$H NMR (400 MHz, Chloroform-d) δ 10.42 (s, 1H), 8.74 (s, 1H), 7.31 (td, J=8.3, 6.1 Hz, 1H), 6.93 (td, J=8.5, 1.8 Hz, 1H), 4.76-4.68 (m, 1H), 4.63 (td, J=15.5, 14.4, 6.1 Hz, 2H), 4.54 (q, J=6.6 Hz, 1H), 4.35 (dd, J=9.0, 7.0 Hz, 1H), 4.20-4.13 (m, 1H), 4.08 (s, 3H), 3.91-3.84 (m, 1H), 3.81 (dd, J=9.0, 6.9 Hz, 1H), 3.75 (dd, J=11.4, 3.6 Hz, 1H), 3.70 (d, J=2.8 Hz, 1H), 1.84-1.70 (m, 2H), 1.45 (d, J=6.3 Hz, 3H). $^{19}$F NMR (376 MHz, Chloroform-d) δ −114.98 (s, 1F), −117.38 (s, 1F). LCMS-ESI$^+$ (m/z): [M+H]$^+$ calculated C$_{23}$H$_{23}$ClF$_2$N$_3$O$_6$: 510.12. found: 510.11.

Step 6

To a solution of compound 93 (4.7 mg, 0.009 mmol) in MeCN (1 mL) was added MgBr$_2$ (7.8 mg, 0.042 mmol) at rt and the resulting mixture was stirred at 50° C. bath. After 30 min, the reaction mixture was stirred at 0° C. and added 1 N HCl to make the mixture a solution and diluted with water before the product was extracted with dichloromethane (×3). After the combined extracts were dried (MgSO$_4$) and concentrated, the residue was purified by column chromatography on silica gel (12 g column) using dichloromethane-20% methanol in dichloromethane as eluents to get compound 94. $^1$H NMR (400 MHz, Chloroform-d) δ 11.62 (s, 1H), 10.37 (s, 1H), 8.71 (s, 1H), 7.35-7.27 (m, 1H), 6.92 (td, J=8.5, 1.9 Hz, 1H), 4.76 (d, J=14.4 Hz, 1H), 4.70-4.61 (m, 2H), 4.51 (p, J=6.4 Hz, 1H), 4.44 (dd, J=8.9, 7.3 Hz, 1H), 4.19-4.11 (m, 1H), 3.97-3.90 (m, 1H), 3.87 (dd, J=8.8, 6.5 Hz, 1H), 6.89-6.87 (m, OH), 3.76 (td, J=11.9, 2.7 Hz, 1H), 3.71 (d, J=2.1 Hz, 1H), 1.88 (td, J=13.1, 12.2, 5.2 Hz, 1H), 1.80 (d, J=14.3 Hz, 1H), 1.51 (d, J=6.3 Hz, 3H). $^{19}$F NMR (376 MHz, Chloroform-d) δ -115.17 (d, J=7.1 Hz, 1F), -117.41 (d, J=7.7 Hz, 1F). LCMS-ESI$^+$ (m/z): [M+H]$^+$ calculated C$_{22}$H$_{21}$ClF$_2$N$_3$O$_6$: 496.11. found: 496.08.

Example 21

Preparation of Compound 96

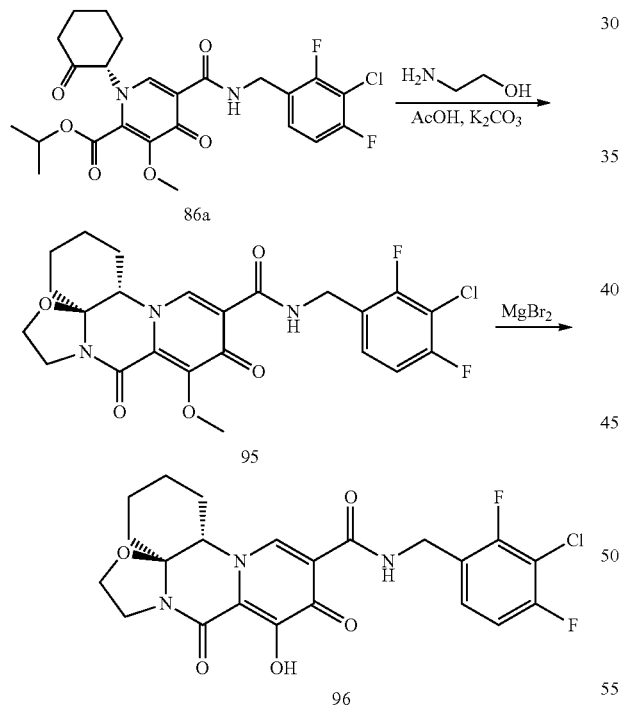

Step 1

To compound 86a (95 mg, 0.186 mmol, contained small amount of 86b) in acetonitrile (10 mL) were added acetic acid (0.5 mL, 8.73 mmol), potassium carbonate (114 mg, 0.825 mmol), and 2-aminoethanol (62 mg, 1.02 mmol). After stirring at 70° C. for 24 h, the mixture was dissolved by methanol and concentrated with silica gel. The resulting adsorbed mixture was purified by column chromatography on silica gel using dichloromethane-20% methanol in dichloromethane as eluents to get racemic compound 95.

LCMS-ESI$^+$ (m/z): [M+H]$^+$ calculated for C$_{23}$H$_{23}$ClF$_2$N$_3$O$_5$: 494.13. found: 494.21.

Step 2

To a solution of compound 95 (59 mg, 0.119 mmol) in acetonitrile (5 mL) was added magnesium bromide (66 mg, 0.358 mmol) and the mixture was stirred at 50° C. for 30 min. After the mixture was cooled and acidified with 10% HCl, the product was extracted with ethyl acetate (×2). The combined organic extracts were dried (MgSO$_4$), concentrated, and purified by preparative HPLC (acetonitrile/H$_2$O with 0.1% TFA modifier) to afford racemic compound 96. $^1$H NMR (400 MHz, Chloroform-d) δ 10.58 (d, J=7.2 Hz, 1H), 8.57 (s, 1H), 7.30 (t, J=7.7 Hz, 1H), 7.00-6.85 (m, 1H), 4.66 (d, J=5.2 Hz, 2H), 4.20-3.88 (m, 2H), 2.91-2.50 (m, 2H), 2.36 (t, J=7.5 Hz, 1H), 1.88 (d, J=13.1 Hz, 2H), 1.62 (q, J=7.4 Hz, 1H), 1.25, 0.95-0.63 (m, 3H). $^{19}$F NMR (377 MHz, Chloroform-d) δ -76.43, -114.27, -117.28. LCMS-ESI$^+$ (m/z): [M+H]$^+$ calculated for C$_{22}$H$_{21}$ClF$_2$N$_3$O$_5$: 480.11. found: 480.17.

Example 22

Preparation of Compound 100

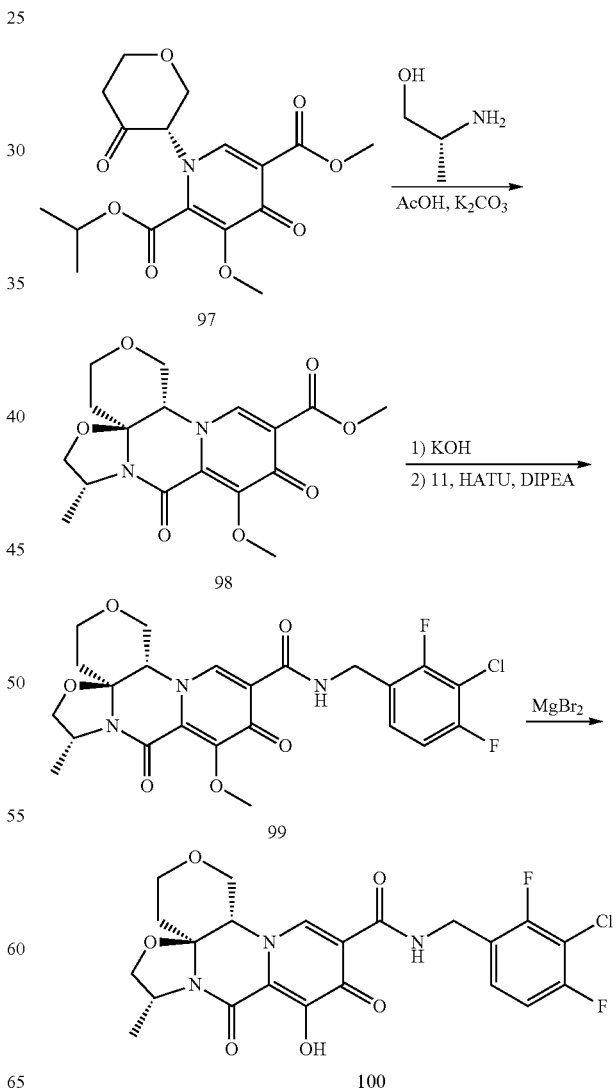

Step 1

To compound 97 (0.05 g, 0.14 mmol), which was prepared by the same procedure as compound 90, in acetonitrile (3 mL) were added acetic acid (0.3 mL, 5.24 mmol), potassium carbonate (0.08 g, 0.58 mmol), and (R)-2-aminopropan-1-ol (0.04 g, 0.54 mmol). After stirring at 70° C. for 17 h, the reaction mixture was cooled down to room temperature and filtered. The crude solution was purified by preparative HPLC (acetonitrile/H$_2$O with 0.1% TFA modifier) to get compound 98. LCMS-ESI$^+$ (m/z): [M+H]$^+$ calculated for C$_{17}$H$_{21}$N$_2$O$_7$: 365.13. found: 365.

Step 2

A mixture of compound 98 (5 mg, 0.014 mmol) in THF (0.5 mL), methanol (0.5 mL), and 1 N KOH (0.1 mL) was stirred at room temperature for 1 h. After the resulting mixture was acidified with 1 N HCl it was concentrated to dryness and co-evaporated with toluene (×3). The resulting crude acid was used for the next reaction as is.

To a mixture of the above crude acid, compound 11 (6 mg, 0.028 mmol), and HATU (10 mg, 0.028 mmol) in dichloromethane (1 mL) was added N,N-diisopropylethylamine (0.009 g, 0.07 mmol) at room temperature. After 2 h, the reaction mixture was concentrated and the crude residue was purified by preparative HPLC (acetonitrile/H$_2$O with 0.1% TFA modifier) to get compound 99. LCMS-ESI$^+$ (m/z): [M+H]$^+$ calculated for C$_{23}$H$_{23}$ClF$_2$N$_3$O$_6$: 510.12. found: 510.

Step 3

To a solution of compound 99 (3 mg, 0.006 mmol) in acetonitrile (2 mL) was added magnesium bromide (0.01 g, 0.054 mmol) and the mixture was stirred at 50° C. for 30 min. After the mixture was cooled down to 0° C. and acidified with 1 N HCl, the resulting solution was purified by preparative HPLC (acetonitrile/H$_2$O with 0.1% TFA modifier) to afford compound 100. $^1$H NMR (400 MHz, Chloroform-d) δ 10.38 (d, J=6.2 Hz, 1H), 8.54 (s, 1H), 7.45-7.19 (m, 1H), 6.94 (td, J=8.7, 1.8 Hz, 1H), 4.81-4.60 (m, 1H), 4.61-4.39 (m, 1H), 4.29-4.05 (m, 2H), 4.05-3.83 (m, 2H), 3.79-3.66 (m, 1H), 3.62-3.37 (m, 1H), 3.29 (d, J=12.8 Hz, 1H), 3.20-3.07 (m, 1H), 2.70 (d, J=10.5 Hz, 2H), 2.36 (d, J=7.4 Hz, 1H), 1.44 (d, J=6.2 Hz, 3H). $^{19}$F NMR (376 MHz, Chloroform-d) δ –113.81--116.52 (m, 1F), –117.29 (m, 1F). LCMS-ESI$^+$ (m/z): [M+H]$^+$ calculated for C$_{22}$H$_{21}$ClF$_2$N$_3$O$_6$: 496.11. found: 496.

Example 23

Preparation of Compound 103

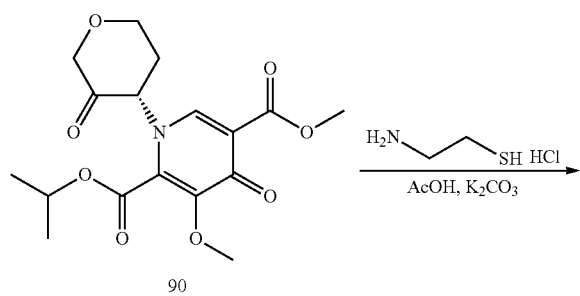

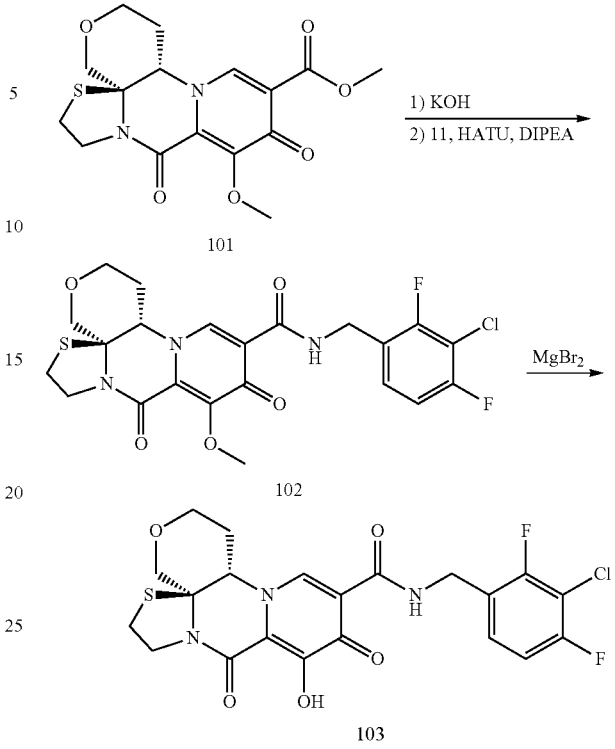

Step 1

To compound 90 (0.05 g, 0.14 mmol) in acetonitrile (3 mL) were added 2-aminoethanethiol HCl salt (0.06 g, 0.54 mmol), potassium carbonate (0.08 g, 0.58 mmol) and acetic acid (0.3 mL, 5.24 mmol). After stirring at 70° C. for 17 h, the mixture was cooled down to room temperature and filtered. The filtrate was purified by preparative HPLC (acetonitrile/H$_2$O with 0.1% TFA modifier) to give racemic compound 101. LCMS-ESI$^+$ (m/z): [M+H]$^+$ calculated for C$_{16}$H$_{19}$N$_2$O$_6$S: 367.10. found: 367.

Step 2

A mixture of compound 101 (0.01 g, 0.028 mmol) in THF (0.5 mL), methanol (0.5 mL), and 1 N KOH (0.1 mL) was stirred at room temperature for 1 h. After the resulting mixture was acidified with 3 N HCl it was concentrated to dryness and co-evaporated with toluene (×3). The resulting crude acid was used for the next reaction as is.

To a mixture of the above crude acid, compound 11 (0.01 g, 0.056 mmol), and HATU (0.02 g, 0.056 mmol) in dichloromethane (1 mL) was added N,N-diisopropylethylamine (0.02 g, 0.15 mmol) at room temperature. After 2 h, the reaction mixture was concentrated and the crude residue was purified by preparative HPLC (acetonitrile/H$_2$O with 0.1% TFA modifier) to get racemic compound 102. LCMS-ESI$^+$ (m/z): [M+H]$^+$ calculated for C$_{22}$H$_{21}$ClF$_2$N$_3$O$_5$S: 512.09. found: 512.

Step 3

To a solution of compound 102 (0.005 g, 0.01 mmol) in acetonitrile (2 mL) was added magnesium bromide (0.01 g, 0.054 mmol) and the mixture was stirred at 50° C. for 30 min. After the mixture was cooled down to 0° C. and acidified with 1 N HCl, the resulting solution was purified by preparative HPLC (Acetonitrile/H$_2$O with 0.1% TFA modifier) to afford racemic compound 103. $^1$H NMR (400 MHz, Chloroform-d) δ 10.57 (m, 1H), 8.60 (s, 1H), 7.26 (m, 1H), 7.12-6.92 (m, 1H), 4.77 (ddd, J=12.5, 6.3, 4.0 Hz, 1H), 4.67

(d, J=5.4 Hz, 2H), 4.49 (s, 1H), 4.14-3.93 (m, 1H), 3.86-3.72 (m, 2H), 3.66-3.43 (m, 2H), 3.33-3.00 (m, 2H), 2.83 (d, J=16.5 Hz, 1H), 2.56 (d, J=14.3 Hz, 1H), 2.01 (m, 1H). $^{19}$F NMR (376 MHz, Chloroform-d) δ −114.36 (m, 1F), −117.06 (m, 1F). LCMS-ESI$^+$ (m/z): [M+H]$^+$ calculated for $C_{21}H_{19}ClF_2N_3O_5S$: 498.07. found: 498.

Example 24

Preparation of Compound 110a and 110b

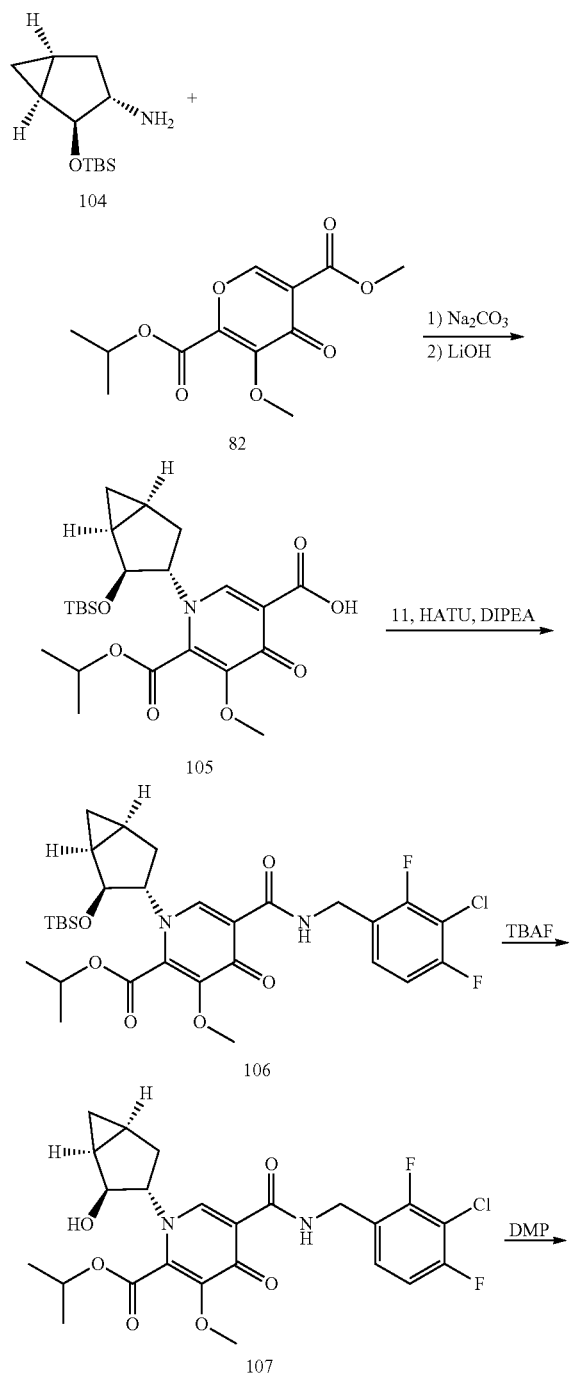

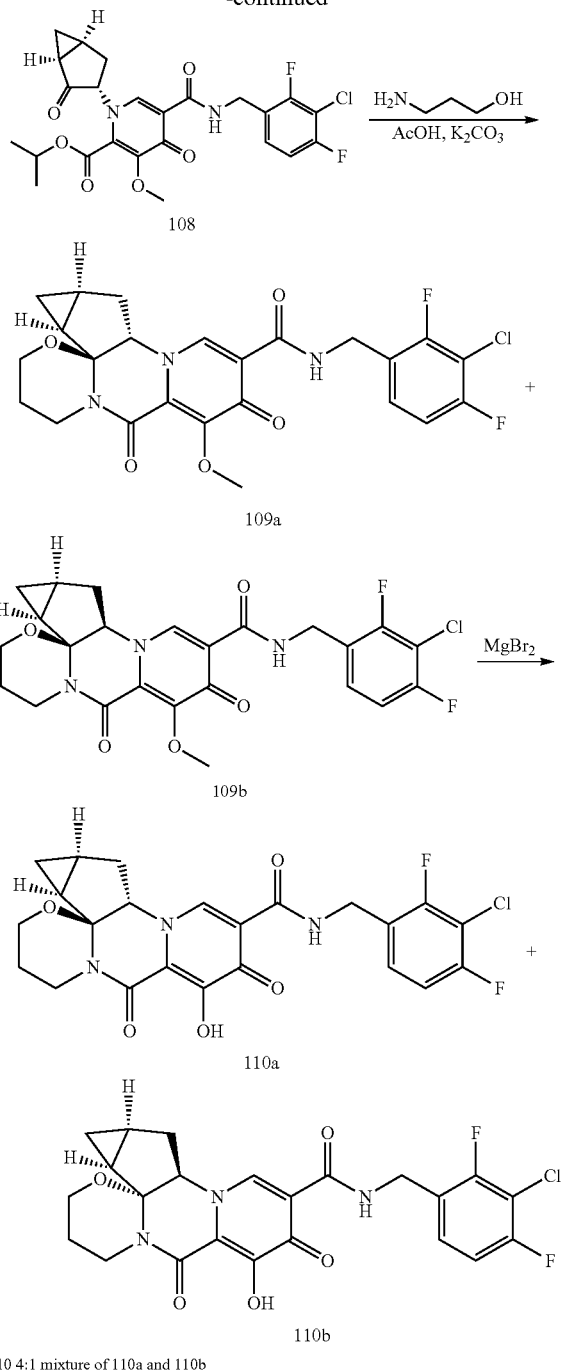

110 4:1 mixture of 110a and 110b

Step 1

A mixture of (1S,2S,3S,5S)-2-((tert-butyldimethylsilyl)oxy)bicyclo[3.1.0]hexan-3-amine (104, 795.27 mg, 3.5 mmol), pyrone 82 (0.9 g, 3.33 mmol), and sodium bicarbonate (1.12 g, 13.3 mmol) in methanol (80 mL) and water (20 mL) was stirred at room temperature for 16 h. After the mixture was evaporated to remove most of the methanol, the resulting aqueous residue was diluted with water and the product was extracted with EtOAc. The organic extract was dried (Na$_2$SO$_4$) and concentrated to afford crude adduct which was used as is for the next reaction. LCMS-ESI$^+$ (m/z): [M+H]$^+$ calculated for $C_{24}H_{38}NO_7Si$: 480.24. found: 480.19.

To the above adduct (1.40 g, 2.92 mmol) in THF (20 mL) and methanol (5 mL) was added 1M LiOH (3 mL), and the mixture was stirred at room temperature for 1.5 h. The mixture was acidified with 3 N HCl and concentrated to dryness. The residue was purified by column chromatography on silica gel using hexane-ethyl acetate as eluents to get compound 105. LCMS-ESI$^+$ (m/z): [M+H]$^+$ calculated for $C_{23}H_{36}NO_7Si$: 466.23. found: 466.19.

Step 2

To a mixture of compound 105 (515 mg, 1.106 mmol), compound 11 (473 mg, 2.21 mmol), and HATU (841 mg, 2.21 mmol) in dichloromethane (13 mL) was added N,N-diisopropylethylamine (1.12 ml, 6.63 mmol). After 0.5 h, the mixture was diluted with dichloromethane, washed with 3% LiCl, saturated NH$_4$Cl and 0.5 N HCl. The organic fraction was dried (Na$_2$SO$_4$) and concentrated. The residue was purified by column chromatography on silica gel using dichloromethane-20% methanol in dichloromethane as eluents to get compound 106. LCMS-ESI$^+$ (m/z): [M+H]$^+$ calculated for $C_{30}H_{40}ClF_2N_2O_6Si$: 625.23. found: 625.21.

Step 3

To a solution of compound 106 (452 mg, 0.72 mmol) in THF (20 mL) was added 1 M tetrabutylammonium fluoride hydrate in THF (0.8 mL, 0.80 mmol) at room temperature under nitrogen atmosphere. After 20 min, the mixture was quenched with saturated NH$_4$Cl solution and acidified with 10% HCl to pH<3 before the product was extracted with ethyl acetate. After the extract was dried (Mg$_2$SO$_4$) and concentrated, the residue was purified by column chromatography on silica gel using hexanes-ethyl acetate as eluents to afford compound 107. LCMS-ESI$^+$ (m/z): [M+H]$^+$ calculated for $C_{24}H_{26}ClF_2N_2O_6$: 511.14. found: 511.13.

Step 4

To a solution of compound 107 (100 mg, 0.196 mmol) in dichloromethane (5 mL) was added Dess-Martin periodinane (332.06 mg, 0.78 mmol). After the mixture was stirred at room temperature for 20 min, a mixture of saturated Na$_2$S$_2$O$_3$/saturated NaHCO$_3$ (7:1) was added to the mixture, which was stirred for 10 min. The product was extracted with dichloromethane and the extract was dried (Na$_2$SO$_4$) and concentrated to afford the crude compound 108. LCMS-ESI$^+$ (m/z): [M+H]$^+$ calculated for $C_{24}H_{24}ClF_2N_2O_6$: 509.13. found: 509.12.

Step 5

To a solution of the above crude 108 in acetonitrile (10 mL) were added 3-aminopropan-1-ol (0.06 ml, 0.78 mmol), acetic acid (0.5 mL, 8.73 mmol), and potassium carbonate (108 mg, 0.784 mmol). After stirring at 70° C. for 24 h, the reaction mixture was diluted with methanol and concentrated with silica gel. The resulting adsorbed mixture was purified by column chromatography on silica gel using dichloromethane-20% methanol in dichloromethane as eluents to get 109 (a mixture of the two diastereomers 109a and 109b). LCMS-ESI$^+$ (m/z): [M+H]$^+$ calculated for $C_{24}H_{23}ClF_2N_3O_5$: 506.13. found: 506.18.

Step 6

To a solution of 109 (10 mg, 0.020 mmol) in acetonitrile (5 mL) was added magnesium bromide (11 mg, 0.060 mmol). The reaction mixture was stirred at 50° C. for 30 min, acidified with 10% HCl, and extracted with ethyl acetate (×2). After the combined organic fractions were dried (MgSO$_4$) and concentrated, the residue was purified by preparative HPLC (acetonitrile/H$_2$O with 0.1% TFA modifier) to afford 110 (4:1 mixture of 110a and 110b). $^1$H NMR (400 MHz, Methanol-d4) δ 8.22 (s, 1H), 7.39 (q, J=7.5 Hz, 1H), 7.08 (t, J=8.5 Hz, 1H), 4.67 (s, 2H), 4.58-3.56 (m, 4H), 3.23 (d, J=17.2 Hz, 1H), 3.14-2.93 (m, 1H), 2.45 (d, J=25.2 Hz, 1H), 2.34-1.87 (m, 3H), 1.46-1.13 (m, 3H), 0.82 (dd, J=55.8, 6.7 Hz, 1H), 0.61 (q, J=3.9 Hz, 1H). $^{19}$F NMR (376 MHz, Methanol-d4) δ −77.72 (d, J=256.2 Hz), −116.59-−117.81 (m), −119.77. LCMS-ESI$^+$ (m/z): [M+H]$^+$ calculated for $C_{23}H_{21}ClF_2N_3O_5$: 492.11. found: 492.14.

Example 25

Antiviral Assays in MT4 Cells

For the antiviral assay utilizing MT4 cells, 0.4 µL of 189X test concentration of 3-fold serially diluted compound in DMSO was added to 40 µl of cell growth medium (RPMI 1640, 10% FBS, 1% penicillin/streptomycin, 1% L-Glutamine, 1% HEPES) in each well of 384-well assay plates (10 concentrations) in quadruplicate.

1 mL aliquots of 2×10$^6$ MT4 cells are pre-infected for 1 and 3 hours respectively at 37° C. with 25 µL (MT4) or of either cell growth medium (mock-infected) or a fresh 1:250 dilution of an HIV-IIIb concentrated ABI stock (0.004 m.o.i. for MT4 cells). Infected and uninfected cells are diluted in cell growth medium and 35 µL of 2000 (for MT4) cells is added to each well of the assay plates.

Assay plates were then incubated in a 37° C. incubator. After 5 days of incubation, 25 µL of 2× concentrated CellTiter-Glo™ Reagent (catalog # G7573, Promega Biosciences, Inc., Madison, Wis.) was added to each well of the assay plate. Cell lysis was carried out by incubating at room temperature for 2-3 minutes, and then chemiluminescence was read using the Envision reader (PerkinElmer).

Compounds of the present disclosure demonstrate antiviral activity in this assay as depicted in Table 1 below. Accordingly, the compounds of the embodiments disclosed herein may be useful for treating the proliferation of the HIV virus, treating AIDS, or delaying the onset of AIDS or ARC symptoms.

TABLE 1

| Compound | EC$_{50}$ (nM) | CC$_{50}$ (nM) |
| --- | --- | --- |
| 110 | 3.754 | 20221 |
| 48 | 4.128 | 9061.4 |
| 103 | 1.195 | 10805 |
| 41 | 2.378 | 9190.8 |
| 42 | 3.491 | 7479.2 |
| 100 | 1.82 | 7525.4 |
| 96 | 4.427 | 1368.8 |
| 94 | 1.879 | 3991.7 |
| 88b | 2.096 | 7274.5 |
| 88a | 2.07 | 4604.6 |
| 80 | 11.805 | 17489 |
| 31 | 1.941 | 33585 |
| 30 | 2.59 | 33138 |
| 77 | 7.016 | 7271.4 |
| 26 | 2.629 | 22089 |
| 25 | 2.415 | 22106 |
| 57 | 3.198 | 3901.7 |
| 56 | 2.703 | 5761.4 |
| 15 | 4.639 | 7522 |
| 14 | 4.622 | 8015 |
| 74 | 3.167 | 5767.8 |
| 73 | 3.825 | 3319.9 |
| 69 | 8.022 | 15635 |
| 70 | 4.701 | 16413 |
| 65 | 4.127 | 5530.8 |
| 66 | 2.532 | 6915.9 |
| 61 | 3.753 | 8807.2 |
| 60 | 2.53 | 4936.4 |

The data in Table 1 represents an average over time of each assay for each compound. For certain compounds, multiple assays have been conducted over the life of the project.

All of the U.S. patents, U.S. patent application publications, U.S. patent applications, foreign patents, foreign patent applications and non-patent publications referred to in this specification are incorporated herein by reference, in their entirety to the extent not inconsistent with the present description.

From the foregoing it will be appreciated that, although specific embodiments have been described herein for purposes of illustration, various modifications may be made without deviating from the spirit and scope of the disclosure. Accordingly, the disclosure is not limited except as by the appended claims.

We claim:

1. A compound of Formula (Ia)

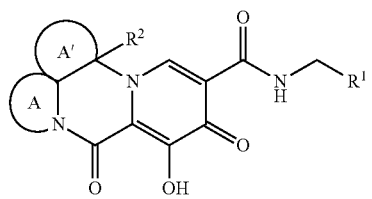

(Ia)

or a pharmaceutically acceptable salt thereof, wherein:
A is a 4 to 7 membered monocyclic heterocyclyl saturated or partially unsaturated and optionally substituted with 1 to 5 $R^3$ groups;
each $R^3$ is independently selected from the group consisting of $C_{1-4}$alkyl, halogen and oxo; or two $R^3$ connected to the same or adjacent carbon atoms form a spiro or fused $C_{3-6}$cycloalkyl or 4 to 6 membered heterocyclyl ring;
A' is selected from the group consisting of $C_{3-7}$ monocyclic cycloalkyl and 4 to 7 membered monocyclic heterocyclyl; wherein each $C_{3-7}$ monocyclic cycloalkyl and 4 to 7 membered monocyclic heterocyclyl is optionally substituted with 1 to 5 $R^4$ groups;
each $R^4$ is independently selected from the group consisting of $C_{1-4}$alkyl, halogen and oxo; or two $R^4$ connected to the same or adjacent carbon atoms form a spiro or fused $C_{3-6}$cycloalkyl or 4 to 6 membered heterocyclyl ring;
$R^1$ is phenyl optionally substituted with 1 to 5 $R^5$ groups;
each $R^5$ is independently selected from the group consisting of halogen and $C_{1-3}$alkyl; and
$R^2$ is selected from the group consisting of H, $C_{1-3}$haloalkyl and $C_{1-4}$alkyl.

2. The compound of claim 1, or a pharmaceutically acceptable salt thereof, wherein A is a 5 or 6 membered monocyclic heterocyclyl saturated or partially unsaturated and optionally substituted with 1 to 5 $R^3$ groups.

3. The compound of claim 1, or a pharmaceutically acceptable salt thereof, wherein A is selected from the group consisting of oxazolidinyl, piperidinyl, 3,4-unsaturated piperidinyl, pyrrolidinyl, tetrahydro-1,3-oxazinyl and thiazolidinyl; each of which is optionally substituted with 1 to 5 $R^3$ groups.

4. The compound of claim 1, or a pharmaceutically acceptable salt thereof, wherein A is selected from the group consisting of oxazolidinyl, piperidinyl, 3,4-unsaturated piperidinyl, pyrrolidinyl, tetrahydro-1,3-oxazinyl and thiazolidinyl; each of which is optionally substituted with one or two $R^3$ groups; wherein $R^3$ is $C_{1-4}$alkyl; or two $R^3$ connected to the same or adjacent carbon atoms form a spiro or fused $C_{3-6}$cycloalkyl or 4 to 6 membered heterocyclyl ring.

5. The compound of claim 1, or a pharmaceutically acceptable salt thereof, wherein A is selected from the group consisting of oxazolidinyl, piperidinyl, 3,4-unsaturated piperidinyl, pyrrolidinyl, tetrahydro-1,3-oxazinyl and thiazolidinyl; each of which is optionally substituted with methyl.

6. The compound of claim 1, or a pharmaceutically acceptable salt thereof, wherein

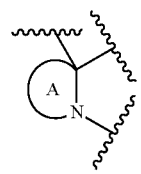

is selected from the group consisting of:

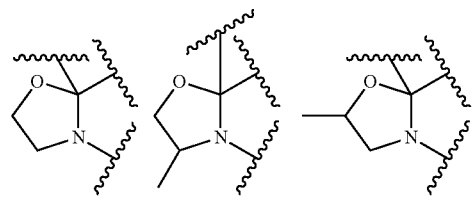

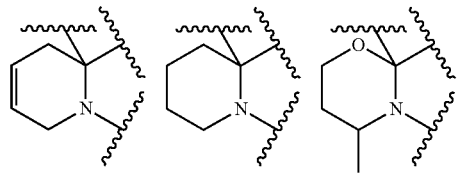

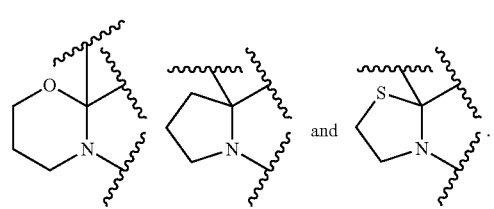

and .

7. The compound of claim 1, or a pharmaceutically acceptable salt thereof, wherein

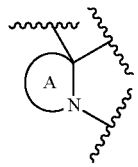

is selected from the group consisting of:

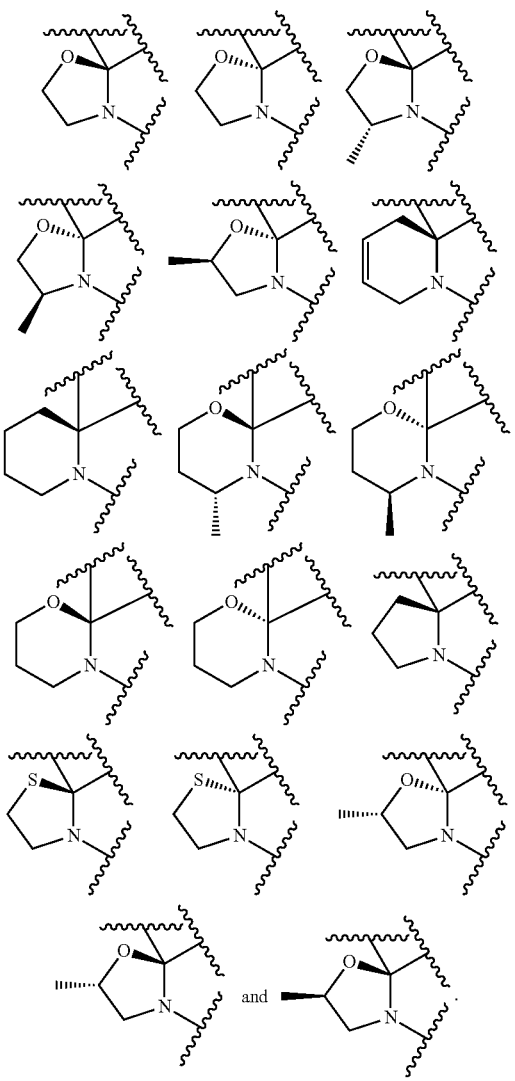

8. The compound of claim 1, or a pharmaceutically acceptable salt thereof, wherein A' is selected from the group consisting of $C_{5-6}$ monocyclic cycloalkyl and 5 to 6 membered monocyclic heterocyclyl; wherein each $C_{5-6}$ monocyclic cycloalkyl and 5 to 6 membered monocyclic heterocyclyl is optionally substituted with 1 to 5 $R^4$ groups.

9. The compound of claim 1, or a pharmaceutically acceptable salt thereof, wherein A' is selected from the group consisting of cyclopentyl, tetrahydrofuranyl, cyclohexyl and tetrahydropyranyl; each of which is optionally substituted with 1 to 5 $R^4$ groups.

10. The compound of claim 1, or a pharmaceutically acceptable salt thereof, wherein A' is selected from the group consisting of cyclopentyl, tetrahydrofuranyl, cyclohexyl and tetrahydropyranyl; each of which is optionally substituted with one or two $R^4$ groups, wherein each $R^4$ is independently selected from the group consisting of $C_{1-4}$alkyl, halogen and oxo; or two $R^2$ connected to the same or adjacent carbon atoms form a spiro or fused $C_{3-6}$cycloalkyl or 4 to 6 membered heterocyclyl ring.

11. The compound of claim 1, or a pharmaceutically acceptable salt thereof, wherein A' is selected from the group consisting of cyclopentyl, tetrahydrofuranyl, cyclohexyl and tetrahydropyranyl; each of which is optionally fused with a $C_{3-6}$cycloalkyl ring.

12. The compound of claim 1, or a pharmaceutically acceptable salt thereof, wherein A' is selected from the group consisting of cyclopentyl, tetrahydrofuranyl, cyclohexyl and tetrahydropyranyl; each of which is optionally fused with a cyclopropyl group.

13. The compound of claim 1, or a pharmaceutically acceptable salt thereof, wherein $R^2$ is H.

14. The compound of claim 1, or a pharmaceutically acceptable salt thereof, wherein

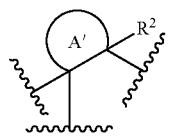

is selected from the group consisting of:

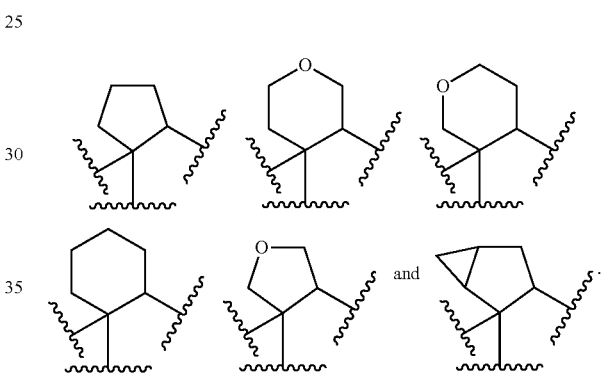

15. The compound of claim 1, or a pharmaceutically acceptable salt thereof, wherein

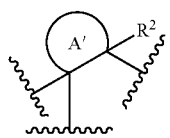

is selected from the group consisting of:

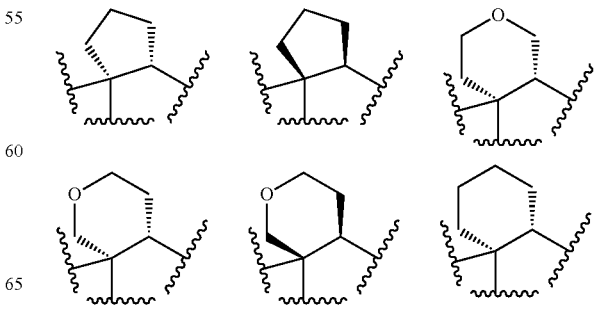

-continued
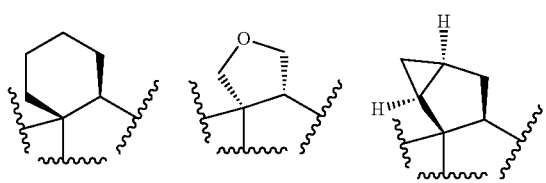
and
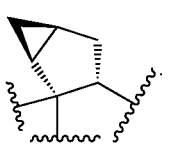
16. The compound of claim 1, or a pharmaceutically acceptable salt thereof, wherein
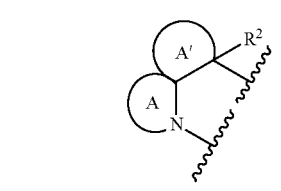
is selected from the group consisting of:
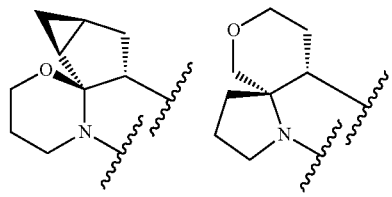
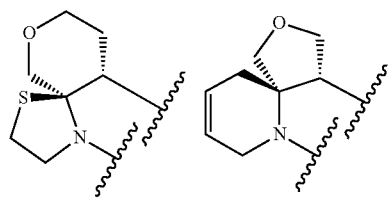
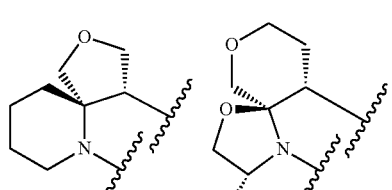
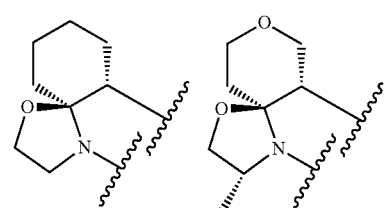
-continued
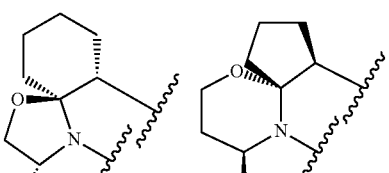
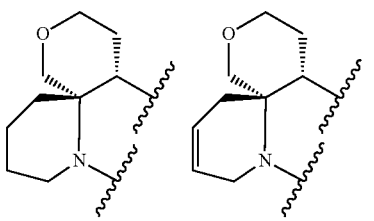
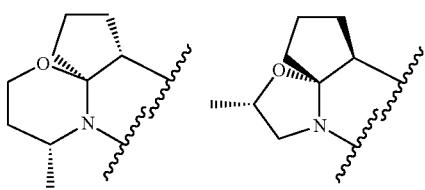
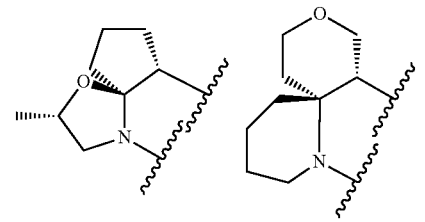
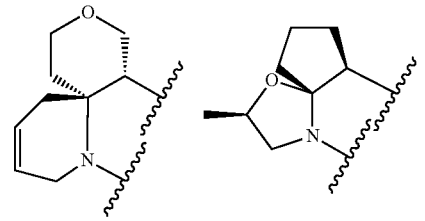
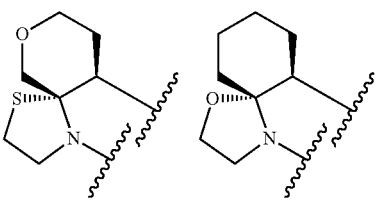
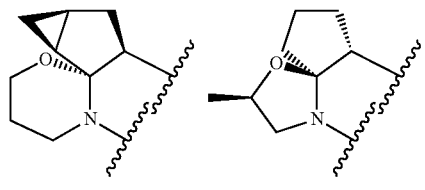

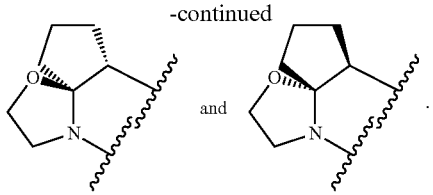 and

17. The compound of claim 1, or a pharmaceutically acceptable salt thereof, wherein $R^1$ is phenyl substituted with two or three $R^5$ groups, wherein each $R^5$ is independently selected from the group consisting of halogen and $C_{1-3}$alkyl.

18. The compound of claim 1, or a pharmaceutically acceptable salt thereof, wherein $R^1$ is phenyl substituted with two or three $R^5$ groups, wherein each $R^5$ is independently selected from the group consisting of fluoro and chloro.

19. The compound of claim 1, or a pharmaceutically acceptable salt thereof, wherein $R^1$ is selected from the group consisting of:

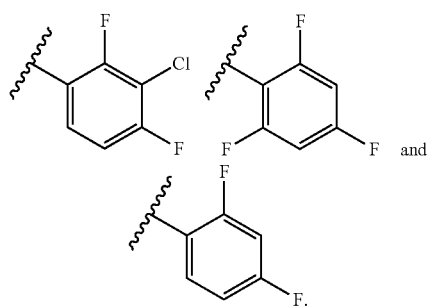 and

20. The compound of claim 1 selected from the group consisting of:

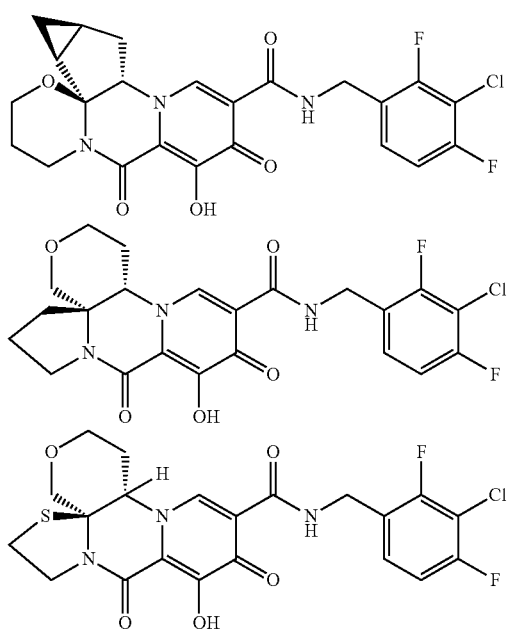

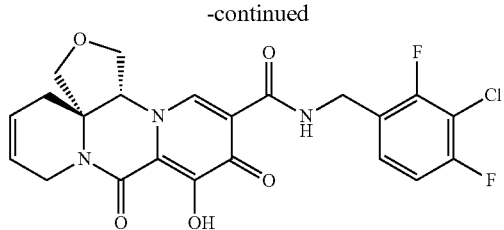

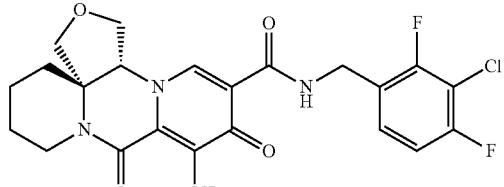

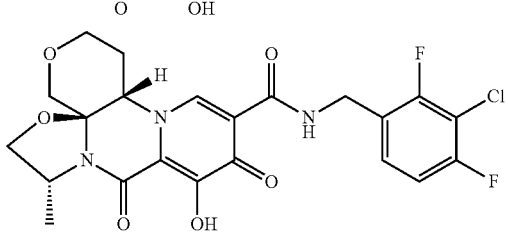

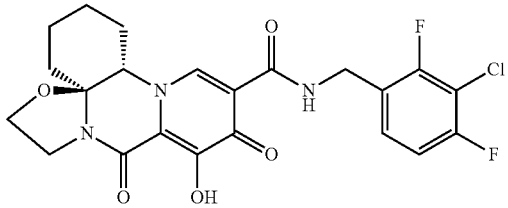

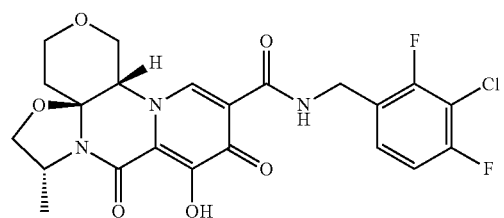

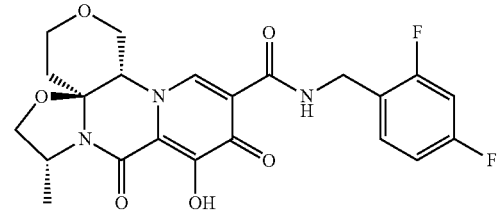

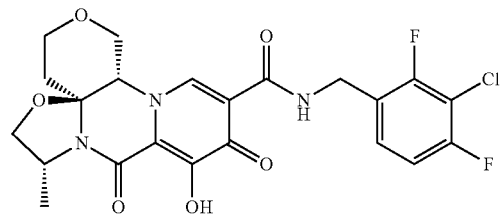

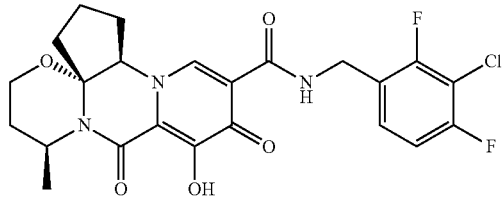

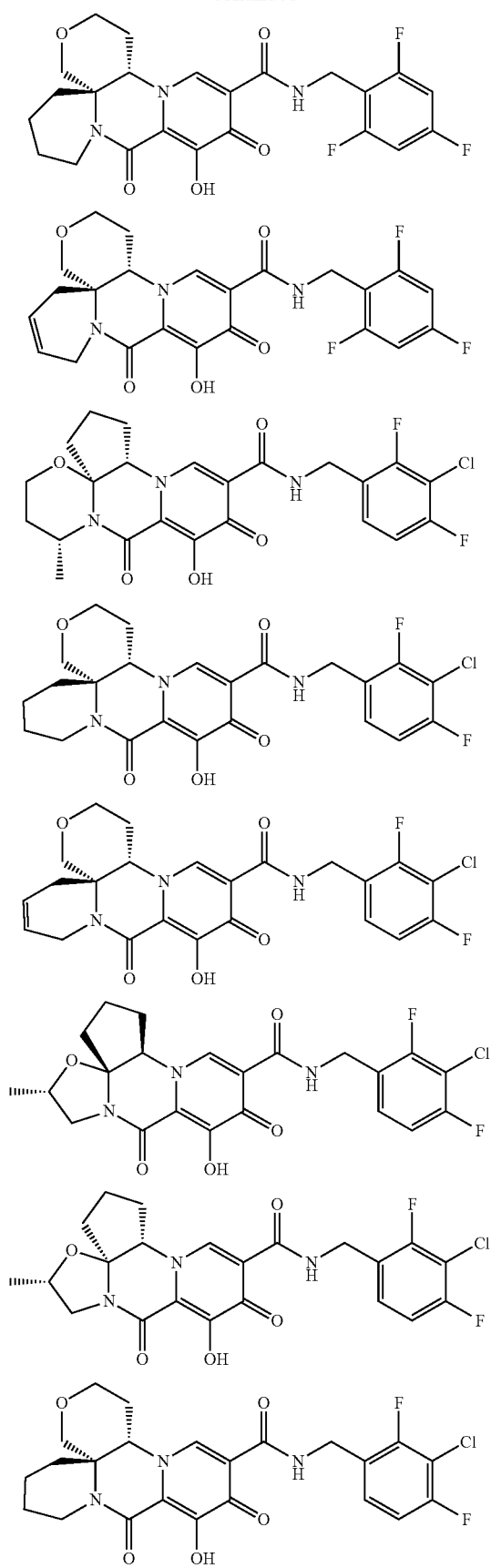
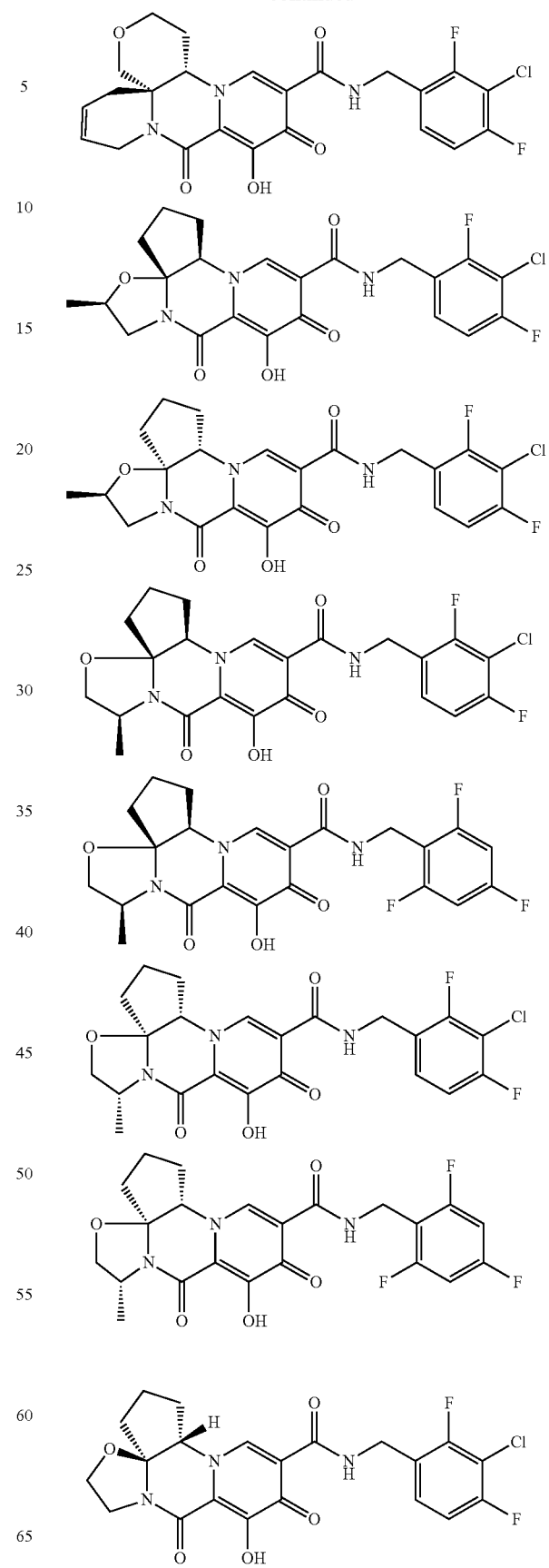

-continued

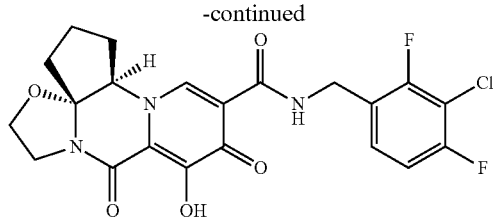

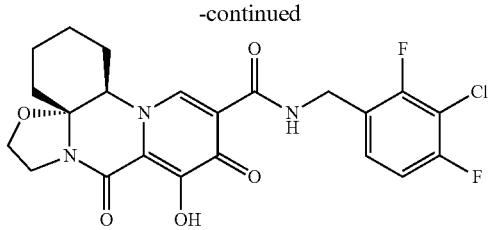

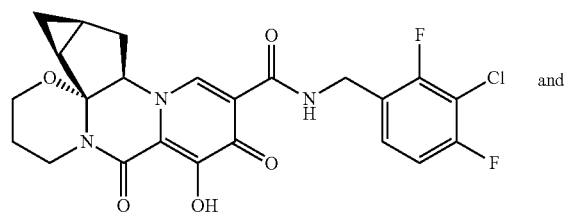

and or a pharmaceutically acceptable salt thereof.

21. A pharmaceutical composition comprising a compound of claim 1, or pharmaceutically acceptable salt thereof, and a pharmaceutically acceptable excipient.

22. The pharmaceutical composition of claim 21 further comprising a first additional therapeutic agent selected from the group consisting of abacavir sulfate, tenofovir, tenofovir disoproxil fumarate, tenofovir alafenamide, and tenofovir alafenamide hemifumarate; and a second additional therapeutic agent selected from the group consisting of emtricitabine and lamivudine.

23. A method of treating an HIV infection in a human comprising administering to the human a therapeutically effective amount of a compound of claim 1 or a pharmaceutical composition of claim 21.

24. The method of claim 23 further comprising administering to the human a first additional therapeutic agent selected from the group consisting of abacavir sulfate, tenofovir, tenofovir disoproxil fumarate, tenofovir alafenamide, and tenofovir alafenamide hemifumarate; and a second additional therapeutic agent selected from the group consisting of emtricitabine and lamivudine.

* * * * *